US007064243B2

(12) United States Patent
Liu et al.

(10) Patent No.: US 7,064,243 B2
(45) Date of Patent: Jun. 20, 2006

(54) SCREENS AND ASSAYS FOR AGENTS USEFUL IN CONTROLLING PARASITIC NEMATODES

(75) Inventors: Leo Liu, Weston, MA (US); Lucinda Burnam, Somerville, MA (US); Ann Sluder, Burlington, MA (US); Elizabeth Link, Brentwood, TN (US); Beth Westlund, Brookline, MA (US)

(73) Assignee: Cambria Biosciences LLC, Bedford, MA (US)

( * ) Notice: Subject to any disclaimer, the term of this patent is extended or adjusted under 35 U.S.C. 154(b) by 0 days.

(21) Appl. No.: 10/051,644

(22) Filed: Jan. 18, 2002

(65) Prior Publication Data

US 2003/0126625 A1    Jul. 3, 2003

Related U.S. Application Data

(60) Provisional application No. 60/263,081, filed on Jan. 18, 2001.

(51) Int. Cl.
*A01K 67/33* (2006.01)
*C12N 15/00* (2006.01)
*G01N 33/00* (2006.01)

(52) U.S. Cl. ............................. 800/13; 800/3; 800/21
(58) Field of Classification Search .................. 800/13, 800/25, 21
See application file for complete search history.

(56) References Cited

FOREIGN PATENT DOCUMENTS

WO    WO 00/54815    9/2000

OTHER PUBLICATIONS

Boag et al. International Journal for Parasitology, 2003, 33: 313-325.*
Britton et al. Molecular and Biochemical Parasitology, 1999, 103 : 171-181.*
Lakso et al. Journal of Neurochemistry, 2003, 86: 165-172.*
Winter et al. Journal of Biological Chemistry, 2003, 278(4): 2554-2562.*
Signor et al. Molecular Biology of the Cell, 1999, 10: 345-360.*
Gao et al., "Molecular characterisation and expression of two venom allergen-like protein genes in Heterodera glycines," Intl. J. Parasitol. 31: 1617-1625, 2001.*
Davies, et al., "Functional Overlap Between the mec-8 Gene and Five sym Genes in Caenorhabditis Elegans", *Genetics*, 153: 117-134, 1999.
Fitzgerald, et al., "Importance of the Basement Membrane Protein SPARC for Viability and Fertility in Caenorhabditis Elegans", *Current Biology*, 8: 1285-1288, 1998.
Hawdon, et al., "Cloning and Characterization of Ancylostoma-Secreted Protein", *The Journal of Biological Chemistry*, 271: 12: 6672-6678, 1996.

Koushika, et al., "Sorting and Transport in *C. Elegans*: A Model System with a Sequenced Genome", *Current Opinion in Cell Biology*, 12: 517-523, 2000.
Liu, "*Caenorhabditis Elegans* Venom Allergen-Like Protein (vap-1) mRNA, Complete Cds" XP-002246221.
Plenefisch, et al., "Secretion of a Novel Class of iFABPs in Nematodes: Coordinate Use of the Ascaris/Caenorhabditis Model Systems", *Molecular and Biochemical Parasitology*, 105: 223-236, 2000.
Riga, et al., "Biochemical Analyses on Single Amphidial Glands, Excretory-Secretory Gland Cells, Pharyngeal Glands and Their Secretions from the Avian Nematode *Syngamus Trachea*", *International Journal for Parasitology*, 25(10): 1151-1158, 1995.
International Search Report issued for corresponding PCT application PCT/US02/01332.
Zhan Bin, et al., Ancylostoma Secreted Protein (ASP-1) Homologues in Human Hookworms, *Molecular and Biochemical Parasitology*, 98 (1999) 143-149.
Mark Blaxter, Genes and Genomes of Necator Americanus and Related Hookworms, *International Journal for Parasitology*, 30 (2000) 347-355.
Thomas R. Burglin, et al., *Caenorhabditis Elegans* as a Model for Parasitic Nematodes, *International Journal for Parasitology* 28 (1998) 395-411.
Giuseppe Cassata, Rapid Expression Screening of Caenorhabditis Elegans Homeobox Open Reading Frames Using a Two-Step Chain Reaction Promoter-gfp Reporter Construction Technique, *Gene* 212 (1998) 127-135.
Robin B. Gasser, et al., Genomic and Genetic Research on Bursate Nematodes: Significance, Implications and Prospects, *International Journal for Parasitology*, 30, (2000) 509-534.
Jesus A. Gutierrez, Genomics: From Novel Genes to New Therapeutics in Parasitology, *International Journal for Parasitology*, 30 (2000) 247-252.

(Continued)

*Primary Examiner*—Scott D. Priebe
(74) *Attorney, Agent, or Firm*—Choate, Hall & Stewart, LLP

(57) ABSTRACT

The invention provides a method of identifying anti-nematode compounds and further provides transgenic nematodes that may be used to practice the method. In particular, the invention provides a screen for compounds that inhibit a nematode secretion pathway e.g, compounds that inhibit the secretion of proteins by nematodes. The transgenic nematodes express reporters for nematode secreted proteins. In preferred embodiments of the invention the screen is performed using *C. elegans*, i.e., certain embodiments of the invention utilize *C. elegans* and *C. elegans* secretory pathways as a model system for parasitic nematodes and parasitic nematode secretion pathways. The invention also provides pharmaceutical compositions that may be used in the treatment and prevention of nematode infection in humans and animals and anti-nematode agents that may be used to protect plants from plant-parasitic nematodes. In addition, the invention provides a genetic screen for identifying additional targets for anti-nematode compounds.

32 Claims, 12 Drawing Sheets

OTHER PUBLICATIONS

John M. Hawdon, et al., Cloning and Characterization of Ancylostoma-secreted Protein, *The Journal of Biological Chemistry*, 271, Mar. 22, 6672-6678, 1996.

J. M. Hawdon, et al., Developmental Adaptions in Nematodes, *Parasite- Host Association 1991*, 274-298.

John M. Hawdon, et al., Hookworm: Developmental Biology of the Infectious Process, *Current Opinion in Genetics & Development*, 1996, 6 618-623.

John M. Hawdon, Ancylostoma Secreted Protein 2: Cloning and Characterization of a Second Member of a Family of Nematode Secreted Proteins from Ancylostoma Caninum, *Molecular and Biochemical Parasitology*, 99, (1999) 149-165.

High-Throughput Isolation of *Caenorhabditis Elegans* Deletion Mutants, *Genome Research*, 9, 859-867.

Peter Hotez, et al., Metalloproteases of Infective Ancylostoma Hookworm Larvae and Their Possible Functions in Tissue Invasion and Ecdysis, Infection and Immunity, *American Society for Microbiology*, Dec. 1990, 3883-3892 00199567/123883.

Peter Hotez, et al., Molecular Mechanisms of Invasion by Ancylostoma Hookworms, *Molecular Approaches to Parasitology, 21-29, 1995 Wiley-Liss, Inc.*

Richard S. Hussey, et al., Nematode Parasitism of Plants, *Department of Plant Pathology University of Georgia*.

Iterated Profile Searches with PSI-Blast—a Tool for Discovery in Protein Databases, Computer Corner TIBS 23—Nov. 1998.

Detlef H. Kozian, et al., Comparative Gene-Expression Analysis, *The Center for Applied Genomics*.

Istvan Ladunga, Large-Scale Predictions of Secretory Proteins from Mammalian Genomic and EST Sequences, *Current Opinion in Biotechnology*, 2000, 11 13-18.

Kris N. Lambert, et al., Cloning and Characterization of an Esophageal-Gland-Specific Chorismate Mutase from the Phytoparasitic Nematode Meloidogyne Javanica, *MPMI*, 12, No. 4, 1999, 328-336.

Elizabeth M. Link, Therapeutic Target Discovery Using Caenorhabditis Elegans, *Ashley Publication*.

Rick M. Maizels, et al., *Toxocara Canis*: Genes Expressed by the Arrested Infective Larval Stage of a Parasitic Nematode, *International Journal for Parasitology*, 30 (2000) 495-508).

D.M. Miller, et al., Two-Color GFP Expression System for *C. Elegans*, *Bio Techniques*, 26, 914-921 (May 1999).

Huan M. Ngo, et al., Differential Sorting and Post-Secretory Targeting of Proteins in Parasitic Invasion, *Cell Biology*.

Plant Parasitic Nematodes: Digesting a Page from the Microbe Book, *Proc. Natl. Acad. Sci. USA*, 95, 4789-4790, Apr. 1998.

Masao Sakaguchi "Eukaryotic protein secretion," *Current Opinion in Biotechnology*, 1997, 8, 595-601.

Greet Smant et al., "Endogenous Cellulases in Animals: Isolation of B-1,4-Endoglucanase Genes from Two Species of Plant-Parasitic Cyst Nematodes", *Proc. Natl. Acad. Sci. USA*, 95, 4906, Apr. 1998 Biochemistry.

Marcelo Bento Soares, Identification and Cloning of Differentially Expressed Genes, *Current Opinion in Biotechnology* 1997, 8, 542-546.

S.A. Williams, et al., The Filarial Genome Project: Analysis of the Nuclear, Mitochondrial and Endosymbiont Genomes of Brugia Malayi, *International Journal for Parasitology*, 30 (2000) 411-419.

Valerie Moroz Williamson, et al., Nematode Pathogenesis and Resistance in Plants, *The Plant Cell*, 8, 1735-1745 1996.

* cited by examiner

FIG.1-1

VAP-1 amino acid sequence (SEQ ID NO:1)

MAVLAVVLLLACLERAVAQTFGCSNTKINDQARKMFYDAHNDARRSMAKGLE
PNKCGLLSGGKNVYELNWDCEMEAKAQEWADGCPSSFQTFDPTWGQNYATYM
GSIADPLPYASMAVNGWWSEIRTVGLTDPDNKYTNSAMRFANMANGKASAFG
CAYALCAGKLSINCIYNKIGYMTNAIIYEKGDACTSDAECTTYSDSQCKNGLCYK
APQAPVVETFTMCPSVTDQSDQARQNFLDTHNKLRTSLAKGLEADGIAAGAFAP
MAKQMPKLVKYSCTVEANARTWAKGCLYQHSTSAQRPGLGENLYMISINNMP
KIQTAEDSSKAWWSELKDFGVGSDNILTQAVFDRGVGHYTQMAWEGTTEIGCF
VENCPTFTYSVCQYGPAGNYMNQLIYTKGSPCTADADCPGTQTCSVAEALCVIP vap-1 cDNA nucleotide sequence (SEQ ID NO:2)

ATGGGCGGTATTAGCAGTGGTACTACTTCTAGCATGCCTCGGAGAGAGCGGTTG
CACAGACGTTCGGCTGCTCTAACAATGATGCCAAGATCAATGACCAGGCTCGTAAGAT
GTTCTATGATGCTCACAATGACGCGGAGCATGCCAAGAAGAATGTTTATGAATTGAATT
CCAAACAAGTGCGAGATGGAAGCAAAAGCTCAGGAGCAGAACGGATGTCCCA
GCTCTTTCCAGACATTGATCCGCTTCCATACGCTTCCATGGCTGTTAATGGGTGGT
GGGATCGATTGCTGATCCATCACGGACTTACGGACTTACGGATCCTGATAACAAGTACACTAA

FROM Fig.1-1

CAGTGCAATGTTCCGATTTGCTAATATGGCAAATGGTAAAGCTTCAGCTTTTG
GATGTGCATACGCGTTGTGCGCAGGAAAACTATCCATCAATTGCATTTACAA
CAAGATAGGATACATGACCAATGCACCACCTACTCAGATGAAAAAGGAGATGCCTGT
ACCAGTGACGGCTGAATGCACCACCTACTCAGACTCACAATGCAAAAACGGTC
TTTGCTATAAGGCACCTCAAGCTCCAGTCGTTGAGACTTTCACAATGTGCCCT
TCGGTCACGGACCAGTCGGATCAGGCGCGTCAAAACTTCTTGGACACCCATA
ACAAATTGCGTACAAGCCCTTGCCAAGGACTTGAAGCTGATGGAAATTGCCGC
TGGAGCATTTGCACCAGTTGCACCAATGGCCAAGCAAATGCCAAAACTGGTAAAATACAGC
TGCACAGTTGAAGCGCCACAGAGACCAGGACTCGGTGAAATCTTTATGATCAG
ATTCAACAAGCGCACAGAGACCAGGACTCGGTGAAATCTTTATGATCAG
CATTAACAACATGCCTAAAATTCAAACCCGGAGGACTCCTCAAAGGCTTGG
TGGTCCCAGTTGAAGACTTCGGGCGTTGGACATTACAACAAATGGCATGGGAAGGAAC
CAGTTTTTGATCGTCGTGGCGTTGTTGTGGAGAACTACATGTCCAACATTCACTTATTCCGTAT
TACTGAAATTGGATGTTTGTGGAGAACTACATGTCCAACAACTAATCTATACCAAGGG
GCCAATATGGTCCAGCGGGAAACTACATGAACCAACTAATCTATACCAAGGG
CTCACCATGCACAGCTGACGCCGATTGCCCAGGAACCCAGACATGCAGTGTC
GCTGAAGCATTATGTGTTATCCCTTAGTAAATTTTCTATGCAACTCTTTGAAA
GTCATATAATAAATATGCAAAATTAAAAAAAAAAAAAAAA

FROM Fig.1-2

VAP-2 amino acid sequence (SEQ ID NO:3)

MNVVLSAVTLFLIFRYAQTVNIEGSGGNDELLEQNVWNDVDDKVVEALGGLDD
ELLTEHVCNKSTITQLQQEIILTTHNELRRSLAFGKQRNKRGLMNGARNMYKLD
WDCELASLAANWSTSCPQHFMPQSVLGSNAQLFKRFYFYDGHDSTVHMRNA
MKYWWQQGEEKGNEDQKNRFYARRNYFGWANMAKGKTYRVGCSYIMCGDG
ESALFTCLYNEKAQCEKEMIYENGKPCCEDKDCFTYPGSKCLVPEGLCQAPSMV
KDDGGSFQCDNSLVSDVTRNFTLEQHNFYRSRLAKGFEWNGETNTSQPKASQM
IKMEYDCMLERFAQNWANNCVFAHSAHYERPNQGQNLYMSSFSNPDPRSLIHT
AVEKWWQELEEFGTPIDNVLTPELWDLKGKAIGHYTQMAWDRTYRLGCGIANC
PKMSYVVCHYGPAGNRKNNKIYEIGDPCEVDDDCPIGTDCEKTTSLCVISK vap-2 cDNA nucleotide sequence (SEQ ID NO:4)

ATGAACGTGGTCCTTTCCGCTGTCACTCTTTTTCTTATTTTTCGATATGCCAG
ACTGTGAATATAGAAGGCAGTGGAGGCAATGATGAGCTTCTTGAGCAGAACG
TGTGGAACGATGTAGACGACAAGGTTGTAGAAGCACTTGGTGGTCTTGATGA
TGAACTGCTAACCGAACATGTGTGTAACAAATGAATTACGAAGATCACTCAGCTACAG
CAGGAGATCATCTTGACAACCCACACAGAGGTCTCATGGCCATCACTTGCAGCCAATTGGTCAACCTCC
GAAAGCAAAGAACAAGAGAGGTCTCATGAACGGTGCCAGAGAAATATGTATA
AACTGGATTGGGATTGTGAACTGCTTGCCGCATCACTTGCAGCCAATTGGTCAACCTCC
TGCCCTCAGCACTTTATGCCGCAATCGGTACTTGGCCTCCAACGCTCAGCTTTT

To Fig.1-4

FIG.1-4    FROM Fig.1-3

```
TAAGCGTTTCTATTTTATTTTGATGGGCACGACTCTACTGTACATATGCGAA
ACGCGATGAAGTATTGGTGGCCAGCAAGGTGAAGAAAAAGGCAATGAGGATC
AGAAAAATAGATTCTATGCCAGACGAATTATTTTGGATGGGCAAACATGGC
AAAAGGAAAAACATATCGAGTTGGATGCTCGTATATTATGTGCGGCGACGGT
GAATCTGCACTTTTCACTTGTCTCTTTATAACGAAAAGCCCAATGCGAAAAG
AAATGATTACGAAAAATGAAAACCCTGCTGTGAGGATAAAGACTGTTTCAC
ATATCCAGGATCAAAATGTTAGTACCTGAAGGATTATGTCAAGCACCTTCTA
TGGTAAAGGATGATGGAGGAAGTTTCCAATGTGATAACTCCCTTGTCTCAGA
TGTCACCCGCAATTTCACTTTGGAGCAACACAATTTTTATAGATCTCGTCTTG
CAAAAGGTTTTGAATGGAAATGGAGTATGACTGTTGGAACGGTTTGCACAAAAC
TCAAATGATCAAAATTGCGTTTTCTACATGAGTTCTTCTCAAACCCTGATCCTAGAAGCCTT
TGGGCAAATAATTGCGTTTTCTACATGAGTTCTTCTCAAACCCTGATCCTAGAAGCCTT
AGGGTCAGAATCTCTACATGAGTTCTTCTCAAACCCTGATCCTAGAAGCCTT
ATACATACGGCCCGTCGACACCCGAATTGTGGATTTGAAGGGAAAGCGAT
CAATTGATAACGTTCTGACACCCGAATTGTGGATTTGAAGGGAAAGCGAT
AGGACATTACACTCAGATGCCTCGGATCGTCGTACGTGGTTTGTCACTATGGGCCAGCAGG
TCGCCAAACTGTCCGAAGATGTCGTACGTGGTTTGTCACTATGGGCCAGCAGG
CAACAGAAGAACAATAAAATCTATGAAATCGGGGATCCTTGCCGAAGTCGAT
GATGATTGCCCGATTGGAACAGATTGTGAAAAGACAACTTCTTTATGTGTGAT
CTCAAAATAA
```

FIG.3-1

CLUSTAL W Alignment of VAP-1, VAP-2, and selected other nematode VA proteins.

```
VAP-1N    1 ------------------------------------------MAVLAVVLLLACLERAVAQTFG  22
VAP-1C    1 ------------------------------------------------------PQAPVVETFTM  11
VAP-2N    1 MNVVLSAVTLFLIFRYAQTVNIEGSGGNDELLEQNVWNDVDDKVVEALGGLDDELLTEHV  60
VAP-2C    1 ---------------------------------------------------------SFQ   3
ASP-1N    1 --------------------------------------MFSPVIVSVIFTIAFCDASPARDGFG  26
ASP-1C    1 ------------------------------------------------------DVPETNQQ   8
VAP-3     1 -------------------------------------------------MNYLLLVVALAVG  13
MSP-1     1 -------------------------------------------------MSNKLIISILILTI  14

VAP-1N   23 CSNTKIN--DQARKMFYDAHNDARRSMAKGLEPN--KCGLLSGGKNVYELN-WDCEMEA   76
VAP-1C   12 CPSVT-DQSDQARQNFLDTHNKLRTSLAKGLEADGIAAGAFAPMAKQMPKLVKYSCTVEA   70
VAP-2N   61 CNKST--ITQLQQEIILTTHNELRRSLAFGKQRN--KRGLMNGARNMYKLD-WDCELAS  114
VAP-2C    4 CDNSLV--SDVTRNFTLEQHNFYRSRLAKGFEWNG-ETNTSQPKASQMIKME-YDCMLER  59
ASP-1N   27 CSNSG--ITDKDRQAFLDFHNNARRRVAKGVEDS--NSGKLNPAKNMYKLS-WDCAMEQ   80
ASP-1C    9 CPSNT-GMTDSVRDTFLSVHNEFRSSVARGLEPD--ALGGNAPKAAKMLKMV-YDCEVEA  64
VAP-3    14 CSADFG---SSGQNGIINAHNTLRSKIAKGTYVA--KGTQKSPGTNLLKMK-WDSAVAA  66
MSP-1    15 IYTVVNSLIVPEQNAVVDCINKYRSQLANGKTKN--KNGGNFPSGKDILEVS-YSKDLEK  71
```

FROM Fig.3-1

```
VAP-1N   77 KAQEWADGCPSSFQT--FDPT----WGQNYATYMGSI--ADPLPYASMAVNGWWSEI RTVG 129
VAP-1C   71 NARTWAKGCLYQHSTSAQRPG---LGENLYMISINN--MPKIQTAEDSSKAWWSELKDFG 125
VAP-2N  115 LAANMSTSCPQHFMPQSVLGS---NAQLFKRFYFYFDGHDSTVHMRNAMKYWWQQGEEKG 171
VAP-2C   60 FAQNWANNCVFAHSAHYERPN---QGQNLYMSSFSN--PDPRSLIHTAVEKWWQELEEFG 114
ASP-1N   81 QLQDAIQSCPSAFAG--IQG---VAQNVMSWSSSGGFPDPSVKIEQTLSGWWSGAKKNG 134
ASP-1C   65 SAIRHGNKCVYQHSHGEDRPG---LGENIYKTSVLK--FDKNKAAKQASQLWWNELKEFG 119
VAP-3    67 SAQNYANGCPTGHSG----DAG---LGENLYWWTSGSLGDLNQYGSAASASWEKEFQDYG 120
MSP-1    72 SAQRWANKCIFDHNGTDLYSGGKFYGENLYLDGDFEH-KNITQLMIDACNAWWGESTTDG 130

VAP-1N  130 LTD-------PDNK--YTNSA---MFRFANMANGKASAFGCAYALCAGKL------SINCL 172
VAP-1C  126 VGSD------NILTQA--VFDRG---VGHYTQMAWEGTTEIGCFVENCPTFT----YSVCQ 171
VAP-2N  172 NEDQ------KNR--FYARRN---YFGWANMAKGKTYRVGCSYIMCGDGES----ALFTCL 217
VAP-2C  115 TPID-----NVLTPE--LWDLKGKAIGHYTQMAWDRTYRLGCGIANCPKMS----YVVCH 163
ASP-1N  135 VGPD-----N-----KYNGGG--LFAFSNMVYSETTKLGCAYKVCGTKL------AVSCI 176
ASP-1C  120 VGPS-----NVLTTA--LWNRPGMQIGHYTQMAWDTTYKLGCAVVFCNDFT----FGVCQ 168
VAP-3   121 WKS------NLMTID--LFNTG---IGHATQMAWAKSNLIGCGVIKDCGRDSNGLNKVTVVCQ 171
MSP-1   131 VPPSWINNFLPTDNKENDEKFEAVGHWTQMAWAKTYQIGCALKVCHKPDCNGN--LIDCR 188
```

FROM Fig.3-2

```
VAP-1N  173 YNKIGYMTNAIIYEKGDACTSDAECTTYS--DSQCKNGLCYKA-------213
VAP-1C  172 YGPAGNYMNQLIYTKGSPCTADADCPGTQ--TCSVAEALC-V--IP-----212
VAP-2N  218 YNEKAQCEKEMIYENGKPCCEDKDCFTYPGSKCLVPEGLCQAPSMVKDDGG 268
VAP-2C  164 YGPAGNRKNNKIYEIGDPCEVDDDDCPIGT--DCEKTTSLC-V--ISK---205
ASP-1N  177 YNGVGYITNQPMWETGQACKTGADCSTYK--NSGCEDGLCTKGP-------218
ASP-1C  169 YGPGGNYMGHVIYTMGQPCS---QCSPGA--TCSVTEGLC--S--A--P--206
VAP-3   172 YKPQGNFINQYIYVSGATCS---GCPSGT--SCETSTGLCV----------207
MSP-1   189 YYPGGNGMGSPIYQQGKPAS---GCGKAG--PSTKYSGLCKPDPHQNN---231
```

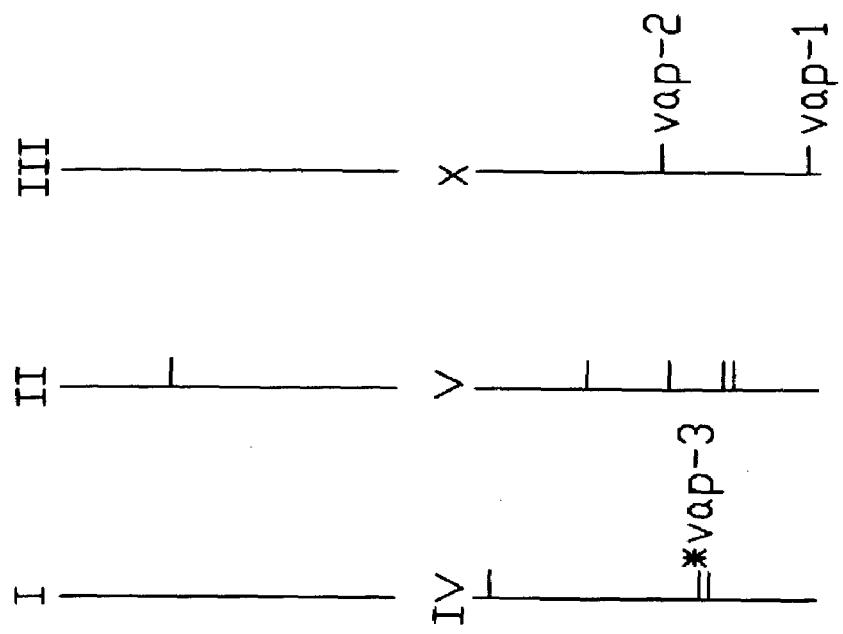
FIG. 4 Schematic map of selected C. elegans vap genes

SCREENS AND ASSAYS FOR AGENTS USEFUL IN CONTROLLING PARASITIC NEMATODES

CROSS-REFERENCE TO RELATED APPLICATION

This application claims priority to provisional application U.S. Ser. No. 60/263,081, filed Jan. 18, 2001, which is incorporated herein by reference.

GOVERNMENT SUPPORT

This invention was made in part with government support under grant no. 1R43AI/GM48340-01 awarded by the NIH. The Government has certain rights in the invention.

BACKGROUND OF THE INVENTION

Nematodes are elongated symmetrical roundworms that constitute one of the largest and most successful phyla in the animal kingdom. Many nematode species are free-living and feed on bacteria, whereas others have evolved into parasites of plants and animals, including humans. Human infections with parasitic nematodes are among the most prevalent Infections worldwide. Over one billion people, predominantly in tropical and subtropical developing countries, are infected with soil and vector-borne nematodes that cause a variety of debilitating diseases (Liu L. X., Weller P. F., Intestinal Nematodes. Chapter 181, in *Harrison's Principles of Internal Medicine*, Isselbacher K J, Braunwald E, Wilson J D, Martin J B, Fauci A S, Kasper D L, eds., New York: McGraw-Hill, pp. 916–920, 1994). Among these parasitic nematodes are *Ancylostoma* and *Necator* hookworms that cause anemia and malnutrition, *Ascaris* roundworms that can cause pulmonary and nutritional disorders, and *Strongyloides stercoralis* which can cause potentially lethal hyperinfection in immunocompromised patients (Liu L. X., Weller P. F., Strongyloidiasis and other intestinal nematode infections, *Infect Dis Clin N Am* 7, 655–682, 1993). Nematodes of the order *Spirurida* are responsible for onchocerciasis (river blindness) and lymphatic filariasis. Animal parasitic nematodes infect a wide variety of both domestic and wild animals. Major animal pathogens include *Haemonchus contortus*, which infects herbivorous vertebrates, *Trichinella spiralis*, the causative agent of trichinosis, and various members of the order *Ascaridida*, which infect pigs and dogs in addition to humans.

Plant parasitic nematodes also represent major problems, being responsible for many billions of dollars in economic losses annually. The most economically damaging plant parasitic nematode genera belong to the family Heterderidae of the order Tylenchida, and include the cyst nematodes (genera *Heterodera* and *Globodera*) and the root-knot nematodes (genus *Meloidogyne*). The soybean cyst nematode (*H. glycines*) and potato cyst nematodes (*G. pallida* and *G. rostochiensis*) are important examples. Root-knot nematodes infect thousands of different plant species including vegetables, fruits, and row crops. In contrast to many viral and bacterial pathogens, little is known about the molecular basis of nematode parasitism, limiting the available framework for rational anthelminthic (anti-nematode) drug development (David J. R., Liu L. X., Molecular biology and immunology of parasitic infections, Chapter 170 in *Harrison's Principles of Internal Medicine*, Isselbacher K J, Braunwald E, Wilson J D, Martin J B, Fauci A S, Kasper D L, eds., New York: McGraw-Hill, pp. 865–871, 1994).

Anti-nematode drug or pesticide discovery has traditionally relied either on direct screening of compounds against whole target organisms or on chemical modification of existing compounds, strategies that have resulted in relatively few classes of active agents acting against a limited number of known biological targets. For example, organophosphates and carbamates, the oldest extant class of nematicides, were developed many decades ago and target a single, biologically conserved enzyme, acetylcholinesterase. Imidazole derivatives such as benzimidazole exert their antiparasitic effects by binding tubulin. Levamisole acts as an agonist on the nicotinic acetylcholine receptor, and avermectins act as irreversible agonists at glutamate-gated chloride channels (Liu L. X., Weller P. F., Drug Therapy: Antiparasitic Drugs, *N Engl J Med* 334, 1178–1184, 1996). Unfortunately, there are certain debilitating nematode infections which are difficult if not impossible to cure with existing therapeutics. For example, in onchocerciasis, the adult female *Onchocerca volvulus* worms are refractory to even newer generation drugs (Liu L. X., Weller P. F., Drug Therapy: Antiparasitic Drugs, *N Engl J Med* 334, 1178–1184, 1996). In addition, drug resistance has emerged to all of these main classes of therapeutics, particularly in livestock animal applications in which their use is widespread (Sangster N. C., Gill J., Pharmacology of anthelminthic resistance, *Parasitol Today* 15, 141–146, 1999). Thus far it has not been possible to develop effective and practical vaccines, and even if such vaccines become available, effective anti nematode drugs will still be needed for treating established infections as well as offering the potential advantages prophylaxis and treatment for a broad spectrum of nematode parasites.

The drawbacks of existing agents that are currently used to control plant parasitic nematodes are equally or more significant. Fumigant nematicides such as methyl bromide and 1,3-dichloropropene, which kill nematodes by slowly diffusing through the soil, are phytotoxic and must be applied well before planting. Environmental concerns, primarily groundwater contamination, ozone depletion, and pesticide residues in food (National Research Council, *Pesticides in the Diet of Infants and Children* (Washington, D.C.: National Academy of Sciences, 1993) have prompted the removal of Aldicarb, DGBCP, and other toxic nematicides from the market by the Environmental Protection Agency, with methyl bromide to be withdrawn in the U.S. by 2002 (Johnson, S. L., Bailey, J. E., "Pesticide Risk Management and the United States Food Quality Protection Act of 1996", in *Pesticide Chemistry and Bioscience: The Food-Environment Challenge*, Brooks, G. T. and Roberts, T. R., (eds.), Cambridge: Royal Society of Chemistry, pp. 411–420, 1999). Physical control measures (such as solarization and hot water treatment), biological control measures (e.g., crop rotation), and integrated approaches have been used to ameliorate the damage caused by plant parasitic nematodes (Whitehead, A. G., *Plant Nematode Control*, Wallingford: CAB International, 1998), but no single method or combination of measures is uniformly effective.

Because of the rapidly increasing limitations of existing products, there is a need for innovation in anthelminthic discovery. There exists an urgent need for new agents active against pathogenic and parasitic nematode species, e.g., compounds active against animal or plant parasitic nematodes. To facilitate the discovery of new anti-nematode compounds, there exists a need for the identification and validation of additional biological targets (e.g., nematode genes and proteins) against which such compounds can be directed. Furthermore, there exists a need for the development of new methodologies and screening technologies for the identification of compounds active against nematodes. In particular, there exists a need for the development of screening assays that can be conveniently performed in a high throughput format.

SUMMARY OF THE INVENTION

The present invention addresses the foregoing needs by providing methods and reagents for identifying compounds that inhibit a nematode secretion pathway. Inhibiting a secretion pathway can comprise causing a decrease in expression of a gene encoding a nematode secretion product (e.g., by inhibiting expression of a gene encoding a nematode secretion product), inhibiting processing of a nematode secretion product, inhibiting secretion of a nematode secretion product, etc. The invention, further provides methods for identifying new biological targets for anti-nematode compounds, e.g., for identifying nematode genes and proteins toward which anti-nematode compounds can be developed. In addition, the invention provides methods and reagents for identifying compounds that stimulate or activate a nematode secretion pathway, where stimulating or activating a nematode secretion pathway can comprise causing an increase in expression of a gene encoding a nematode secretion product, activating or stimulating secretion of a nematode secretion product, activating or stimulating processing of a nematode secretion product, activating or stimulating secretion of a nematode secretion product, etc.

The practice of the present invention employs, unless otherwise indicated, conventional techniques of molecular biology, cell biology, recombinant DNA technology, microbiology, immunology, microscopy, and chemistry. Such techniques are explained in the literature. In addition, the present invention employs information on the biology, biochemistry, physiology, anatomy, etc., of *C. elegans*, and techniques known in the art for the propagation, study, manipulation, and storage of nematodes, particularly *C. elegans*, as described in Wood, W. B. and the Community of *C. elegans* Researchers, eds., *The Nematode Caenorhabditis elegans*, Cold Spring Harbor Laboratory Press, Cold Spring Harbor, N.Y., 1988; Riddle, D. L. et al., eds., *C. elegans II*, Cold Spring Harbor Laboratory Press, Cold Spring Harbor, N.Y., 1997; Epstein, H. and Shakes, D., eds., *Caenorhabditis elegans: Modern Biological Analysis of an Organism, Methods in Cell Biology*, Vol., 43, Academic Press, San Diego, 1995. The contents of all references cited in this document, including patents, patent applications, books, journal articles, etc., are herein incorporated by reference. This disclosure references various Internet sites. The various sites are indicated herein as beginning with the characters "www" or "ftp". It is to be understood that the characters "http://" must appear at the beginning of the uniform resource locator in order to provide browser-executable code. The contents of the referenced Internet sites are incorporated herein by reference as of Jan. 18, 2001.

In one aspect, the invention provides a transgenic nematode, the cells of which contain a transgene comprising a DNA sequence including a regulatory element of a gene that encodes a nematode secretion product or a homolog thereof operably linked to a DNA sequence encoding a detectable marker. In certain embodiments of the invention the transgene further comprises at least a portion of the coding sequence of the gene, so that transgene encodes at least a portion of a nematode secreted protein or homolog thereof fused to a detectable marker. The transgene optionally includes partial or complete sequence from one or more introns and/or from the 3' UTR of the gene. Preferably the transgenic nematode is *C. elegans*. In preferred embodiments of the invention the gene is a *C. elegans* homolog of a protein that is secreted by a parasitic nematode species. The detectable marker can be, for example, a fluorescent polypeptide, a chemiluminescent polypeptide, an epitope tag, or an enzyme. Particular examples of appropriate markers include, but are not limited to, green fluorescent protein, luciferase, chloramphenicol acetyl transferase, xanthine-guanine phosphoribosyl transferase, beta-galactosidase, a Myc tag, and an HA tag. The Myc tag is discussed further in the Examples. The HA tag is the influenza hemaglutinnin epitope YPYDVPDYA (SEQ ID NO: 25). Both of these tags are well known in the art.

In another aspect, the invention provides a method of identifying a compound that inhibits a nematode secretion pathway. The method comprises the steps of: (1) providing a nematode, wherein the nematode produces a secretion product; (2) contacting the nematode with a test compound; and (3) detecting a decrease in the activity or amount of the secretion product when the test compound is present versus when the test compound is absent. In certain preferred embodiments of the invention the nematode is a transgenic nematode of the invention that expresses a transgene encoding a detectable marker and, optionally, at least a portion of a nematode secretory protein. In certain preferred embodiments of the invention the detecting step comprises detecting the secretion product in a culture medium in which the nematode is cultured. The secretory product can be detected in any of a variety of ways. For example, if the secretory product is a protein, the detection can be performed immunologically. If the secretory product comprises a fluorescent moiety, the product can be detected by monitoring fluorescence. The invention further provides a compound identified by the afore-mentioned method.

In another aspect, the invention provides a method of identifying a compound that stimulates or activates a nematode secretion pathway. The method comprises the steps of: (1) providing a nematode, wherein the nematode produces a secretion product; (2) contacting the nematode with a test compound; and (3) detecting an increase in the activity or amount of the secretion product when the test compound is present versus when the test compound is absent. In certain preferred embodiments of the invention the nematode is a transgenic nematode of the invention that expresses a transgene encoding a detectable marker and, optionally, at least a portion of a nematode secretory protein. In certain preferred embodiments of the invention the detecting step comprises detecting the secretion product in a culture medium in which the nematode is cultured. The secretory product can be detected in any of a variety of ways. For example, if the secretory product is a protein, the detection can be performed immunologically. If the secretory product comprises a fluorescent moiety, the product can be detected by monitoring fluorescence. The invention further provides a compound identified by the afore-mentioned method. The invention provides a number of other methods for identifying compounds that inhibit or activate a nematode secretion pathway. The invention provides a method of identifying a compound that inhibits a nematode secretion pathway comprising steps of: (1) providing a population of nematodes, wherein the nematodes produce a secretion product; (2) dispensing approximately equal numbers of the nematodes into a plurality of vessels; (3) contacting the nematodes in each of one or more of the vessels with one or more test compounds; and (4) detecting a decrease in the activity or amount of the secretion product in one or more of the vessels when the one or more test compounds are present versus when the one or more test compounds are absent. The invention further provides a method of identifying a compound that inhibits a nematode secretion pathway comprising steps of: (1) providing a nematode, wherein the nematode secretes a secretion product; (2) contacting the nematode with a test compound; and (3) detecting a decrease in the activity or amount of the secretion product when the test compound is present versus when the test compound is absent. The invention also provides a method of identifying a compound that inhibits a nematode secretion pathway comprising steps of: (1) providing a population of nematodes, wherein the nematodes secrete a secretion product; (2) dispensing approximately equal numbers of the nematodes into each of a plurality of vessels; (3) contacting the nematodes in each of one or more vessels with one or more test compounds; and (4) detecting a decrease in the activity or amount of the secretion product produced by the nematodes in one or more of the vessels when the one or more test compounds are present versus when the one or more test compounds are absent. The invention also provides a method of identifying a compound that inhibits a nematode secretion pathway comprising steps of: (1) providing a nematode, wherein the nematode expresses a gene encoding a secreted product; (2) contacting the nematode with a test compound; and (3) detecting a decrease in the activity or amount of the expression product of the gene encoding a secreted product when the one or more test compounds are present versus when the one or more test compounds are absent. Yet another method of identifying a compound that inhibits a nematode secretion pathway comprising steps of: (1) providing a population of nematodes, wherein the nematodes express a gene encoding a secretion product; (2) dispensing approximately equal numbers of the nematodes into each of a plurality of vessels; (3) contacting the nematodes in each of one or more of the vessels with one or more test compounds; and (4) detecting a decrease in the activity or amount of the expression product of the gene encoding a secreted product in one or more of the vessels when the one or more test compounds are present versus when the one or more test compounds are absent.

In another aspect, the invention provides a method of identifying a compound that stimulates a nematode secretion pathway comprising steps of: (1) providing a nematode, wherein the nematode produces a secretion product; (2) contacting the nematode with a test compound; and (3) detecting an increase in the activity or amount of the secretion product when the test compound is present versus when the test compound is absent. The invention further provides a method of identifying a compound that stimulates a nematode secretion pathway comprising steps of: (1) providing a population of nematodes, wherein the nematodes produces a secretion product; (2) dispensing approximately equal numbers of the nematodes into each of a plurality of vessels; (3) contacting the nematodes in each of one or more of the vessels with one or more test compounds; and (4) detecting an increase in the activity or amount of the secretion product produced by the nematodes in one or more of the vessels when the one or more test compounds are present versus when the one or more test compounds are absent. In addition, the invention provides a method of identifying a compound that stimulates a nematode secretion pathway comprising steps of: (1) providing a nematode, wherein the nematode secretes a secretion product; (2) contacting the nematode with a test compound; and (3) detecting an increase in the activity or amount of the secretion product when the test compound is present versus when the test compound is absent. The invention further provides a method of identifying a compound that stimulates a nematode secretion pathway comprising steps of: (1) providing a population of nematodes, wherein the nematodes secrete a secretion product; (2) dispensing approximately equal numbers of the nematodes into each of a plurality of vessels; (3) contacting the nematodes in each of one or more of the vessels with one or more test compounds; and (4) detecting an increase in the activity or amount of the secretion product in one or more of the vessels when the one or more test compounds are present versus when the one or more test compounds are absent. The invention also provides a method of identifying a compound that stimulates a nematode secretion pathway comprising steps of: (1) providing a nematode, wherein the nematode expresses a gene encoding a secreted product; (2) contacting the nematode with a test compound; and (3) detecting an increase in the activity or amount of the expression product of a gene encoding a secreted product when the test compound is present versus when the test compound is absent. In addition, the invention provides a method of identifying a compound that stimulates a nematode secretion pathway comprising steps of: (1) providing a population of nematodes, wherein the nematodes express a gene encoding a secretion product; (2) dispensing approximately equal numbers of the nematodes into each of a plurality of vessels; (3) contacting the nematodes in one or more of the vessels with one or more test compounds; and (4) detecting an increase in the activity or amount of the expression product of a gene encoding a secreted product in one or more of the vessels when the one or more test In another aspect, the invention provides a method of generating a nematode for use in screening for secretion inhibitors and/or stimulators comprising the steps of: (1) selecting a parasitic nematode secretory protein; (2) identifying a *C. elegans* homolog of the protein selected in step (1); (3) identifying a nucleic acid comprising a regulatory region of a *C. elegans* gene encoding the *C. elegans* homolog identified in step (2); and (4) generating a transgenic nematode, wherein the cells of the transgenic nematode comprise a nucleic acid sequence including the regulatory region identified in step (3) operably linked to a nucleic acid sequence encoding a detectable marker. The nucleic acid sequence of step (4) may further comprise at least a portion of the coding sequence of the *C. elegans* homolog of a parasitic nematode secretory protein, so that the transgene encodes at least a portion of a nematode secretory protein or homolog thereof fused to a detectable marker. The nucleic acid sequence may optionally comprise partial or complete sequence from one or more introns and/or from the 3' UTR of the gene encoding the *C. elegans* homolog. The marker can be, but is not limited to, any of those mentioned above.

In another aspect the invention provides vectors, e.g. plasmids, comprising a polynucleotide encoding VAP-1, VAP-2, or another VAP family member. In one preferred embodiment the vector comprises a polynucleotide that encodes the polypeptide of SEQ ID NO:1 (VAP-1 amino acid sequence), or a portion or variant thereof. In certain preferred embodiments the polynucleotide comprises the polynucleotide sequence of SEQ ID NO:2 (vap-1 cDNA nucleotide sequence) or a fragment thereof. In another preferred embodiment the vector comprises a polynucleotide that encodes the polypeptide of SEQ ID NO:3 (VAP-2 amino acid sequence), or a portion or variant thereof. In certain preferred embodiments the polynucleotide comprises the polynucleotide sequence of SEQ ID NO:4 (vap-2 cDNA nucleotide sequence) or a portion thereof. In preferred embodiments of the invention the vectors contain a regulatory element, i.e., a genetic control element, operably linked to the polynucleotide, wherein the regulatory element directs transcription of the polynucleotide. Preferred regulatory elements comprise between 1 nucleotide and 10 kB of sequence extending in a 5' direction from the start codon of a member of the *C. elegans* vap gene family (e.g., upstream of the vap-1 start codon in the case of a vector that comprises vap-1 coding sequences; upstream of the vap-2 start codon in the case of a vector that comprises vap-2 coding sequences). In particular, the invention provides a vector comprising a regulatory element including a polynucleotide sequence comprising the *C. elegans* vap-1 promoter operably linked to a polynucleotide encoding a detectable marker and further provides a vector comprising a regulatory element including a polynucleotide sequence comprising the *C. elegans* vap-2 promoter operably linked to a polynucleotide encoding a detectable marker.

In certain preferred embodiments of the invention the portion referred to above comprises at least 10 consecutive residues of SEQ ID NO:1. The invention further provides a vector comprising a polynucleotide that encodes a polypeptide, the amino acid sequence of which comprises a sequence at least 50% identical to SEQ ID NO:1 and a vector comprising a regulatory element operably linked to the polynucleotide sequence. In certain preferred embodiments of the invention the regulatory element contained in any of the vectors is a 5' regulatory region comprising between 1 nucleotide and 10 kB of sequence extending in a 5' direction from the start codon of the *C. elegans* vap-1 gene.

The invention also provides the vectors described above, further comprising a polynucleotide sequence that encodes a detectable marker in frame with the polynucleotide sequence of SEQ ID NO: 2 or a portion thereof. In certain embodiments of the invention the vectors comprise a polynucleotide sequence encoding a detectable marker under the control of a regulatory element such as those described above. In these embodiments the vector can also comprise a polynucleotide sequence that encodes a VAP family member (e.g., VAP-1) or a portion thereof, preferably in frame with the sequence encoding the detectable marker. However, the vector need not include any sequences encoding a VAP. In certain embodiments of the invention, in addition to a vap promoter region the vector may contain additional noncoding regions such as intron sequences, 3' untranslated regions, etc. In certain embodiments of the invention the vectors and regulatory elements are adapted for expression of the polynucleotide in a bacterial cell, a yeast cell, an insect cell, or a mammalian cell. The invention further provides host cells, e.g., bacterial, yeast, insect, and mammalian cells containing an expression vector containing the polynucleotide encoding the polypeptide having the sequence of SEQ ID NO:1 or a fragment thereof. In addition, the invention provides a transgenic nematode, the cells of which contain a transgene comprising one of the vectors of the invention.

The invention further provides vectors as described above comprising, rather than the polynucleotide sequences above, a polynucleotide sequence that encodes *C. elegans* VAP-2 (SEQ ID NO: 3) (e.g., the polynucleotide sequence of SEQ ID NO: 4, or a portion thereof). For those vectors that contain a regulatory element in addition to vap-2 sequences, the regulatory element preferably comprises between 1 nucleotide and 10 kB of sequence extending in a 5' direction from the start codon of the *C. elegans* vap-2 gene.

The invention further provides vectors similar to those described for VAP-1 and VAP-2 but corresponding to different members of the VAP family (e.g., containing regulatory sequences upstream of a different VAP family member operably linked to a polynucleotide encoding a detectable marker and/or operably linked to coding sequences encoding the VAP family member of a portion thereof.

In addition, the invention provides a method of expressing a polynucleotide or polypeptide in a *C. elegans* amphid sheath cell. As described in Examples 4, 8, and 9, reporter constructs comprising a vap-1 regulatory region operably linked to a coding sequence result in expression of the encoded protein in the amphid sheath cell. Thus constructs comprising a vap-1 regulatory region (e.g., between 1 nucleotide and 10 kB of sequence upstream from the vap-1 start codon) operably linked to a heterologous sequence, result in tissue-specific expression of the sequence.

In another aspect, the invention provides a pharmaceutical composition comprising a compound identified according to the method described above (i.e., the method for identifying an inhibitor of a nematode secretory pathway) and a pharmaceutically acceptable carrier. The invention further provides a method of preventing, treating, and/or reducing the likelihood of nematode infection in an individual (e.g., a human or animal) comprising the steps of identifying an individual at risk of or suffering from a nematode infection and administering the inventive pharmaceutical composition.

In yet another aspect, the invention provides an anti-nematode agent for use in preventing, treating, and/or reducing nematode infestation of a plant comprising a compound identified according to the method described above (i.e, the method for identifying an inhibitor of a nematode secretory pathway) and an agriculturally acceptable carrier. In addition, the invention provides methods of preventing, treating, and/or reducing nematode infestation of a plant comprising the steps of identifying a plant at risk of nematode infestation and applying the inventive anti-nematode agent to the plant or to the vicinity of the plant and/or treating soil in which a plant is to be grown with the inventive anti-nematode agent and/or treating the plant with the inventive anti-nematode agent. The invention further provides a method of preventing, treating, and/or reducing nematode infestation comprising applying an anti-nematode agent of the invention to a seed from which a plant is grown, prior to planting the seed.

The invention also provides a method of identifying a target for anti-nematode compound development. The method comprises steps of (1) providing an assay for a nematode secretion pathway; (2) mutagenizing a population of nematodes; (3) identifying, using the assay, a mutant nematode with an alteration in the nematode secretion pathway, wherein the nematode has a mutation in a gene; and (4) cloning the gene, thereby identifying a target for anti-nematode compound development. The term target can refer to the gene itself and/or to a gene product, e.g., an RNA or protein encoded by the gene. In certain preferred embodiments of the invention the assay comprises detecting a nematode secretion product. Preferably the population of nematodes are *C. elegans*. The invention further provides a mutant nematode identified according to this inventive method.

BRIEF DESCRIPTION OF THE DRAWING

FIG. 1 shows amino acid sequences for VAP-1 and VAP-2 and nucleotide sequences for the vap-1 and vap-2 cDNAs.

FIG. 3 shows a CLUSTAL W alignment of the N and C terminal VAP domains of VAP-1 and VAP-2 with selected other nematode venom allergen proteins. The figure shows the amino acid sequences of VAP-1N (SEQ ID NO: 26), VAP-1C (SEQ ID NO: 27), VAP-2N (SEQ ID NO: 28), VAP-2C (SEQ ID NO: 29); ASP-1N (SEQ ID NO: 30); ASP-1C (SEQ ID NO: 31); VAP-3 (SEQ ID NO: 32); MSP-1 (SEQ ID NO: 33). SEQ ID NO: 26 corresponds to residue numbers 1–213 of SEQ ID NO: 1. SEQ ID NO: 27 corresponds to residue numbers 214–425 of SEQ ID NO: 1. SEQ ID NO: 28 corresponds to residue numbers 1–268 of SEQ ID NO: 3. SEQ ID NO: 29 corresponds to residue numbers 269–473 of SEQ ID NO: 3.

FIG. 4 shows a schematic map of selected *C. elegans* vap genes. The asterisk represents 11 single-domain vap genes clustered near vap-3 on the overlapping cosmids C39E9 and F49E11 on chromosome 4.

BRIEF DESCRIPTION OF THE TABLES

Figure 2:
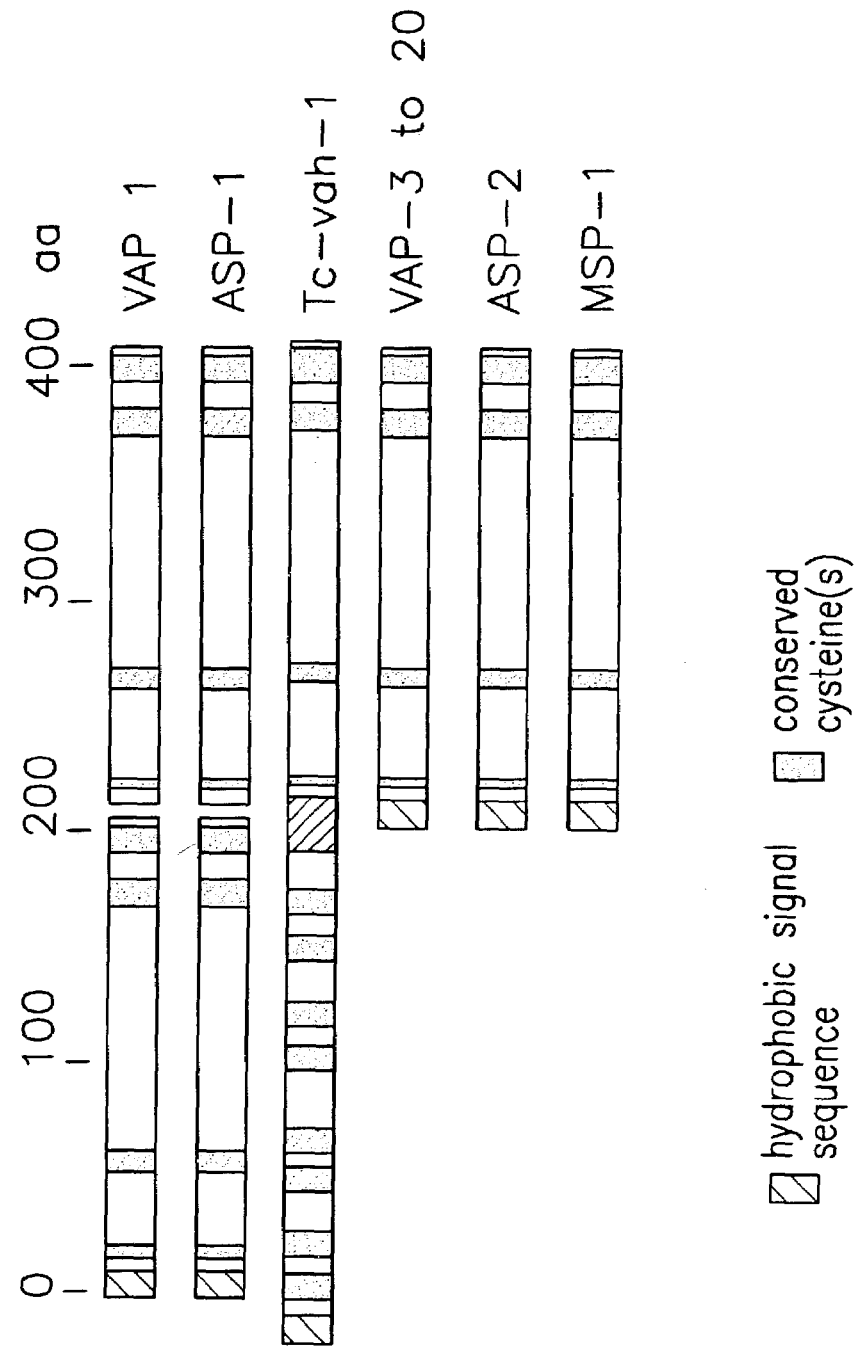
FIG. 2 shows a schematic diagram of nematode venom allergen protein domains.

Table 1 provides a listing of and information about selected nematode venom allergen proteins.

Table 2 provides a listing of various parasitic nematode orders and genera along with host name and common names of the worm or associated disease.

DEFINITIONS

The following definitions are provided to facilitate description and understanding of the invention. Terms not defined here or elsewhere in the document are taken to have the meaning generally accepted in the art.

Gene: For the purposes of the present invention, the term "gene" has its meaning as understood in the art. However, it will be appreciated by those of ordinary skill in the art that the term "gene" has a variety of meanings in the art, some of which include gene regulatory sequences (e.g., promoters, enhancers, etc.) and/or intron sequences, 3' untranslated regions, etc., and others of which are limited to coding sequences. It will further be appreciated that definitions of "gene" include references to nucleic acids that do not encode proteins but rather encode functional RNA molecules such as tRNAs. For the purpose of clarity we note that, as used in the present application, the term "gene" generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid.

Gene product or expression product: A gene product or expression product is, in general, an RNA transcribed from the gene or a polypeptide encoded by an RNA transcribed from the gene.

Homology: The term "homology" refers to a degree of similarity between two or more nucleic acid sequences or between two or more amino acid sequences. As is well known in the art, given any nucleotide or amino acid sequence, homologous sequences may be identified by searching databases (e.g., GenBank, EST [expressed sequence tag]databases, GST [gene sequence tag] databases, GSS [genome survey sequence] databases, organism sequencing project databases) using computer programs such as BLASTN for nucleotide sequences and BLASTP, gapped BLAST, and PSI-BLAST for amino acid sequences. These programs are described in Altschul, SF, et al., Basic local alignment search tool, *J. Mol. Biol.*, 215(3): 403–410, 1990, Altchul, S F and Gish, W, *Methods in Enzymology*, and Altschul, S F, et al., "Gapped BLAST and PSI-BLAST: a new generation of protein database search programs", *Nucleic Acids Res.* 25:3389–3402, 1997.

In addition to identifying homologous sequences, the programs mentioned above typically provide an indication of the degree of homology. Determining the degree of identity or homology that exists between two or more amino acid sequences or between two or more nucleotide sequences can also be conveniently performed using any of a variety of other algorithms and computer programs known in the art. Discussion and sources of appropriate programs may be found, for example, in Baxevanis, A., and Ouellette, B. F. F., *Bioinformatics: A Practical Guide to the Analysis of Genes and Proteins*, Wiley, 1998; and Misener, S. and Krawetz, S. (eds.), *Bioinformatics Methods and Protocols* (Methods in Molecular Biology, Vol. 132), Humana Press, 1999.

Nematode secretion pathway: The series of biochemical and physiological processes beginning with the synthesis of a nematode secretion product and leading to its secretion.

Nematode secretory product: A nematode secretory product, also referred to as a secretion product, nematode secreted product, or nematode secretion, is a molecule that is synthesized by a nematode and is transported to the exterior of the nematode, where the exterior of the nematode includes body cavities, intestine, organs adapted for feeding, organs adapted for defecation, sensory organs in communication with the environment, and any other organ or orifice that is in communication with the exterior world. A nematode secretory product is to be distinguished from a waste product or a byproduct of cellular metabolism or digestion. In the case of certain parasitic nematodes, e.g., hookworms, secretory products are referred to in the literature as excretory/secretory (ES) products, and the secretory system is referred to as the ES system. Such products, systems, etc., will be referred to as secretory products, systems, etc., herein.

Operably linked: The term "operably linked"refers to a relationship between two nucleic acid sequences wherein the expression of one of the nucleic acid sequences is controlled by, regulated by, modulated by, etc., the other nucleic acid sequence. For example, a promoter is operably linked with a coding sequence if the promoter controls transcription of the coding sequence. Preferably a nucleic acid sequence that is operably linked to a second nucleic acid sequence is covalently linked, either directly or indirectly, to such a sequence, although any effective three-dimensional association is acceptable.

Signal Sequence: A signal sequence is a relatively short stretch of amino acids (signal peptide) that is sufficient, when present within a polypeptide that is being translated, to direct the partially synthesized polypeptide to enter the secretory pathway. The term is also used herein to refer to a nucleotide sequence that encodes a signal peptide.

Transgenic: As used herein a transgenic organism is an organism in which one or more of the cells of the organism contain a heterologous nucleic acid introduced by way of human intervention by any of a variety of techniques well known in the art. The nucleic acid is introduced into the cell directly or indirectly by introduction into a precursor of the cell by way of deliberate genetic manipulation, e.g., by microinjection, transfection, transformation, transposon-mediated transfer, DNA microparticle bombardment, electroporation, infection with a recombinant virus, etc. One of ordinary skill in the art will be able to select the appropriate technique depending upon the organism and purpose for which the transgenic organism is to be created. The recombinant nucleic acid molecule may be integrated into a chromosome of the animal (e.g., in the case of *C. elegans* typically taking the form of an integrated array) or may be extrachromosomal, e.g., it may be an extrachromosomal array, a plasmid, etc. The transgene may be expressed in some or all of the cells of the animal. The temporal and/or spatial expression pattern of the transgene typically depends, at least in part, on sequences such as regulatory sequences in the transgene and/or the chromosomal location of the transgene in those instances in which the transgene integrates into the chromosome.

Transgene: As used herein, the term "transgene" refers to a nucleic acid sequence that is partly or entirely heterologous, i.e., foreign to the organism or cell into which it is introduced or is homologous to an endogenous gene of the organism or cell into which it is introduced but is designed to (i) alter the genome of the organism or cell (e.g., be inserted at a location different to the endogenous location or inserted so as to create a partial or complete knockout of the endogenous gene) or (ii) be located extrachromosomally. A transgene can include one or more regulatory sequences (e.g., promoter, enhancer, polyadenylation signal, splice sites, etc.). A transgene can contain both coding and noncoding sequences, including introns.

Vector: A vector, as used herein, is a nucleic acid molecule that includes sequences sufficient to direct in vivo or in vitro replication of the molecule. These may either be self-replication sequences or sequences sufficient to direct integration of the vector into another nucleic acid present in a cell (either an endogenous nucleic acid or one introduced into the cell by experimental manipulation), so that the vector sequences are replicated during replication of this nucleic acid. Preferred vectors include a cloning site, at which foreign nucleic acid molecules may be introduced. Vectors may include control sequences that have the ability to direct in vivo or in vitro expression of nucleic acid sequences introduced into the vector. Such control sequences may include, for example, transcriptional control sequences (e.g., promoters, enhancers, terminators, etc.), splicing control sequences, translational control sequences, etc. Vectors may also include a coding sequence, so that transcription and translation of sequences introduced into the vector results in production of a fusion protein.

DETAILED DESCRIPTION OF CERTAIN EMBODIMENTS

The present invention involves the use of the free-living nematode *Caenorhabditis elegans* (*C. elegans*) as a model system for the identification of anthelminthic agents. The invention encompasses the recognition that components of secretory pathways in parasitic nematodes represent promising targets for the development of new agents for nematode control. The invention further encompasses the recognition that secretory pathways and secretory products of parasitic nematodes have counterparts in *C. elegans*. The invention exploits the shared biology between *C. elegans* and parasitic nematode species and draws upon the wealth of information and experimental techniques available for the study of *C. elegans* to develop assays and screens for inhibitors of nematode secretory pathways. In order that the invention may be better understood, the following section discusses certain aspects of parasitic nematodes with particular reference to nematode secretory products and their role in nematode parasitism. The subsequent section offers an overview of the use of *C. elegans* as a model system. Various aspects of the invention are discussed in the remaining sections.

A. Parasitic Nematodes and Their Secreted Products

The life cycles of both free-living and parasitic nematodes involve a series of larval stages, generally four designated L1 through L4, separated by molts during which feeding, growth, development, and activity cease, and a new external cuticle is deposited. The old cuticle is then shed, and the animal resumes feeding, growth, and other activities. Following the L2 stage, many parasitic nematodes arrest development until infection of the host occurs. The developmental arrest can persist for prolonged and variable periods of time, during which the animal exhibits phenotypes specialized for infectivity. For example, during the infective L3 stage, animals are highly motile and environmentally resistant. The infective L3 stage resembles the developmentally arrested dauer stage of *C. elegans*, discussed further below.

As indicated in the Background, a wide variety of plant and animal parasitic nematodes exist. As the term is used herein, parasitic nematodes are distinguished in that they must (1) undergo at least part of their life cycle (e.g., development, growth, and/or reproduction) within their respective host(s) and/or (2) obtain a significant proportion of their nutrition by feeding on a living organism to which they remain attached during at least a portion of their life cycle while remaining largely outside the organism and not internalizing the organism. This latter mode of parasitism is to be distinguished from the consumption of living organisms (e.g., bacteria) or the saprophytic behavior characteristic of free-living nematodes. Plant parasitic nematodes may be broadly classified as ectoparasites, which remain outside the plant host although they may insert part of their body (e.g., feeding stylet and/or feeding stylet and part of the body itself) into the plant, and endoparasites, which enter the plant (typically via the root) and may migrate therein. Animal parasitic nematodes (which include nematode parasites of humans) typically spend at least a portion of their life cycle within the body of the host. Detailed information regarding many of the known plant and animal parasites of importance may be found in Perry, R. N. and Wright, D. J. (eds.), *The Physiology and Biochemistry of Free-living and Plant-parasitic Nematodes*, CABI Publishing, New York, 1998, and in Anderson, R. C., *Nematode Parasites of*

*Vertebrates*, 2$^{nd}$ ed., CABI Publishing, New York, 2000, respectively, and references listed in these volumes.

Both animal and plant parasitic nematodes are known to possess secretory organs and to secrete a variety of products. The secretory pathway in nematodes appears to resemble that found in other eukaryotes. The process of protein secretion in eukaryotes, the components of the protein secretion pathway, and characteristic features of secreted proteins have been extensively studied. (See for example, Chapters 12 and 13 in Alberts, B., et al., *Molecular Biology of the Cell*, 3$^{rd}$. ed., Garland Publishing, New York, 1995; Sakaguchi, M., "Eukaryotic protein secretion", *Curr. Op. in Biotech.*, 8: 595–601, 1997, and references therein.) Briefly, polypeptides destined for secretion typically contain a sorting signal referred to as a signal sequence or signal peptide that targets them for the endoplasmic reticulum (ER) membrane. Within the ER secretory proteins may associate with a variety of proteins that facilitate their proper folding and/or assembly, e.g., chaperones. In addition, secretory proteins may be modified (e.g., glycosylated) within the ER. Proteins destined for secretion are transported from the ER through the Golgi apparatus via transport vesicles and are ultimately transported to the cell surface via transport vesicles that bud from the Golgi apparatus. These vesicles fuse with the plasma membrane, typically though not necessarily in response to an extracellular signal, and release their contents to the exterior in the process known as exocytosis. Vesicular transport is mediated by a variety of GTP-binding proteins, particular members of the monomeric GTPase family. Secreted proteins may undergo modifications (e.g., glycosylation, proteolytic cleavage, etc.) during various stages of the secretory pathway. Proteolytic cleavage includes removal of the signal peptide, so that the form of the protein that is eventually secreted typically no longer contains the signal peptide. In addition to proteins, secretory granules may contain a variety of other secretory products, e.g., lipids, small molecules, etc.

Considerable evidence suggests that in both plant and animal parasitic nematodes secretory products play important roles in parasitism. Plant parasitic nematodes typically utilize evolutionarily adapted structures such as stylets and feeding tubes to inject secretions into the parasitized plant cell and to obtain nutrients from the plant cytoplasm (Hussey, R. S. Disease-inducing secretions of plant parasitic nematodes, *Annu Rev Phytopathol*, 27, 123–141, 1989; Hussey, R. S., Grundler, F. M. W., Nematode parasitism of plants, in *The Physiology and Biochemistry of Free-living and Plant-parasitic Nematodes*, Perry, R. N and Wright, D. G., (eds.), Wallingford: CAB International, pp. 213–243, 1998; Sijmons, P. C., Atkinson, H. J., Wyss, U., Parasitic strategies of root nematodes and associated host cell responses. *Annu Rev Phytopathol* 32, 235–259, 1994.) Secretions may also be deposited outside the plant cell plasma membrane, where they may interact with membrane receptors. The major sources of secretions involved in plant parasitism by tylenchid nematodes are three pharyngeal secretory gland cells, one dorsal and two subventral, each of which is a single large cell connected to the pharyngeal lumen through an elaborate valve. In root-knot and cyst nematodes, these pharyngeal glands undergo dramatic morphological changes in secretory activity during parasitism, producing secretions thought to function in host penetration, induction and maintenance of feeding cells (plant cells from which the parasite withdraws nutrients, which frequently exhibit significant changes in metabolism and phenotype in response to parasitism), formation of feeding tubes (tube-like structures actually formed at least in part from secretions released into the plant cell from the stylet), and food digestion. In particular, secretions from the dorsal pharyngeal gland have long been considered to be critical for pathogenesis (Hussey, R. S., *Annu Rev Phytopathol*, 27, 123–141, 1989; Hussey, R. S., Grundler, F. M. W., Nematode parasitism of plants, in *The Physiology and Biochemistry of Free-living and Plant-parasitic Nematodes*, Perry, R. N and Wright, D. G., (eds.) (Wallingford: CAB International), pp. 213–243, 1998, Williamson, V. M., Hussey, R. S., Nematode pathogenesis and resistance in plants, *The Plant Cell*, 8, 1735–1745, 1996).

Ultrastructural studies have shown that plant nematode secretory products synthesized in both types of gland cells are packaged in spherical, Golgi-derived, membrane-bound granules, which are released from the gland cell into the pharyngeal lumen. These granules typically contain a number of different molecules destined for export. Following entry into the pharynx, secretions may pass anteriorly (e.g., through the stylet into the plant) and/or pass posteriorly into the intestine. While the role of the pharyngeal glands in nematode secretion has been extensively documented, there is also evidence that amphidial gland cells are also sources of nematode secretions (Bird, A. F. and Bird, J. *The Structure of Nematodes*, 2nd edition, Academic Press, Inc., San Diego, 1991). Amphids are sensory organs in communication with the exterior via a pore, and include neuronal cells as well as supporting cells referred to as amphidial gland cells in parasitic nematodes and amphid sheath cells in *C. elegans*.

Several plant parasitic nematode genes encoding specific secretory products have been characterized. For example, cellulase genes (specifically β-1,4-endoglucanases) have been cloned from two species of plant-parasitic cyst nematodes (deBoer, J. M., et al., Secretory granule proteins from the subventral esophageal glands of the potato cyst nematode were identified by monoclonal antibodies to a protein fraction from second-stage juveniles, *Mol. Plant Microbe Interact.*, 9, 39–46, 1996) and shown to be expressed in the subventral pharyngeal gland, primarily in the migratory stages (deBoer, J. M., et al., *Mol. Plant Microbe Interact.*, 12(8): 663–9, 1999). The genes contain signal sequences (sequences that are well known in the art to target polypeptides for entry into the secretory pathway), and the gene products are present in stylet secretions and have been detected within root cells (deBoer, et al., *Mol. Plant Microbe Interact.*, 12(1): 64–7, 1999). Cellulases are produced chiefly during the mobile stages of the nematode life cycle, during which they may facilitate penetration of the plant cell by causing enzymatic softening of the cell wall.

A cDNA encoding a cellulose-binding protein (Mi-cbp-1) including a putative signal sequence has been cloned from the root-knot nematode *Meloidogyne incognita*, and the protein has been identified in stylet secretions (Ding X, et al., A secretory cellulose-binding protein cDNA cloned from the root-knot nematode *Meloidogyne incognita*, *Mol Plant Microbe Interact*, 11:952–9, 1998). Differential screening of a cDNA library constructed from the esophageal gland region of the root-knot nematode *Meloidogyne javanica* identified a gland-specific gene that encodes a potentially secreted chrorismate mutase enzyme whose primary substrate is found within plant cells, suggesting that the enzyme is likely secreted into the host cell cytoplasm (Lambert, K N, et al., Cloning and characterization of an esophageal-gland-specific chorismate mutase from the phytoparasitic nematode *Meloidogyne javanica*. *Mol Plant Microbe Interact.*, 12:328–36, 1999).

Secretory products are also important for infection and development of animal parasitic nematodes. For example, infective larvae of the hookworm *Ancylostoma caninum* secrete proteins when activated by host serum to resume feeding behavior, a physiological response that has been established as an in vitro model of the transition to parasitism (Hawdon J. M., Hotez P. J., Hookworm: developmental biology of the infectious process, *Curr Opin Genetics Dev* 6, 618–623, 1996; Hawdon J. M., Schad G. A., Serum stimulated feeding in vitro by third-stage infective larvae of the canine hookworm *Ancylostoma caninum. J Parasitol* 76, 394–398, 1990). The predominant secreted product released by activated infective larvae is a 42-kDa protein named ASP-1, for *Ancylostoma* secreted protein, which is homologous to the venom allergen antigen 5 family from *Hymenopteran* insects (Hawdon J. M., Jones B. F., Hoffman D. R., Hotez P. J., Cloning and characterization of *Ancylostoma*-secreted protein, *J Biol Chem* 271, 6672–6678, 1996). Immunostaining suggests that ASP-1 may be produced in the amphidial gland cells.

Venom allergen (VA) homolog cDNAs have since been isolated from most major nematode groups, including all of the important animal and plant parasitic orders thus far examined and, like ASP-1, appear to be abundantly represented in the infective larval stages (Blaxter M. L. et al, Genes expressed in *Brugia malayi* infective third stage larvae, *Mol Biochem Parasitol* 77, 77–93, 1996). For example, a VA homolog, MSP-1, has been cloned from an *M. incognita* differential expression library, indicating that the protein is up-regulated following the onset of parasitism (Ding, X., Allen, R. I., Hussey, R. S., Cloning secretion genes from *Meloidogyne incognita* using RNA fingerprinting, *J. Nematol.*, 29, 575, 1997). Table 1 presents a representative selection of VA proteins found in various nematode species. The fact that VA proteins are expressed in infective stage and adult nematode parasites is highly suggestive of a role in parasitism, e.g., in feeding, digestion, molting, immune evasion, or other processes. Further evidence that these proteins are important in nematode parasitism derives from the fact that immunologically blocking certain nematode VA proteins results in host protection in

TABLE I

Nematode Venom Allergen Proteins

| Name | Species | Nematoda order | GenBank acc.# | #aa |
|---|---|---|---|---|
| VAP-1 | *Caenorhabditis elegans* | Rhabditida | AF112356 | 425 |
| Hg-VAP-1 | *Heterodera glycines* | Tylenchida | AF374388 | 215 |
| Hg-VAP-2 | *Heterodera glycines* | Tylenchida | AY033601 | 212 |
| ASP-1 | *Ancylostoma caninum* | Strongylida | U26187 | 424 |
| ASP-2 | *Ancylostoma caninum* | Strongylida | AAC35986 | 204 |
| Na ASP-1 | *Necator americanus* | Strongylida | AAD13340 | 424 |
| Hc40 | *Haemonchus contortus* | Strongylida | AF047417 | 459 |
| Hc24 | *Haemonchus contortus* | Strongylida | U64793 | 222 |
| Ov VA | *Onchocerca volvulus* | Spirurida | AF042087 | 220 |
| Wb VA | *Wuchereria bancrofti* | Spirurida | AF109794 | 220 |
| Bm VA | *Brugia malayi* | Spirurida | AF042088 | 220 |
| Di VA | *Dirofilaria immitis* | Spirurida | AF001100 | 221 |
| MSP-1 | *Meloidogyne incognita* | Tylenchida | AF013289 | 231 |
| Tc-vah-1 | *Toxocara canis* | Ascaridida | AI083044 | 474 |
| Tc-vah-2 | *Toxocara canis* | Ascaridida | AI083048 | 461 | animals. Immunization of mice and sheep with recombinant VA proteins ASP-1 and Hc24, respectively, protects them from challenge infection with infective larvae (Ghosh K., Hawdon J. M., Hotez P. J., Vaccination with alum-precipitated recombinant *Ancylostoma*-secreted protein 1 protects mice against challenge infections with infective hookworm (*Ancylostoma caninum*) larvae *J Infect Dis* 174, 1380–1383, 1996). In addition, the release of ASP-1 and resumption of larval hookworm development are blocked by the exogenous compound 4,7-phenanthroline (Hawdon J M, Jones B F, Hoffman D. R., Hotez P. J., Cloning and characterization of *Ancylostoma*-secreted protein, *J Biol Chem* 271, 6672–6678, 1996), indicating that chemical antagonists can simultaneously block secretion and parasitic nematode development. A variety of compounds can induce secretion of pharyngeal gland proteins in parasitic nematodes, indicating that the nematode secretory machinery is sensitive to externally applied chemicals (Jones J. T., Robertson W. M., "Nematode Secretions" in *Cellular and Molecular Aspects of Plant-Nematode Interactions*, Fenoll C, Grundler F M W, Ohl S A, eds., Dordrecht: Kluwer, pp. 98–106, 1997).

In addition to members of the VA protein family, a number of additional secretory products have been identified from various animal parasitic nematodes. For example, *A. caninum* third stage larvae have been demonstrated to release metalloproteases when stimulated to feed in vitro (Hawdon, J. M., et al., *Exp. Parasitol.*, 80(2): 205–11, 1995). Various other excretory/secretory proteins from several hookworm species have been described, including hyaluronidases, as well as cysteine, aspartyl, and serine proteases (See, for example, Hawdon, J. M. and Hotez, P. J., *Curr. Op. Genet. Dev.*, 6: 618–623, 1996, and references 4 and 28–33 therein.). Furthermore, cDNAs encoding two putative excretory/secretory proteins have been cloned from *H. contortus*, and the corresponding mRNA has been shown to be expressed primarily or only in the parasitic life stages (Schallig, H. D., et al., *Mol. Biochem. Parasitol.*, 88(1–2): 203–13, 1997). See also PCT/AU89/00416, WO98/01550, WO92/13889, and U.S. Pat. No. 5,948,644.

B. *C. elegans* as a Model System for Parasitic Nematodes

Molecular genetic methods (such as gene knockouts, transgenic animals, etc.) can uncover the biological function of individual genes and proteins in an organism, information that can form the foundation for developing target-based compound discovery screens. However, at present these methods are difficult to perform in parasitic nematodes. In contrast, such procedures can be performed in a straightforward manner in *C. elegans*. Furthermore, the complicated life cycle of many parasitic nematodes and their need for a suitable plant or animal host makes it inconvenient to propagate them in the laboratory.

Over the past twenty-five years extensive study of *C. elegans* has led to its recognition as a pre-eminent "small metazoan" model for understanding the development, neurobiology, and genetics of more complex animals (Riddle D. L., Blumenthal T., Meyer B. J., Priess J. R., *C. elegans II*, Cold Spring Harbor: Cold Spring Harbor Laboratory Press, 1997; Wood W. B., *The Nematode Caenorhabditis elegans*, Cold Spring Harbor: Cold Spring Harbor Laboratory Press, 1988). The strengths of the *C. elegans* model include: rapid reproduction (four days), a transparent body that allows observation and identification of each cell in live animals, a completely delineated developmental cell lineage and neural anatomy, and the first fully sequenced genome of a multicellular organism. Rapid and powerful techniques for generating and isolating genetic mutants, mapping mutations, cloning genes, and creating transgenic *C. elegans* are all well known in the art and can be accomplished in a much shorter time period (weeks to months) than in most other metazoan model systems. Moreover, *C. elegans* is readily cultured both on Petri dishes containing *E. coli* as food and in liquid culture. As described further below, this last property makes this nematode eminently adaptable for arraying and assaying in microtiter plates and suitable for high-throughput chemical screening against thousands of compounds simultaneously (Link, E. M., Hardiman G., Sluder, A., Johnson, Carl D., and Liu L. X., Therapeutic target discovery using *Caenorhabditis elegans, Pharmacogenomics* 1(2), 2000).

In the last decade, numerous avenues of research into the fundamental mechanisms of organismal growth, development, and behavior utilizing different model organisms have converged, in no small part due to rapidly accumulating DNA sequence information and computational biology resources such as those developed by the *C. elegans* Sequencing Consortium (*C. elegans* Sequencing Consortium T, Genome sequence of the nematode *C. elegans*: a platform for investigating biology, *Science* 282, 2012–2018, 1998). For example, the majority of human genes (as extrapolated from the set of positionally cloned human disease genes) have *C. elegans* homologs defined by standard sequence comparison algorithms (Bassett D. E., Jr. et al, Genome cross-referencing and XREFdb: implications for the identification and analysis of genes mutated in human disease, *Nat Genet* 15, 339–344, 1997). In fact, individual proteins, cellular structures and regulatory pathways are often conserved among evolutionarily divergent species such as yeast, fruit flies, nematodes, mice, and humans. Thus, cross-genomic studies of such fundamental biological processes as the cell cycle, the ras pathway, and apoptosis have demonstrated that structurally homologous genes are often functionally homologous as well, i.e. perform the same genetic and biochemical function across species. For this reason, targets and pathways that are conserved between *C. elegans* and other organisms can be used, for example, as a model for human disease (Ahringer J., Turn to the worm. *Curr Opin Genetics Dev* 7, 410–415, 1997) or as a platform for pharmaceutical discovery (Gil E., Link E. M., Liu L. X., Johnson C. D., Lees J. A., Regulation of the insulin-like developmental pathway of *Caenorhabditis elegans* by a homolog of the PTEN tumor suppressor gene, *Proc Natl Acad Sci USA* 96, 2925–2930, 1999). As described herein such targets and pathways can be used as the basis for screens for the identification of new anti-nematode compounds.

While many *C. elegans* genes are homologous to those of humans and other vertebrates, *C. elegans* genes are much more similar to those of parasitic nematode species as judged by comparison with sequences available in sequence databases. Beyond such sequence similarities, basic mechanisms controlling development and behavior are likely to be shared between *C. elegans* and parasitic nematodes, in spite of life histories and survival strategies that superficially appear very different (Riddle D. L., Georgi L. L., Advances in research on *Caenorhabditis elegans*: application to plant parasitic nematodes, *Annu Rev Phytopathol* 28, 247–269, 1990). For example, the dauer larva of *C. elegans*, an alternative third-stage larva specialized for dispersal and long-term survival, bears numerous parallels to the obligatory infective stage larvae of nematode parasites (Hotez P, Hawdon J., Schad G. A., Hookworm larval infectivity, arrest and amphiparatenesis: the *Caenorhabditis elegans* daf-c paradigm. *Parasitology Today* 9, 23–26, 1993). Entry into the dauer stage can be triggered by crowding and starvation, and the genetic pathway underlying entry into and recovery from dauer have been extensively studied. The *C. elegans* genome sequence also contains a large number of apparently nematode-specific gene families (Sonnhammer E. L., Durbin R., Analysis of protein domain families in *Caenorhabditis elegans, Genomics* 46, 200–216, 1997), providing a rich source of potential nematode-selective biological targets for nematicide and anthelminthic discovery.

*C. elegans* contains five pharyngeal gland cells, three of them known collectively as g1 cells and two called g2 cells. The g1 cells are equivalent to the three pharyngeal gland cells found in plant parasitic nematodes and contain secretory vesicles (Bird, A. F. and Bird, J., 1991, referenced above). In addition, *C. elegans* possesses amphids, and *C. elegans* amphid sheath cells are believed to secrete matrix material that surrounds the neuron processes (Riddle, D. L. and Albert, P. S., Regulation of Dauer Larva Development, in *C. elegans II*, referenced above). In free-living nematodes, secreted proteins may include proteins unrelated to parasitism but important in general nematode physiology or development while in parasitic nematodes secreted proteins may also include proteins that play a role in parasitism.

While the many advantages of *C. elegans* described above make it a preferred organism for the practice of the present invention, the invention may also be practiced using a variety of other nematode species. In particular, the invention may be practiced using various free-living nematode species that can be propagated under laboratory conditions, e.g., *C. briggsae, C. remanei*, etc.

C. Aspects of the Invention (i) Nematode Secretory Pathway and Nematode Secretory Products The present invention provides screens for compounds capable of exerting an inhibitory activity on a nematode secretory pathway. In the context of the present invention, a nematode secretory pathway is a pathway that leads to the production and secretion of a secretory product, i.e., a compound that is produced within a cell and subsequently released into the extracellular environment. The extracellular environment may be external to the organism or internal to the organism. In preferred embodiments of the invention, nematodes producing the secretory product are grown in culture under conditions suitable for production of the secretory product. Thus, for example, if the secretory product is a protein, nematodes are grown in culture under conditions suitable for expression of the gene encoding the secreted protein. As mentioned above, in preferred embodiments of the invention the nematodes used for the screen are *C. elegans*, and the following description assumes that this is the case. In addition, in preferred embodiments of the invention the secretory product is a protein (i.e., a polypeptide), and unless otherwise stated the following description assumes that this is the case although the invention also encompasses screening for inhibitors of nematode secretory pathways that result in the secretion of molecules other than proteins (e.g., lipids, small molecules, carbohydrates, etc.).

According to one embodiment of the invention, nematodes growing in culture under conditions suitable for expression of the secretory protein are exposed to a test compound, and the secretory protein is detected using any appropriate method. A reduction in the level of the secretory protein during or following exposure to the test compound relative to the level of the secretory protein in the absence of the test compound indicates an inhibitory activity for the candidate compound. In certain embodiments of the invention the level of an RNA transcribed from a gene that encodes a secretory protein is detected. A reduction in the level of the RNA during or following exposure to the test compound relative to the level of the RNA in the absence of the test compound indicates an inhibitory activity for the candidate compound.

As will be appreciated by one skilled in the art and in light of the discussion of eukaryotic secretion provided in section A, a nematode secretory pathway (also referred to as a nematode secretion pathway) may involve some or all of a series of steps including, but not limited to, transcription of RNA from a gene encoding a secreted protein, processing of the RNA (e.g., splicing, polyadenylation, etc.), transport of the RNA from nucleus to cytoplasm, translation of the RNA into a protein, translocation of the protein across the endoplasmic reticulum membrane (which may occur co-translationally or post-translationally), folding, signal sequence cleavage, co- or post-translational processing (e.g., glycosylation), association or assembly of multimeric proteins, exit from the endoplasmic reticulum, entry into the Golgi apparatus, packaging of the secreted protein into secretory granules, transport of secretory granules, and fusion of secretory granules with the cell membrane. A nematode secretory pathway may also involve reception of an extracellular regulatory signal (e.g., a signal that stimulates secretion), signal transduction, etc. In general, a nematode secretory pathway may be inhibited by affecting any of the steps in the pathway. An inhibitor of a nematode secretory pathway is any compound (e.g., small molecule, lipid, carbohydrate, peptide, polypeptide, nucleic acid, etc.) that inhibits, either directly or indirectly, any step in a pathway leading to secretion of a secretory product, e.g., a secreted protein.

In general, any nematode secreted protein and/or any gene encoding such a protein may be detected in preferred embodiments of the present invention. Suitable proteins include, but are not limited to, proteins known in the art to be secreted by a parasitic nematode or homologs thereof. In certain preferred embodiments of the invention in which the inventive screen is performed in *C. elegans*, the protein is a *C. elegans* homolog of a protein secreted by a parasitic nematode. Examples of proteins secreted by parasitic nematodes include VA proteins, cathepsins, metalloproteases, etc., which are discussed further below. In certain preferred embodiments of the invention the protein is a *C. elegans* homolog of a protein secreted by a parasitic nematode during a parasitic phase of the nematode life cycle. Particularly preferred proteins are *C. elegans* homologs of proteins secreted primarily during a parasitic phase of the parasitic nematode life cycle and/or upregulated during a parasitic phase of the nematode life cycle.

In certain preferred embodiments of the invention the parasitic nematode can be a member of any of the following nematode orders: *Strongylida, Rhabditida, Ascaridida, Spirurida, Oxyurida, Enoplida, Tylenchida,* and *Dorylaimida*. In certain preferred embodiments the parasitic nematode is an animal parasite and is a member of a genus selected from the list of genera presented in Table 2 under the orders *Strongylida, Rhabditida, Ascaridida, Spirurida, Oxyurida,* or *Enoplida*. In certain preferred embodiments the parasitic nematode is a plant parasite and is a member of a genus selected from the list of genera presented in Table 2 under the orders *Tynlenchida* or *Dorylaimida* Other parasitic nematodes are also within the scope of the invention. References describing the phylogeny and classification of nematodes include, for animal parasitic nematodes: R C Anderson, *Nematode Parasites of Vertebrates,* 2nd ed., CAB International, 1992, and for plant-parasitic nematodes: V H Dropkin, *Introduction to Plant Nematology,* 2nd ed., Wiley, 1989.

TABLE 2

Parasitic Nematode Orders and Genera

| Order | Host | Common name or disease name | Phylogenetic family |
|---|---|---|---|
| Strongylida | | | |
| Haemonchus | ungulates | | |
| Oestertagia | sheep, cattle, goats | | |
| Trichostrongylus | cattle | | |
| Cooperia | cattle | | |
| Dictyocaulus | horses, ruminants | | |
| Strongylus | horse | | |
| Oesophagostomum | pigs, ruminants | | |
| Syngamus | poultry | | |
| Nematodirus | sheep, goats | | |
| Heligmosomoides | rodents | | |
| Nippostrongylus | rodents | | |
| Metastrongylus | pig | | |
| Angiostrongylus | humans | | |
| Ancylostoma | human | hookworm | |
| Necator | human | hookworm | |
| Uncinaria | dogs etc | dog hookworm | |
| Bunostomum | cattle hookworm | | |
| Rhabditida | | | |
| Strongyloides | human | | |
| Steinernema | insects | | |
| Ascaridida | | | |
| Ascaris | human | roundworm | |
| Parascaris | horses | | |
| Toxocara | dogs | | |
| Toxascaris | cats, dogs | | |

TABLE 2-continued

Parasitic Nematode Orders and Genera

| Order | Host | Common name or disease name | Phylogenetic family |
|---|---|---|---|
| Baylisascaris | raccoons | | |
| Anisakis | fish - human | | |
| Pseudoterranova | fish - human | | |
| Heterakis | poultry | | |
| Spirurida | | | |
| Wuchereria | human | elephantiasis | |
| Brugia | human | | |
| Onchocerca | human | river blindness | |
| Dirofilaria | dog | | |
| Loa | human | | |
| Thelazia | mammal, bird eyelid | | |
| Dracunculus | human | guinea worm | |
| Gnathostoma | human | | |
| Oxyurida | | | |
| Enterobius | human | | |
| Oxyuris | horses | | |
| Syphacia | human | | |
| Enoplida | | | |
| Trichinella | human | | |
| Trichuris | human | | |
| Capillaria | human | | |
| Tylenchida | | | |
| Globodera | plants | (potato) cyst nematode | Heteroderidae |
| Heterodera | plants | (soybean) cyst nematode | Heteroderidae |
| Meloidogyne | plants | root knot nematode | Heteroderidae |
| Anguina | plants, wheat | seed, stem & leafgall nematode | Tylenchidae |
| Ditylenchus | plants | potato rot nematode | Tylenchidae |
| Hirschmanniella | plants | rice root nematode | Pratylenchidae |
| Naccobus | plants | false rootknot nematode | Pratylenchidae |
| Pratylenchus | plants | lesion nematode | Pratylenchidae |
| Radopholus | plants | burrowing nematode | Pratylenchidae |
| Criconema | plants | ring nematode | Criconematidae |
| Tylenchulus | plants | citrus nematode | Tylenchulidae |
| Paratylenchus | plants | pin nematode | Paratylenchidae |
| Aphelenchus | plants | bud & leaf nematode | Aphelenchidae |
| Bursaphelenchus | plants | pinewood nematode | Aphelenchoididae |
| Dorylaimida | | | |
| Longidorus | plants | needle nematode | Longidoridae |
| Xiphinema | plants | dagger nematode | Longidoridae |
| Trichodorus | plants | stubby root nematode | Trichodoridae |
| Paratrichodorus | plants | stubby root nematode | Trichodoridae |

In certain preferred embodiments of the invention the protein is a *C. elegans* homolog of a parasitic nematode venom allergen (VA) protein. Such a homolog is referred to herein as a *C. elegans* VA protein. As described in more detail in Example 1, a cDNA encoding the *C. elegans* ortholog (structurally conserved reciprocal best homolog, defined in more detail below) of the *A. caninum* VA protein ASP-1, referred to as VAP-1, has been cloned, and over 20 homologs of VAP-1 have been identified in a BLAST search of the complete *C. elegans* genome. The closest homolog to the vap-1 gene is designated vap-2, which, like vap-1, encodes two VAP domains. The high degree of homology between vap-2 and vap-1 (and thus other VA genes) favor these genes for use in the inventive screens described herein. Thus in certain particularly preferred embodiments of the invention, a protein encoded by vap-1 or vap-2, or a marker for the expression of the vap-1 or vap-2 gene is detected. The *C. elegans* VA proteins are discussed in further detail in Example 2.

In certain preferred embodiments the protein is a *C. elegans* member of either the cathepsin B or L class of thiol proteases. The thiol proteases comprise an extensive family, members of which have been identified in a wide range of eukaryotic organisms. Cathepsin L-like activities have been identified in parasitic nematode excretory/secretory products (Caffrey C R and Ryan M F, *Vet Parasitol* 52: 285–96, 1994, and Rhoads M L and Fetterer R H, *J Parasitol* 81: 505–12, 1995). A cathepsin B-like protein has been identified in excretory/secretory products of the hookworm *A. caninum* and has been immunolocalized to their esophageal, amphidial and excretory glands (Harrop S A, Sawangjaroen N, Prociv P, and Brindley P J, *Mol Biochem Parasitol* 71: 163–71, 1995). A number of *C. elegans* genes with homology to members of the cathepsin B and cathepsin L subfamilies have been identified in the *C. elegans* genome sequencing project.

As mentioned above, the invention encompasses the detection of any nematode secretory product, preferably detection of a *C. elegans* homolog of a parasitic nematode secretory protein. Several specific products (secreted proteins or putative secreted proteins) have been described above, but the inventive methods encompass additional proteins including those not hitherto recognized as nematode secreted proteins. A variety of approaches known in the art may be used to identify proteins secreted by parasitic nematodes and/or genes that encode nematode secreted proteins. For the purposes of the present invention, a parasitic nematode secretory product includes, but is not limited to, any of the following: (1) a molecule that has been identified in a parasitic nematode secretion; (2) an expression product (e.g., a protein or an RNA) of a gene that is expressed in a parasitic nematode secretory cell, tissue, or organ (e.g., a gland), wherein the gene comprises a nucleotide sequence that encodes a signal peptide, or (3) a homolog of a protein found in a different species (e.g., a homolog having a BLASTP score of >80 or an approximately equivalent measure of homology) that has been shown to be secreted by that species. Additional evidence that can be used to determine whether a product is a putative nematode secretion product includes presence of an activity characteristic of the product (e.g., protease activity) in a nematode external secretion. Thus it is not a requirement of the invention that a parasitic nematode secretory product is actually identified in external secretory material. A product (either a polypeptide or a polynucleotide) is considered to be a putative nematode secretory product if it contains a signal peptide (in the case of a polypeptide) or encodes a signal peptide (in the case of a polynucleotide), where the signal peptide is identifiable as such using computer programs well known in the art intended for identification of signal sequences (By way of example and not limitation, see Ladunga, I., Large-scale predictions of secretory proteins from mammalian genomic and EST sequences, *Curr. Op. Biotech.*, 11:13–18, 2000, and references therein, and Nakai, K. and Kanehisa, M., "A knowledge base for predicting protein localization sites in eukaryotic cells", *Genomics*, 14(4):897–911, 1992, describing the PSORT program) and/or functional assays (e.g., assays that determine whether addition of the sequence is able to direct secretion of a normally nonsecreted protein) and preferably is expressed in a nematode secretory cell, tissue, or organ (e.g., a gland, amphid sheath cell, etc.). Specific approaches to identifying nematode secretory proteins are described in detail below, but it is to be understood that the practice of the invention is not limited to these approaches, and the invention encompasses nematode secretory products identified by other techniques known in the art.

(ii) Additional Methods for Identifying Candidate Parasitic Nematode Secretory Products As is well known in the art, certain parasitic nematode species can be cultured in vitro, at least for a portion of the life cycle, and in vivo culture systems for various parasitic nematodes also exist. Secreted fluid or culture medium from nematode cultures may be collected, preferably in the presence of appropriate protease inhibitors (such as serine protease inhibitors (e.g., PMSF), thiol protease inhibitors (e.g., leupeptin) and/or acidic protease inhibitors (e.g., pepstatin). Material secreted by nematodes in an infective and/or pathogenic stage of the life cycle may be a particularly preferred source of nematode secreted proteins (e.g., for the production of antibodies, for purification and subsequent microsequencing, etc.). In this regard, it is noted that signals that are associated with and/or stimulate the transition to parasitism in certain nematodes are known. For example, components in serum are known to stimulate free-living L3 larvae of the canine hookworm *Ancylostoma caninum* to resume feeding in vitro, and such resumption of feeding may be used as a marker for the transition to parasitism of developmentally arrested L3 larvae that occurs upon entry into the definitive host. Alternately, secreted proteins may be obtained by dissecting nematodes and isolating portions of the nematode containing secretory cells and/or organs, e.g., pharyngeal glands, amphid sheath cells, etc., and purifying proteins therefrom using standard techniques. Although at present no cell lines derived from nematode secretory cells, tissues, etc., exist, in the event that such cell lines are developed, the cell lines and/or culture medium in which such cell lines are propagated may be used as a source of secreted proteins.

The collected material may be subjected to centrifugation, e.g., to remove any tissue and/or cellular debris. The secreted protein(s) may then be concentrated using any standard procedure (e.g., filtration through an Amicon filter, or ammonium sulfate precipitation followed by centrifugation). The concentrated mixture may be fractionated in any of a variety of ways, although this is not required. For example, the mixture may be subjected to polyacrylamide gel electrophoresis and protein bands visualized (e.g., by Coomassie Blue staining, silver staining, etc.). Gel portions containing protein bands may then be isolated, and the proteins may be extracted from the gel. Fractionation of the mixture increases the likelihood that the resulting antiserum will contain antibodies that bind to only one or a few components of the mixture rather than a wide variety of antibody species, each of which may bind to a different component of the mixture.

Standard immunological techniques, such as those described in Harlow and Lane (Antibodies: A Laboratory Manual, Cold Spring Harbor Laboratory, New York, 1988) may then be employed to prepare polyclonal antiserum and/or monoclonal antibodies to the secreted protein(s). Briefly, one or more standard laboratory animals may be immunized with secreted protein(s) and polyclonal antiserum recovered. Hybridoma technology well known in the art may be used to prepare monoclonal antibodies. In certain circumstances it may be desirable, e.g., in order to improve the immune response in an animal to the secreted proteins, to couple the secreted proteins to an appropriate carrier protein and/or to effect limited protease digestion of the secreted protein(s) prior to immunizing the animal.

Other methods of producing antibodies that bind to nematode secretory proteins may also be used. For example, antibodies against the secretory protein fraction may be prepared by phage display technology. Such technology permits the selection, from an antibody fragment gene recombinant bacteriophage library prepared from natural or synthetic antibody gene repertoires, of bacteriophage expressing an antibody fragment against a particular antigen. For example, the secretory protein fraction may be used to screen an antibody fragment gene recombinant bacteriophage library. Clones identified can then be recovered, and antibody fragments produced by the bacteriophage clones can be expressed in bacteria, recovered and then employed, either individually or as a pool of antibody fragments, for the screening of the cDNA expression library. A variety of other display technologies known in the art can also be used. Display technologies are reviewed in FitzGerald, K., In vitro display technologies—new tools for drug discovery, *Drug Discovery Today*, 5:253–258, 2000, and references therein.

Once an antibody that binds to a nematode secreted protein has been produced, the antibody can be used to clone a nucleic acid encoding at least the portion of the secreted protein recognized by the antibody, e.g., by screening a cDNA expression library comprising cDNA from the nematode. Methods for producing expression libraries and for screening such libraries are well known in the art. (See, for example, Ausubel et al., eds., Current Protocols in Molecular Biology, John Wiley and Sons, Inc., New York, 1996.) U.S. Pat. No. 6,040,144 discusses methods known in the art for preparing mammalian gene expression libraries enriched for secreted proteins, for preparing secreted proteins and for generating polyclonal antiserum against such proteins in more detail, and certain of the procedures described therein may be adapted by the skilled artisan for use in the context of nematode secreted proteins. It may be preferable to screen an expression library prepared from secretory tissue (e.g., gland cells, amphid sheath cells, etc.) although any expression library from the organism could be used. It may be desirable to screen a stage-specific library (e.g., a library prepared from nematodes in an infective and/or pathogenic stage of the life cycle) although again this is not necessary.

Another approach to identifying protein components of nematode secretions involves collecting material containing nematode secretory proteins as described above, fractionating the material so as to obtain a substantially purified protein (e.g., by concentrating the material, subjecting the concentrated material to gel electrophoresis, visualizing protein bands by staining the gel, and excising visualized bands), and performing amino acid sequencing of the purified protein or fragments thereof. Prior to sequencing, the substantially purified protein can be cleaved (e.g., by digestion with trypsin or another appropriate enzyme), and the resulting fragments may be further purified (e.g., by HPLC). Amino acid sequencing may be performed using any of a variety of techniques known in the art. The amino acid sequence can be used to search sequence databases in order to identify the corresponding full length gene. Alternatively, e.g., in the case of organisms such as parasitic nematodes whose genome has not been fully sequenced, the amino acid sequence can be used to design degenerate oligonucleotide primers or probes, which may then be used to clone a gene or a portion thereof that encodes at least a portion of the secreted protein. For example, the probes may be used to screen a library (e.g., a cDNA or genomic library) produced using DNA isolated from the nematode, or the primers may be used in a PCR reaction to amplify a gene-specific product from a library produced using DNA isolated from the nematode or from cDNA or genomic DNA derived from the nematode. The product of the PCR reaction can be used to screen a library to identify additional portions of the gene, and techniques such as 5' RACE may be used to isolate further portions of the gene. (See, for example, Hawdon, et al., *J. Biol. Chem.*, 271, 6672–6678, 1996, which describes cloning of a gene encoding the *A. caninum* secreted protein ASP-1.)

An alternate approach to identifying genes that encode nematode secreted proteins involves identifying transcripts that are differentially expressed in secretory tissues, cells, organs, etc., i.e., transcripts that are present within secretory tissues, cells, or organs at a level which exceeds their average level within the organism as a whole. A number of approaches to the identification of transcripts that are differentially expressed in a tissue or cell(s) of interest are known in the art. For example, cDNA libraries may be constructed using RNA isolated from the tissue of interest (e.g., gland tissue, amphid sheath cells) to enrich for transcripts present in such tissue. Such libraries may be differentially screened, e.g., screened with a first probe comprising RNA or cDNA derived from the tissue of interest and screened with a second probe comprising RNA or cDNA derived from another tissue, from the entire organism, etc. Clones that preferentially hybridize to the probe derived from the tissue or cell(s) of interest are candidates for genes that are specific (to a greater or lesser extent) for the tissue or cell(s) of interest. This approach has been used to identify an esophageal-gland specific genes from the root-knot nematode *M. javanica* (Lambert, K., et al., *Molecular Plant-Microbe Interactions*, 12(4): 328–336, 1999). Additional methods for identifying differentially expressed genes include differential display, representational difference analysis, suppression subtractive hybridization, etc. These and other techniques are described, for example, in Soares, M, Identification and cloning of differentially expressed genes, *Curr. Op. Biotech.*, 8: 542–546, 1997; Kozian, D. and Kirschbaum, B., Comparative gene-expression analysis, *Trends Biotechnol.*, 17(2):73–8, 1999, and references therein.

The sequence of genes identified as described above may be analyzed for features such as a region encoding a signal sequence, the presence of which may indicate that the gene encodes a secreted protein. Various computer programs known in the art exist to facilitate the identification of such regions. The sequence of the encoded protein may also be compared with sequences of proteins known to be secreted. Homology to known secreted proteins suggests that the protein encoded by the gene is secreted. To confirm that a protein encoded by a gene identified as described above is a secreted protein, an antibody that binds to the protein can be generated. The antibody can be produced by various methods well known in the art. For example, the antibody can be raised against a partial or full length protein produced in vitro (e.g., in *E. coli*, yeast, insect, mammalian or other host cells) using recombinant DNA technology, or the antibody can be raised against one or more peptides that form a portion of the candidate protein. The antibody can be used to localize the protein within an intact organism (e.g., by immunolocalization) and/or to determine which tissues or organs within the organism contain the protein (e.g., by performing immunoblotting on samples obtained from isolated tissues or organs).

Candidate nematode secretory proteins can also be identified based solely on homology to proteins known to be secreted in other organisms, including various non-nematode parasites. In the case of certain of these parasites, the importance of secreted proteins for parasitism has been clearly established. For example, *Toxoplasma gondii* produces a variety of secretory proteins that play roles in infection as do various other parasites (Carruthers, V. B., Armed and dangerous: *Toxoplasma gondii* uses an arsenal of secretory proteins to infect host cells, *Parasitol, Int.*, 48, 1–10, 1999; Ngo, H., et al., Differential sorting and post-secretory targeting of proteins in parasitic invasion, *Trends Cell Biol*, 10, 67–72, 2000, and reference therein). Parasitic nematode homologs of proteins secreted by non-nematode organisms, particularly non-nematode parasites, may be identified by searching databases containing parasitic nematode sequence information. Projects to sequence the genomes and projects to identify ESTs and GSTs are currently under way for a number of parasitic nematodes (Several of these are discussed, for example, in Blaxter, M., Parasitic helminth genomics. Filarial Genome Project. *Parasitology*, 118 Suppl:S39–51, 1999; Blaxter, M., Genes and genomes of *Necator americanus* and related hookworms, *Int J Parasitol*, 30(4):347–55, 2000; Unnasch, T R, et al., The genomes of *Onchocerca volvulus*, *Int. J Parasitol*, 30(4): 543–52, 2000; Williams, S A, et al., The filarial genome project: analysis of the nuclear, mitochondrial and endosymbiont genomes of *Brugia malayi*, *Int J Parasitol*, 30(4):

411–9, 2000. The invention encompasses the searching of databases including sequence information generated by various parasite genome and EST sequencing projects to identify open reading frames encoding putative secreted proteins. Databases containing genome and sequence information (in addition to general databases such as Genbank, EMBL,etc.) exist for a wide variety of parasites including parasitic nematodes and may be accessed at the Web site having URL: www.ebi.ac.uk/parasites/parasitegenome.html. Such homologs may represent candidate parasitic nematode secreted proteins.

Once a candidate parasitic nematode secreted protein or a gene encoding a candidate secreted protein is identified in a homology-based search, confirmation that the protein is secreted may, if desired, be obtained in a variety of ways. For example, the mRNA expression pattern of the gene can be obtained (e.g., by in situ hybridization, by performing Northern blots on tissues obtained from different nematode tissues or organs, etc.) Expression of the gene within a nematode secretory organ (e.g., a pharyngeal gland cell or an amphid sheath cell) suggests that the encoded protein may be secreted.

Alternately, an antibody that binds to the candidate secreted protein can be produced. The antibody can then be used to detect the protein within nematode secretory cells or organs (e.g., using immunolocalization techniques) and/or within nematode secretions (e.g., by immunoblotting) to confirm that the protein is secreted.

(iii) Identifying *C. elegans* Homologs of Candidate Parasitic Nematode Secretory Products Once a candidate or putative secreted protein produced by a parasitic nematode and/or a gene encoding such a protein is selected, homologous protein(s) and/or gene(s) from *C. elegans* may be identified using any of a variety of approaches. Since the entire *C. elegans* genome has been sequenced, and since databases containing the genomic sequence and sequences of proteins predicted to be encoded by open reading frames, cDNAs, expressed sequence tags, etc., are publicly available, a straightforward approach is to search such databases for *C. elegans* proteins, or fragments thereof, homologous to the selected parasitic nematode secreted protein. Databases suitable for searching include GenBank (available at www.ncbi.nlm.nih.gov/Genbank), SwissProt (available at www.ebi.ac.uk/swissprot), WormPep, and databases containing *C. elegans* ESTs and *C.elegans* genomic sequence (available at www.wormbase.org).

A number of computer programs employing various algorithms may be used to identify *C. elegans* protein(s) homologous to a parasitic nematode secreted protein. Appropriate programs include, among others, FASTA or BLASTN for nucleotide sequences and FASTA, BLASTP, gapped BLAST, and PSI-BLAST for amino acid sequences. FASTA is described in Pearson, W R and Lipman, D J, *Proc. Natl. Acad. Sci, USA*, 85, 2444–2448, 1988. BLASTP, gapped BLAST, and PSI-BLAST are described in Altschul, S F, et al., Basic local alignment search tool, *J. Mol. Biol.*, 215(3): 403–410, 1990, Altchul, S F and Gish, W, *Methods in Enzymology*, 266, 460–480, 1996, and Altschul, S F, et al., "Gapped BLAST and PSI-BLAST: a new generation of protein database search programs", *Nucleic Acids Res.* 25:3389–3402, 1997.

Although searching sequence databases is a convenient means of identifying *C. elegans* homologs of parasitic nematode secreted proteins and genes, other methods for identifying homologous *C. elegans* proteins and genes are also within the scope of the invention. For example, libraries produced using *C. elegans* genomic DNA or cDNA derived from *C. elegans* can be screened (typically under conditions of reduced stringency) using a probe derived from a gene encoding a parasitic nematode secreted protein.

As is well known in the art, many genes and their encoded proteins are members of families. Thus there may be multiple *C. elegans* genes homologous to a gene encoding a parasitic nematode secreted protein. In general, two homologous genes from different species may be related in two ways. Two genes that derive directly from a single gene in the last common ancestor of the two species are known as orthologs, while gene duplication events within an evolutionary lineage produce multiple homologous genes referred to as paralogs. If the duplication occurred in a common ancestor of the two species, each paralog in one species will have an ortholog in the other (provided no genes have been lost). However, if one or more duplication events took place after the evolutionary divergence of the two species, there may be no definitive orthologous relationships among the paralogous genes. Further discussion and definition of the term "ortholog" may be found, for example, in Tatusov R L, Mushegian A R, Bork P, Brown N P, Hayes W S, Borodovsky M, Rudd K E, Koonin E V, Metabolism and evolution of *Haemophilus influenzae* deduced from a whole-genome comparison with *Escherichia coli.*, *Curr Biol.* March 1;6(3):279–91, 1996.

In certain embodiments of the invention, in cases in which multiple *C. elegans* genes homologous to a particular parasitic nematode gene encoding a secretory product exist, it may be desirable to identify the *C. elegans* ortholog of the parasitic nematode gene and the corresponding *C. elegans* secretory product for performance of the inventive screens described herein. Several approaches to identifying an ortholog can be used. For example, a BLAST search of the *C. elegans* genome sequence using the parasitic nematode gene of interest can be used to identify the most similar *C. elegans* sequence, and the *C. elegans* sequence so identified can then be used to perform a reciprocal BLAST search of available sequence from the parasitic nematode. If the two sequences are orthologous, this search should detect the starting parasitic nematode gene as the most similar parasitic nematode gene (for that particular parasitic nematode species). Approaches to identifying orthologs are described, for example, in Mushegian A R, Garey J R, Martin J, Liu L X., Large-scale taxonomic profiling of eukaryotic model organisms: a comparison of orthologous proteins encoded by the human, fly, nematode, and yeast genomes, *Genome Res.*, June;8(6):590–8, 1998, in Sluder, A., et al., The nuclear receptor superfamily has undergone extensive proliferation and diversification in nematodes, *Genome Res.*, 9: 103–120, 1999, and references therein. According to one approach, to distinguish candidate orthologs from paralogs based on sequence similarity, two measures are applied, the BLASTP similarity score and the percentage of amino acid identity in the aligned segments. Criteria used to define candidate orthologs (Tatusov et al.,1996) are as follows. First, protein A in proteome a is a candidate ortholog of protein B in proteome b, if protein B is the best match when sequence A is searched against proteome b, and, conversely, protein A is the best match when sequence B is searched against proteome a. Second, A and B share similarity along their whole lengths (except for the rare case of domain fusion in single-copy multifunctional enzymes). Third, no homolog in a taxonomic outgroup (yeast in the present analysis) is closer to A than B, or closer to B than A. Computer programs such as CLUSTAL W (Thompson, J D, et al., "CLUSTAL W:

Improving the sensitivity of progressive multiple sequence alignment through sequence weighting, position-specific gap penalties, and weight matrix choice", *Nucleic Acids Res.* 22:4673–4680, 1994) are useful for performing alignments of multiple sequences and assessing relationships between them.

In certain preferred embodiments of the invention the *C. elegans* protein exhibits a significant degree of similarity to the selected parasitic nematode secreted protein. The degree of similarity can be determined using a variety of approaches and can take into consideration both the degree of identity between two sequences (preferably allowing for gaps) and the existence of conservative substitutions, i.e., positions at which two amino acid sequences differ but where the two amino acids exhibit similar biochemical characteristics with respect to size, charge, polarity, etc. Examples of conservative substitutions are well known in the art. See, for example, *Biochemistry,* 4th Ed., Stryer, L., et al., W. Freeman and Co., 1995 and U.S. Pat. No. 6,015,692. In certain preferred embodiments of the invention, when aligned so as to produce maximum similarity while allowing for gaps, at least 25% of the amino acid residues in the shorter of the two of the parasitic nematode secreted protein and the *C. elegans* homolog are similar to the corresponding (aligned) residue in the other protein, where a first amino acid residue is similar to a second amino acid residue if it is either identical to the second residue or if a substitution of the second amino acid for the first (or vice versa) is a conservative substitution. In certain preferred embodiments of the invention the foregoing criteria are met with respect to at least 30% of the amino acid residues. In certain preferred embodiments of the invention the foregoing criteria are met with respect to at least 40%, at least 50%, at least 60%, or at least 70% of the amino acid residues. As is well known in the art, significant homologies may extend over only a portion of the homologous proteins rather than over the full length of either protein. Thus in certain embodiments of the invention the *C. elegans* protein exhibits a significant degree of similarity to the selected parasitic nematode secreted protein over one or more portions of the sequence. For example, in certain preferred embodiments of the invention, when aligned so as to produce maximum similarity while allowing for gaps, at least 50% of the amino acid residues in the parasitic nematode secreted protein and the *C. elegans* homolog are similar to the corresponding (aligned) residue in the other protein over a domain at least 20 amino acids in length. In more preferred embodiments the foregoing criteria are met with respect to at least 60%, at least 70%, at least 80%, or at least 90% of the amino acids over a domain at least 20 amino acids in length. In yet more preferred embodiments of the invention the length of the domain over which the nematode secreted protein and the *C. elegans* homolog exhibit such similarity is at least 30 amino acids, at least 50 amino acids, at least 75 amino acids, at least 100, at least 150, or at least 200 amino acids in length. The foregoing discussion providing various methods of determining whether two proteins display significant homology is intended to be illustrative and should not be considered to be limiting. In general, one of ordinary skill in the art will be able to determine whether two proteins display sufficient similarity to be considered homologs of one another.

Various computer programs mentioned above provide an indication of the similarity between homologous sequences. For example, the BLAST programs mentioned above provide a score that reflects the degree of homology and also provide value referred to as an E value for each sequence identified as homologous to the input sequence. The E value represents the number of alignments with an equivalent or greater score that would be expected to occur purely by chance, and therefore alignments with a low E value are likely to be significant. Thus in certain preferred embodiments of the invention the alignment between a parasitic nematode secreted protein and a homologous *C. elegans* has an E value of less than 0.001, and yet more preferably less than 0.0001. In certain preferred embodiments of the invention a homologous *C. elegans* protein has a score of at least 80 when compared with the corresponding parasitic nematode protein using the BLASTP program (assuming default parameters).

To facilitate the practice of certain of the inventive methods described herein, once an open reading frame encoding a *C. elegans* homolog of a selected parasitic nematode secreted protein is identified (e.g., by database searching), it may be desirable to clone a cDNA encoding the protein. In addition to allowing manipulation using recombinant DNA techniques, cloning a cDNA confirms, for example, that an open reading frame predicted to encode a *C. elegans* homolog of a parasitic nematode secreted protein is actually expressed in the organism. Methods for cloning cDNAs are well known in the art. For example, oligonucleotide primers can be designed based on the sequence of the open reading frame and used to amplify a portion of *C. elegans* genomic or cDNA, which can then be used to probe a *C. elegans* CDNA library as described in more detail in Example 1. Various other approaches to cloning cDNAs are well known in the art.

In certain embodiments of the invention it is desirable to confirm that the selected *C. elegans* protein is expressed in *C. elegans* secretory cells, tissues, organs, etc. and/or that the selected protein is secreted. Although in preferred embodiments of the invention the *C. elegans* protein is secreted into the external environment (e.g., into culture medium), detection of the protein in the external enviroment is not a requirement of the invention. Determining whether a particular *C. elegans* protein is secreted can be done as described above for parasitic nematode secreted proteins (e.g., using immunoblotting). In addition, reporter genes comprising a regulatory element from a gene that encodes a putative secreted protein operably linked to a detectable marker can be used to monitor secretion, as described in more detail in a subsequent section of this document.

In certain embodiments of the invention it is desirable to determine the effect(s) of reducing or eliminating expression of the gene encoding the selected *C. elegans* protein. Identifying the phenotype of a loss-of-function or reduction-in-function mutant in such a gene may suggest additional methods of screening. For example, if reducing or eliminating expression of the gene encoding the selected *C. elegans* protein is lethal, then the inventive screen for inhibitors of secretion can comprise screening for lethality. As another example, if reducing or eliminating expression of the gene encoding the selected *C. elegans* protein causes a defect in movement, then the inventive screen for inhibitors of secretion can comprise screening to identify compounds that result in such a movement defect. In general, any phenotype, preferably an easily scorable phenotype, associated with loss-of-function or reduction-in-function of the selected gene may be used in the inventive screen. As will be appreciated by one of ordinary skill in the art, phenotypes such as lethality, movement defects, etc., may be caused through any of a variety of mechanisms, many of which are likely to be unrelated to secretory pathways. Therefore, a screen for such a phenotype may serve as a primary screen, and in preferred embodiments a secondary screen, in which compounds identified in the primary screen are evaluated for their effects on secretion, is performed. Such a secondary screen may use any of the approaches discussed herein for evaluating the effects of a compound on a nematode secretory pathway.

Methods for determining the phenotype associated with loss-of-function or reduction-in-function of a gene in *C. elegans* are well known in the art. Briefly, such methods involve, for example, creating a deletion mutant in which some or all of the gene is absent as described, for example, in Liu, L., et al., High-Throughput Isolation of *Caenorhabditis elegans* Deletion Mutants, *Genome Research*, 9:859–867, 1999. Of course other methods may be used to generate *C. elegans* strains having a mutation in a gene of interest. Such methods include, but are not limited to, transposon-mediated mutagenesis (described, for example, in Plasterk, R., "Reverse Genetics" in Methods in Cell Biology, Vol. 48, cited above).

Another approach to determining the phenotype associated with loss-of-function or reduction-in-function of a gene of interest is known as double-stranded RNA interference (RNAi). Double-stranded RNA (dsRNA) corresponding to a gene of interest is introduced into worms either by injection, by feeding them bacteria engineered to express the dsRNA, or by soaking them in a solution containing the dsRNA (though the latter method is generally less efficient). In general, RNAi results in progeny that lack expression of the corresponding gene product, allowing a determination of the loss-of-function phenotype. These methods are described, for example, in PCT application WO99/32619, in Fire, et al., Potent and specific genetic interference by double-stranded RNA in *Caenorhabditis elegans*, *Nature*, 391:806–11, 1998, and in Fraser, et al., Functional genomic analysis of *C. elegans* chromosome I by systematic RNA interference, *Nature*, 408:325–330, 2000.

The sections above have described methods for identifying and selecting parasitic nematode secreted proteins and genes encoding such proteins and have also described methods for identifying and selecting *C. elegans* homologs of parasitic nematode secreted proteins and genes encoding such proteins. Although in preferred embodiments of the invention the *C. elegans* protein is homologous to a parasitic nematode secreted protein, any *C. elegans* secreted protein can be used regardless of whether a homolog in a parasitic nematode species has been identified. Preferred *C. elegans* proteins include proteins expressed in secretory cells, tissues, organs, etc., e.g., proteins expressed in *C. elegans* dorsal or pharyngeal gland cells or armphid sheath cells. Secreted *C. elegans* proteins may be identified using any of the approaches discussed above for the identification of parasitic nematode secreted proteins.

In summary, for the purposes of the present invention, a *C. elegans* secretory product includes, but is not limited to, any of the following: (1) a molecule that has been identified in a *C. elegans* external secretion; (2) an expression product (e.g., a protein or an RNA) of a gene that is expressed in a *C. elegans* secretory cell, tissue, or organ (e.g., an amphidial or pharyngeal gland cell), wherein the gene comprises a nucleotide sequence that encodes a signal peptide. Thus it is not a requirement of the invention that a *C. elegans* secretory product is actually identified in external secretory material although this is preferred. Appropriate *C. elegans* secretory products include the following: (1) *C. elegans* homologs of parasitic nematode secretory products whose presence in external secretions has been demonstrated; (2) *C. elegans* homologs of putative parasitic nematode secretory products whose presence in external secretions has not been demonstrated, such as parasitic nematode proteins containing signal sequences whose presence in specialized secretory cells has preferably, though not necessarily, been demonstrated; (3) *C. elegans* secretory products that have been detected in external secretions, regardless of whether a homolog has been identified in a parasitic nematode species; (4) *C. elegans* secretory products that have been detected in a specialized secretory cell (e.g., an amphidial or pharyngeal gland cell), regardless of whether a homolog has been identified in a parasitic nematode species.

(iv) Chemical Screens

The inventive screening methods involve testing compounds to determine their effect on the nematode secretory pathway that results in secretion of the secretory product. The effect on the nematode secretory pathway can be assessed by determining the effect of a test compound on the product of a gene encoding a nematode secretory protein (e.g., determining the effect of the compound on the level or localization of an RNA transcribed from the gene or the level or localization of a protein translated from an RNA transcribed from the gene), and/or determining the effect of a test compound on the secretion of the nematode protein (e.g., the amount of the protein present in the external environment). Thus the inventive screening methods involve exposing a nematode, preferably *C. elegans*, to a test compound or a battery of test compounds and detecting the product of a nematode secretory pathway (e.g., a nematode secretory protein or an RNA encoding such a protein). In preferred embodiments of the invention the protein is detected in the external environment. In this regard it is noted that *C. elegans* can be cultured in liquid medium. Thus in preferred embodiments of the invention the secretory product is detected in the culture medium. The product can be detected using any appropriate technique. Detection methods are discussed further below.

In a preferred embodiment of the invention the screen is adapted for the testing of multiple compounds in a high throughput fashion. Methods for growth of large quantities of *C. elegans* are well known in the art. (See, for example, Lewis, J. and Fleming, J., "Basic Culture Methods", pp. 187–204 in *Methods in Cell Biology*, Epstein, H. and Shakes, D., (eds.), Vol. 48, Academic Press, San Diego, 1995, and references therein.) Methods for using *C. elegans* to perform high throughput screening are also known in the art (See, for example, Rand, J. and Johnson, C., "Genetic Pharmacology", in *Methods in Cell Biology*, Vol. 48, pp. 187–204, 1995, and references therein.) For example, according to one procedure *C. elegans* are placed in liquid culture (e.g., in S medium or axenic medium), preferably in multi-well plates, e.g., 24 well plates, 96 well plates, 384 well plates, etc. The choice of culture conditions may be determined at least in part by the nature of the product being detected and the level at which it is secreted. For example, for certain products growth in axenic medium is preferred. Growth in axenic medium avoids the need for a bacterial food source, thereby eliminating bacterial proteins from any resulting culture supernatant or protein preparation in which a secretory product is to be detected.

In certain preferred embodiments of the invention approximately equal numbers of worms (e.g., between 5 and 25 worms per well for 96 well plates) are placed in each well. This can be accomplished, for example, by uniformly suspending worms in liquid prior to dispensing. In certain embodiments of the invention "approximately equal numbers of worms" means that the number of worms per well can vary by not more than 1%, not more than 5%, not more than 10%, not more than 20%, not more than 25%, not more than 30%, not more than 40%, or not more than 50% from the average number of worms per well. Other measures, such as standard deviation in the number of worms per well, can be used. In general, one of ordinary skill in the art will know, depending on the assay, how much variability in the number of worms per well is permissible. In addition to the technique involving uniform resuspension of worms prior to dispensing, commercially available machines, e.g., the Multidrop 384 from LabSystems and the COPAS machine, produced by Union Biometrica, Inc., (Somerville, Mass.), for more precise delivery of specified numbers of animals, can be used. The worms are cultured for between 3 and 7 days, by which time the total population may range from several hundred to several thousand worms. Alternatively, a larger number of worms (e.g., several hundred to several thousand per well in a 96 well plate), may be added initially to the wells. Test compounds are added to each well, and the product of a nematode secretory pathway is detected. The compound may be added prior to, at approximately the same time as, or a variable amount of time after the worms are dispensed. Preferably the compound is added shortly (e.g., within several hours) after the worms are dispensed in order to prevent accumulation of secretory product that could obscure the effect of a subsequently added compound. The worms are cultured in the presence of the compound for a variable period of time, e.g., several hours to several days prior to detection of the secretory product. Compounds that inhibit a nematode secretory pathway are identified by identifying wells in which the activity or amount of secretory product detected is less than that detected in control wells to which no compound is added. Although in preferred embodiments of the invention the screen is performed using *C. elegans* grown in liquid culture, the inventive screens can also be performed using *C. elegans* grown on solid medium (e.g., on agar plates), in which case compounds can be added to the poured plates and allowed to diffuse into the medium. Multiwell plates containing 96 wells are presently preferred, but the invention may be practiced using multiwell plates having smaller or larger numbers of wells such as are well known in the art. Note that for high throughput purposes the invention is not limited to using multiwell plates but may use any convenient format employing multiple vessels.

The worms can be cultured under various conditions before, during, and/or after the period of exposure to the test compounds. For example, the temperature, pH and/or osmolarity of the culture media can be varied. The worms can be cultured in the presence or absence of nutrients. One skilled in the art will be able to select varied environmental conditions compatible with life. Such conditions may influence the activity of nematode secretory pathways, which may result in increased sensitivity for the screen. For example, secretory activity may be increased under certain environmental conditions. The screen can also be performed using *C. elegans* in different life stages, e.g., different larval stages including the dauer stage. Methods for generating synchronized populations of worms, including dauers, are well known in the art. As mentioned above, the alternative L3 stage known as dauer resembles, both phenotypically and biochemically, the infective L3 stage in many parasitic nematodes. Nematode secreted products may play a particularly important role in the infection process and succeeding events. In certain embodiments of the invention the screen is performed using dauer stage *C. elegans* that have been stimulated to resume development (e.g., by exposure to nutrients).

Compounds suitable for screening include small molecules, natural products, peptides, nucleic acids, etc. Sources for compounds include natural product extracts, collections of synthetic compounds, and compound libraries generated by combinatorial chemistry. Libraries of compounds are well known in the art. One representative example is known as DIVERSet™, available from ChemBridge Corporation, 16981 Via Tazon, Suite G, San Diego, Calif. 92127. DIVERSet™ contains between 10,000 and 50,000 drug-like, hand-synthesized small molecules. The compounds are pre-selected to form a "universal" library that covers the maximum pharmacophore diversity with the minimum number of compounds and is suitable for either high throughput or lower throughput screening. For descriptions of additional libraries, see, for example, Tan, et al., "Stereoselective Synthesis of Over Two Million Compounds Having Structural Features Both Reminiscent of Natural Products and Compatible with Miniaturized Cell-Based Assays", *Am. Chem Soc.* 120, 8565–8566, 1998; Floyd C D, Leblanc C, Whittaker M, *Prog Med Chem* 36:91–168, 1999. Numerous libraries are commercially available, e.g., from AnalytiCon USA Inc., P.O. Box 5926, Kingwood, Tex. 77325; 3-Dimensional Pharmaceuticals, Inc., 665 Stockton Drive, Suite 104, Exton, Pa. 19341-1151; Tripos, Inc., 1699 Hanley Rd., St. Louis, Mo., 63144-2913, etc.

In general, compounds may be dissolved in any appropriate solvent, preferably a solvent that does not exert deleterious effects on *C. elegans* growth, development, etc. at the final concentration after addition of the compound solution to the nematode culture medium. In this regard it is noted that *C. elegans* can tolerate modest amounts of various common solvents (e.g., <1% dimethyl sulfoxide, <4% ethanol, <2% methanol) with little effect on growth or behavior. Thus the compound can be added to culture medium containing solvent (e.g., 1% dimethyl sulfoxide). In certain embodiments of the invention it may be desirable to employ lower solvent concentrations (e.g., when worms are grown in 384 well plates). Furthermore, the screen can also be performed by adding compounds to wells prior to the addition of worms, in which case the solvent can be allowed to evaporate before worms and culture media are added.

A range of concentrations of the compound may be tested for effects on a *C. elegans* secretory pathway. As is well known to one of ordinary skill in the art, virtually any compound can have deleterious effects on an organism if present at sufficiently high concentration. Thus at sufficiently high concentration many compounds may affect secretion through nonspecific mechanisms (i.e., mechanisms that are not specific for a component of the secretory pathway), such as through general cytotoxic effects, neurotoxic effects, etc. Preferred compounds, on the other hand, specifically affect nematode secretion while not causing general toxicity to the organism. Of course compounds that do exert more general toxic effects may also be worth investigating as potential nematicides. Preferred compounds exert their effects on nematode secretion at concentrations practical for administration as therapeutic agents (e.g., at concentrations that do not cause unacceptable adverse effects in the host organism being treated) or as pesticides (e.g., at concentrations that do not cause unacceptable adverse effects on either nontargeted animal or plant species in the environment). Screens can be performed, for example, at relatively low concentrations such as <0.1 μg/ml, at higher concentrations such as 1 to 100 μg/ml, or at still higher concentrations, e.g., up to 1 mg/ml. In general, one of ordinary skill in the art will be able to select appropriate concentration ranges for testing, and the foregoing examples are not intended to be limiting. Of course the screen need not be performed in liquid culture but may employ worms growing on solid medium, e.g., agar plates. In this case the compound can be added to the agar, e.g., after pouring the plates, at any desired concentration.

Another parameter that may be varied at the discretion of the practitioner is the length of time between exposure to the compound and detection of the product of the nematode secretory pathway. In this regard it is noted that compounds may become unstable after addition to the culture medium, in which case it may be desirable to perform the detection assay relatively soon after exposing the nematodes to the compound. However, it is noted that the effect of a compound on a secretory pathway may not be immediately apparent. For example, if the secretory product is a stable protein whose secretion is inhibited by a test compound, a decrease in the level of the protein in the medium may not be apparent until some time after secretion is inhibited. Thus it may be desirable to perform the detection assay at a range of times following addition of the compound to the nematode culture medium.

(v) Detection Methods and Reporter Genes

As mentioned above, the product of a nematode secretion pathway can be detected using any of a variety of methods. If, as in preferred embodiments of the invention, the product is a protein, it can be detected using immunological techniques that are well known in the art such as ELISA assays or modifications thereof. Information regarding such techniques may be found, for example, in Section 11.2 in *Current Protocols in Molecular Biology*, Ausubel, F A, et al. (eds.), Wiley and Sons, New York, originally published in 1988 and supplemented subsequently with updated sections, and in Chapter 14 of Harlow and Lane (eds.), *Antibodies* (mentioned above). As described in the latter, in general, immunological detection techniques can be divided into (1) antibody capture assays; (2) antigen capture assays; (3) two-antibody capture assays, any of which can be configured by one of ordinary skill in the art to accomplish detection in a qualitative, semi-quantitative, or quantitative mode. Furthermore, one of ordinary skill in the art will be able to select an appropriate assay taking into consideration factors such as the abundance of the molecule to be detected and the relative sensitivity of different assay formats. In general, a two-antibody capture assay is used in certain preferred embodiments of the invention as described in the following paragraph.

More specifically, in one embodiment of the invention the wells of a microtitre plate (or other suitable support) are coated with an antibody that specifically binds to the protein (or other secreted molecule) to be detected. A portion of medium in which worms exposed to test compound have been cultured is contacted with the support under conditions suitable for binding of the antibody to the protein. Unbound material is removed (e.g., by washing), and a second antibody capable of specifically binding to the protein is added. The second antibody is typically an antibody modified so as to render it more readily detectable, e.g., conjugated with alkaline phosphatase, digoxygenin, or biotin, in which cases it may be detected using an alkaline phosphatase detection system, fluorescently labeled anti-digoxygenin antibody, or fluorescently labeled streptavidin, respectively. Of course numerous other detection methods known to those of skill in the art are also within the scope of the invention. Preferably the second antibody binds to a different epitope of the protein than the first antibody.

According to another embodiment of the invention, when the second antibody and the first antibody are obtained from different species (e.g., rabbit and goat), the second antibody need not be modified so as to render it more readily detectable but instead can be detected by the addition of a third antibody that binds to the Fc portion of the second antibody but does not bind to the first antibody. This third antibody (of which many are commercially available) is typically an antibody modified so as to render it more readily detectable using any of the detection modalities described above. An advantage of such a detection system is that the third antibody, since it need not specifically bind to the protein being detected, can be any of a variety of widely available commercially available secondary antibodies.

In certain embodiments of the invention, e.g., if a competitive antibody capture assay is used, the assay setup itself requires the availability of significant quantities of the antigen to be detected (i.e., the product of a nematode secretory pathway). In such a case the antigen can be produced in vitro, e.g., using any of a variety of in vitro expression systems (bacterial, yeast, insect cell, etc.) that are known in the art.

As described above, in preferred embodiments of the invention the molecule to be detected comprises a detectable marker such as an epitope tag, which can be recognized by commercially available antibodies. However, in certain embodiments of the invention the molecule to be detected does not comprise a marker that can be conveniently detected by immunological means. Furthermore, in certain embodiments of the invention two antibodies are used for the detection assay. In these cases it may be desirable to produce an antibody that specifically binds to the molecule to be detected. Methods for producing such antibodies, e.g., monoclonal or polyclonal antibodies, are well known in the art and are described, for example, in Harlow and Lane (eds.), *Antibodies*. These methods may employ an antigen produced as described above. Alternately, peptides may be selected based on the sequence of a protein to be detected and used as antigens for the production of antibodies that specifically bind to the protein.

In certain embodiments of the invention a secretory protein is detected using nonimmunological means. For example, any activity of the protein can be detected. Thus, for example, if the protein is an enzyme, the protein can be detected by detecting the product of a reaction catalyzed by the protein. If the protein is a protease, cleavage of a substrate by the protein can be detected. Methods for detecting cleavage of a substrate include the use of FRET (fluorescence resonance energy transfer) in which a change in observed fluorescence intensity occurs as a substrate is cleaved.

In certain preferred embodiments of the invention a transgenic nematode carrying a gene (a transgene) that serves a reporter function is used in the screen. The transgene itself (or a portion thereof) is referred to herein as a reporter gene or reporter. The product of the transgene (RNA, protein, etc.) may also be referred to as a reporter, but it will be clear from the context whether reference is made to the transgene or a product thereof. In general, expression or activity of the reporter serves as a marker for the product of a nematode secretory pathway. For example, the activity or level of the reporter can reflect the activity or level of a protein of interest, e.g., a nematode secretory protein. To this end, the transgene preferably includes a DNA sequence encoding a detectable marker operably linked to a regulatory element that normally regulates expression of an endogenous gene. The endogenous gene preferably encodes a product of a nematode secretory pathway, e.g., a nematode secreted protein. However, in certain embodiments of the invention the gene may instead encode another component of a nematode secretory pathway, e.g., a protein involved in any step of the pathway. Thus the invention provides a transgenic nematode, the cells of which comprise a reporter gene (the transgene) whose expression reflects the expression of a gene involved in a nematode secretory pathway, or a homolog thereof. In particular, the transgene comprises a regulatory element from a gene involved in a nematode secretion pathway, operably linked to a detectable marker. Expression can comprise RNA expression, protein expression, localization, temporal or spatial expression pattern, etc., or any combination of these.

In certain embodiments of the invention the reporter gene comprises a regulatory region (preferably including the promoter) for a gene encoding a protein of interest (e.g., a nematode secretory protein or homolog thereof), operably linked to a nucleotide sequence encoding a detectable marker. In certain embodiments of the invention the detectable marker is expressed in a dorsal pharyngeal gland of the transgenic nematode. In certain embodiments of the invention the detectable marker is expressed in the subventral pharyngeal gland of the transgenic nematode. In certain embodiments of the invention the detectable marker is expressed in an amphid sheath cell of the transgenic nematode. Detectable markers such as green fluorescent protein (GFP) or other fluorescent proteins (See, for example, U.S. Pat. No. 5,491,084, U.S. Pat. No. 5,981,200, Fire, A., et al., GFP applications in *C. elegans*, in Green Fluorescent Protein: Properties, Applications, and Protocols, Chalfie, M. and Kain S., (eds.), John Wiley and Sons, New York: 1998, Matz, M V, et al., Fluorescent proteins from nonbioluminescent Anthozoa species, Nat. Biotechnol., 17: 969, 1999, and references therein.) are used in certain preferred embodiments of the invention. Example 4 describes the construction of a *C. elegans* strain carrying a GFP-containing transgene that functions as a reporter for the expression and secretion of VAP-1, the *C. elegans* homolog of the *A. caninum* secretory protein ASP-1. The transgene is referred to as vap-1::gfp to indicate that the transgene comprises a regulatory element that normally regulates expression of the endogenous vap-1 gene operably linked to a DNA sequence encoding GFP. Similar nomenclature is employed with respect to other transgenes described herein. It is to be understood that such transgenes may comprise, in addition to the regulatory region of the indicated endogenous gene, a portion of the coding sequence, intron(s), and/or 3' untranslated region of the endogenous gene. In addition, further expression control or localization elements may be included, such as a nuclear localization signal (NLS). The left to right order of the elements listed in the name of the transgene corresponds to the 5' to 3' order of the sequences in the transgene itself. The corresponding polypeptide product will be similarly designated except that a dash (-) will be used rather than the :: symbol. For example, VAP-1-GFP refers to a polypeptide comprising some or all of the VAP-1 amino acid sequence upstream of some or all of the GFP amino acid sequence (i.e., the VAP-1 sequences are at the N terminus of the protein relative to the GFP sequences).

One skilled in the art will recognize that a wide variety of reporter genes and associated detection methods can be used in the practice of the invention, and the methods disclosed herein are not limited to any specific reporter gene or genes. Markers that produce a fluorescent, chemiluminescent, or colorimetric readout suitable for detection using an automated plate reader are generally preferred since it is desirable to perform the screen in a high throughput fashion. One skilled in the art will readily be able to select appropriate detection methods for any particular reporter gene. For example, if the reporter gene encodes a fluorescent protein, one skilled in the art will be able to select appropriate excitation wavelengths (e.g., near UV or blue light in the case of GFP), microscopes, fluorescence detectors, etc., for detection of the marker. Examples of additional reporter genes that can be used to monitor gene expression and/or protein secretion include, but are not limited to, luciferase, genes encoding an enzymatic activity such as β-galactosidase, chloramphenicol acetyltransferase (CAT), horseradish peroxidase, alkaline phosphatase, or active portions of any of these. Alternatively, the reporter may comprise a predetermined polypeptide sequence which can be recognized by a molecule such as an antibody. Such predetermined polypeptide sequences include, but are not limited to, epitope tags such as the HA tag, Myc tag, etc., for which monoclonal antibodies are commercially available. Example 7 describes the construction of a transgenic *C. elegans* carrying a transgene comprising a Myc epitope tag that functions as a reporter for the expression of VAP-1, the *C. elegans* homolog of the *A. caninum* secretory protein ASP-1.

As will be appreciated by one of ordinary skill in the art, variants of any of the reporters described above may also be used, provided that such variants retain the features necessary for their detection. Such variants include polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms, e.g., fluorescence, recognition by an antibody, etc.

Methods for the creation of reporter genes, also referred to as reporter fusions, for use in *C. elegans*, e.g., for assessing the expression pattern, expression level, etc. of a gene or protein of interest are well known in the art, and a variety of vectors are available that have been designed for this purpose. Several sets of vectors that find particular use for construction of *C. elegans* reporter genes are available from the laboratory of Dr. Andrew Fire, Carnegie Institution of Washington, Department of Embryology, 115 West University Parkway, Baltimore, Md. 21210. The modular nature of the vectors and general principles of their construction are described in Fire, A., et al., "A modular set of lacZ fusion vectors for studying gene expression in *Caenorhabditis elegans*", Gene 93: 189–198, 1990 and in Mello, C. and Fire, A., "DNA transformation" in Methods in Cell Biology, Vol. 43, cited above. In general, the vectors are built on a pUC plasmid backbone and comprise first, second, and third multiple cloning sites (MCS) intended, respectively, for insertion of a 5' regulatory region including a promoter for a gene of interest, a coding region (e.g., a DNA sequence encoding a detectable marker), and, if desired, 3' regulatory sequences. The first and second MCS are separated by a synthetic intron, and the second and third MCS are separated by a 3' UTR from the *C. elegans* unc-54 gene. Available vectors include vectors comprising sequences coding for GFP and variants thereof (with or without a nuclear localization sequence), in which case the practitioner need only insert regulatory sequences (and optionally coding sequences) from his or her gene of interest in order to create a reporter transgene. Detailed descriptions of these vectors and their properties is available at www.ciwemb.edu/pages/firelab.html. One skilled in the art will readily be able to adapt such vectors for any particular gene of interest.

As mentioned above, the transgene preferably includes regulatory sequences that are sufficient to direct expression of the endogenous gene, e.g., a promoter sequence. As will be appreciated by one of ordinary skill in the art, such regulatory sequences for a particular gene are typically located upstream (i.e., in the 5' direction) from the coding sequence, typically within 5 kB of the predicted initiator methionine. However, as will be appreciated by one skilled in the art, the location of promoter elements can vary. In certain embodiments of the invention the transgene includes up to 2 kB of genomic sequence immediately upstream (i.e., in the 5' direction from the start codon) from the coding sequence of a gene of interest. In other preferred embodiments of the invention the transgene includes up to 4 kB, up to 6 kB, up to 8 kB, up to 10 kB, or up to 20 kB of genomic sequence immediately upstream (i.e., in the 5' direction from the start codon) from the coding sequence of a gene of interest.

The transgene can also comprise part or all of the coding sequence of the protein of interest. As is well known in the art, coding regions may contain sequences that influence transcription, RNA processing, etc., and may also contain sequences that influence the localization of the RNA or protein product of the gene, etc. In particular, in *C. elegans* expression signals are frequently found in the larger intron sequences. The transgene can also comprise additional regulatory regions such as splice sites, polyadenylation sites, terminators, 3' untranslated regions, etc., all of which are well known in the art and may influence expression of the transgene.

In certain embodiments of the invention the transgene comprises sequences that code for a nuclear localization signal (NLS), i.e., a sequence that directs the transport of a protein from the cytoplasm into the nucleus. Such sequences are well known in the art (See, for example, Dingwall, C. and Laskey, R. *Trends Biochem. Sci.*, 16: 478–481, 1991, and references therein.) For example, the SV40 NLS is known to effectively direct the nuclear localization of proteins in *C. elegans*. Causing the protein to localize in the nucleus may improve detectability (e.g., by generating a high local concentration of the protein in the nucleus) and thus may be useful for determining which cells, organs, etc., express a particular gene of interest and for identifying compounds that affect the synthesis of the gene product. In addition, cell identification in *C. elegans* is generally based on positions of the cell nuclei since cell nuclei may be more easily observed than cell bodies by differential interference contrast (DIC) microscopy. Therefore, reporters comprising a nuclear localization sequence may find particular use in identifying the cells that express a gene of interest.

Particularly preferred *C. elegans* reporter transgenes comprise a regulatory element comprising between 0 and 10 kB of *C. elegans* genomic DNA sequence immediately 5' from the start codon of any of the following *C. elegans* genes: vap-1, vap-2, and other vap family members. Additional preferred *C. elegans* reporter transgenes comprise a regulatory element comprising between 0 and 10 kB of *C. elegans* genomic DNA sequence immediately 5' from the start codon of any of the following *C. elegans* cathepsin B like genes: cpr-4, cpr-5, cpr-6, W07B8.1, W07B8.4, and F32H5.1, or the cathepsin L-like gene T03E6.7. The regulatory element preferably includes the promoter for the gene. In addition to such a regulatory element preferred transgenes may optionally include part or all of the coding sequence of the corresponding gene, one or more introns (or a portion thereof) from the corresponding gene, and part or all of the 3' UTR from the corresponding gene. Preferred transgenes further include a DNA sequence encoding a detectable marker such as those described above, preferably GFP or a variant thereof, or a Myc epitope tag. Certain preferred transgenes include a nuclear localization sequence. In preferred embodiments of the invention the transgenes are constructed using the set of modular vectors mentioned above. Examples 3, 5, and 7 describe the construction of various preferred transgenes.

Methods for generating transgenic *C. elegans* (i.e., methods for transforming *C. elegans* with exogenous DNA) are known in the art and are described, for example, in Mello, C. and Fire, A., "DNA transformation" in *Methods in Cell Biology*, Vol. 43, cited above. In general, any source of DNA (e.g., plasmid DNA, cosmid DNA, PCR product, etc.) can be used. Transgenic *C. elegans* may be obtained by microinjection of the DNA sequence of interest into the cytoplasm of the hermaphrodite syncytial gonad. In order to facilitate detection of *C. elegans* that have been successfully transformed, a transformation marker is typically injected with the sequence of interest. Such a marker comprises a DNA sequence that confers a detectable phenotype on transformants. A number of such markers are known in the art (e.g., a dominant rol-6 allele, which codes for a mutant collagen that confers a rolling phenotype, the lin-15 gene, which corrects the lin-15 loss-of-function multivulva phenotype, etc.). In certain preferred embodiments of the invention a wild type *C. elegans* strain is transformed. However, in other embodiments of the invention a *C. elegans* mutant strain having desirable properties is transformed. For example, certain mutants (smg mutants) exhibit defects in nonsense-mediated mRNA decay. Expressing a transgene that comprises a long untranslated region in a smg mutant strain may be useful to reduce degradation of the mRNA transcribed from the transgene. One such mutant is the conditional (temperature-sensitive) smg-1 mutant strain PD8120 smg-1 (cc546ts). Additional mutants that may be used in the practice of the invention include mutants that display enhanced uptake of test compounds, e.g., mutants with increased cuticular permeability; mutants with altered or reduced metabolism or clearance of test compounds, etc.

As is well known in the art, following transformation *C. elegans* transgenes are maintained as large extrachromosomal arrays consisting of multiple copies of the DNA sequence of interest (e.g., a DNA sequence comprising a fusion gene) and the marker DNA sequence. Since the level of inheritance of such extrachromosomal arrays is virtually always somewhat less than 100%, in certain embodiments of the invention it is desirable to produce a transgenic line with one or more integrated copies of the transgene. Among the various approaches to generating integrated transgenes (described in Mello, C. and Fire, A., referenced above) the most widely used is (in brief) to gamma irradiate a population carrying an extrachromosomal array comprising the transgene, maintain the population under nonselective conditions for several generations, and identify progeny homozygous for the transforming sequences. Since gamma irradiation typically results in various mutations in addition to integration of the transgene, in preferred embodiments of the invention the strain bearing the integrated transgene is outcrossed several times. Another approach involves the use of UV light. The generation of a *C. elegans* strain bearing an integrated vap-1::nls-gfp transgene using this technique is described in more detail in Example 9, and similar approaches may be applied to generate a transgenic *C. elegans* strain bearing any integrated transgene from a strain bearing a corresponding extrachromosomal array.

In certain embodiments of the invention, rather than detecting the end product of the secretion pathway, i.e., the secreted protein itself or a reporter for expression of the secreted protein, an intermediate in the pathway or a protein that functions in the pathway can be detected. For example, in certain embodiments of the invention an enzyme involved in synthesis of a nematode secreted protein can be detected.

Detection can, in general, be direct or indirect. Direct detection may involve, for example, detection using an antibody or other molecule that specifically binds to a protein or other molecule being detected, detection of a fluorescent or chemiluminescent moiety that forms part of a protein being detected, etc. Indirect detection may involve, for example, detecting the product of a reaction catalyzed by a protein being detected. In preferred embodiments of the invention the molecule being detected is detected outside the organism, e.g., in the culture medium. However, this need not be the case, and the invention encompasses detection of the molecule within the organism, e.g., within the pharyngeal lumen, or within a secretory cell.

Although the inventive methods described thus far have involved screening for inhibitors of secretion pathways using whole organisms, it will be appreciated that similar methods may be employed to screen for inhibitors of nematode secretion pathways using tissue culture systems in which cell lines derived from nematode secretory cells, e.g., gland cells, amphidial cells, etc., are propagated in vitro. The present application contemplates the use of such cell lines comprising any of the transgenes mentioned above, in the event that the ability to propagate nematode cell lines in vitro is developed.

(vi) Testing and Uses of Identified Compounds

In certain embodiments of the invention it is desirable to test compounds that inhibit a nematode secretory pathway to determine their effects on viability, growth, development, infectivity, etc., of a parasitic nematode species. Direct effects (e.g., killing) on the target species can be observed. A number of in vitro culture systems and models for nematode parasitism are known in the art and can be used for these purposes. Example 12 describes the process of testing a candidate compound to determine its effects on the release of ASP-1 by *A. caninum* and the resumption of larval feeding and development upon stimulation (an in vitro model for parasitism). Candidate compounds can also be tested, for example, by administering them to a host (e.g., an animal or plant) either before or after infection of the host by a parasitic nematode and assessing the ability of the compound to modify the course of infection, e.g., to reduce the incidence or severity of infection, to reduce the parasite burden, to reduce the amount of a second agent needed to control the infection (i.e., to synergize with another anti-nematode agent), etc. Candidate compounds can also be tested by comparing the amount of damage caused by a plant parasitic nematode to a susceptible plant species grown in the presence of the compound versus the amount of damage caused by the same number of nematodes in the absence of the compound. In general, methods well known in the art for evaluating the efficacy of anti-nematode therapeutic agents and standard methods for evaluating anti-nematode agricultural agents may be used. For animal and human parasitic nematodes such methods are described, for example, in Conder G A, Campbell W C. "Chemotherapy of nematode infections of veterinary importance, with special reference to drug resistance", *Adv Parasitol,* 35:1–84, 1995; Campbell W C, Rew R S, eds., *Chemotherapy of Parasitic Diseases,* New York: Plenum Press, 1986. Methods applicable to plant parasitic nematodes are described in Hague N G M, Gowen S R. "Chemical control of nematodes", Chapter 5 in Brown R H, Kerry B R, eds. *Principles and Practice of Nematode Control in Crops,* Sydney: Academic Press, pp.131–178, 1986.

Compounds that inhibit a nematode secretory pathway may be used as therapeutic agents, as pesticides, or in any context in which it is desired to inhibit nematode growth, feeding, and/or reproduction. If the compound was identified by screening natural product extracts, the active component can be determined using standard techniques. If the compound was identified by screening a library appropriate standard techniques may be used to determine the identity of the compound. In many cases this is entirely straightforward since individual compounds are distributed in individual vessels, microtitre plates, etc., that comprise the library. In other cases, (e.g., for a combinatorial library), identifying the compound may involve decoding tags to determine a synthetic route, etc. One of ordinary skill in the art will be able to select and apply appropriate techniques to identify the compound. Note that identifying the compound is not a requirement in certain embodiments of the invention. For example, if a component of a natural product extract inhibits a nematode secretory pathway, the extract or an active fraction thereof may be employed without identifying the active component(s).

Potential pharmaceutical candidates can be evaluated for various physicochemical properties that may influence solubility and/or absorption. (See, for example, Blake, J., "Chemoinformatics—predicting the physicochemical properties of 'drug-like' molecules", *Curr. Op. Biotechnol.,* 11: 104–107, 2000, and references therein.) Drug candidates are typically screened for cytotoxicity and evaluated in a standard set of cell-based assays well known in the pharmaceutical arts (e.g., to examine metabolism). For therapeutic purposes, pharmaceutical compositions comprising an active compound or compounds can be formulated according to methods well known in the pharmaceutical arts for delivery by any appropriate route (e.g., oral, intravenous, transdermal, etc.) in any appropriate vehicle or carrier. Methods for determining an appropriate formulation and route of administration are known in the art. Determining an appropriate dose will involve trials (initially in animals and ultimately in humans in the case of human therapeutics) to evaluate the effect of a candidate therapeutic agent on the course of nematode infection and/or to evaluate the adverse effects (if any) of the agent. The pharmaceutical compositions can be used either alone or in combination with other anti-nematode agents.

For use as pesticides, compounds that inhibit a nematode secretory pathway can be formulated for application using conventional techniques, e.g., as a liquid or powder typically for delivery to the plant and/or to the soil at or near the time of planting, during irrigation, etc. The compounds can be combined with an agriculturally suitable carrier, e.g., a liquid such as water, alcohol, or other organic solvents or oils, or a powder such as talc, clay, or other silicate to produce an agriculturally appropriate anti-nematode agent. The compounds may also be formulated for delivery as fumigants. The compounds can be used either alone or in combination with other anti-nematode agents. The anti-nematode agents of the invention need not be applied directly to the plant or to its roots but may be applied in the vicinity of the plant, e.g., within a meter from the location of the plant. The agents can also be applied to a seed from which a plant is to be grown. For example, seeds can be coated with the agents prior to planting.

In certain embodiments of the invention compounds that inhibit a nematode secretory pathway are expressed by transgenic plants or animals, so that the transgenic plant or animal exhibits increased resistance against nematode infection and/or damage. Most typically, an inhibitory compound suitable for expression in a transgenic organism is a nucleic acid, peptide, or polypeptide, although it is within the scope of the invention to generate transgenic organisms that express or overexpress small molecules, lipids, etc., e.g., by introducing genes that encode enzymes involved in the synthesis of such compounds into the organism. Methods of generating transgenic plants or animals are well known in the art. The transgene may comprise endogenous sequences, exogenous sequences, or a combination of the two. The transgene will typically comprise regulatory elements capable of directing gene expression within a particular organism or cell type in which the transgene is to be expressed (e.g., a promoter) operably linked to DNA sequences that encode an inhibitory compound, an enzyme involved in the synthesis of such a compound, etc. In addition to a promoter, other regulatory elements may also be included in the transgene, e.g., splice sites, polyadenylation sites, transcriptional terminators, etc. In some cases increased expression of an inhibitory compound in a transgenic organism may be achieved by "knocking out" expression of an endogenous gene in the organism according to methods well known in the art. For example, such an endogenous gene may be a gene whose product normally inhibits expression of an endogenous inhibitor of a nematode secretory pathway or a gene whose product is an enzyme that uses a precursor of such an inhibitor as a substrate for synthesis of a non-inhibitory molecule.

In another aspect, the invention provides screens for compounds capable of stimulating or activating a nematode secretory pathway. The screen is performed essentially as described for identifying compounds that inhibit a nematode secretory pathway except that in the detection step, rather than identifying wells in which the activity or amount of secretory product detected is less than that detected in control wells to which no compound is added, wells in which the activity or amount of secretory product detected is greater than that detected in control wells to which no compound has been added are identified. Note that both inhibitory and stimulatory compounds may be detected in the same screen.

Compounds that increase or stimulate secretion are useful for a variety of purposes. For example, such agonists may be used as a basis for the design of antagonists. In addition, secretion stimulators may be used to increase overall secretion levels in the context of a screen for compounds that inhibit secretion, in order to raise the signal level against which any decrease in secretion would be detected.

(vii) Genetic Screens

In another aspect, the present invention provides methods and reagents of use in identifying targets for anti-nematode compounds that act on a nematode secretion pathway. As described above, secretion pathways involve a number of steps, each of which may involve multiple genes and their encoded proteins. The screens described above offer the potential to identify compounds that act on such a pathway but, typically, do not provide an indication of the immediate target, e.g., the gene(s) or protein(s) that interact directly with the compound and are affected by the compound. For example, a compound identified in a screen that tests for reduced accumulation of a nematode secretion product in the medium may act by inhibiting any of the steps described above. However, genetic screens for mutants whose response to the compound is either reduced (suppressed) or enhanced can reveal the identity of the target. Knowing the identities of potential targets (e.g., the amino acid sequence of protein targets, nucleotide sequence of gene targets, etc.) allows the use of tools such as molecular drug design, screens employing libraries particularly adapted for a given target, etc. Potential targets may include genes and proteins that are members of families that have been studied in other organisms (or in nematodes) and/or for which structural information, information about interacting molecules, etc. is already known. Given their attractiveness as potential targets for development of anti-nematode agents, it is of considerable use to identify genes and proteins involved in nematode secretion pathways in addition to the secretory products themselves and their corresponding genes.

A complementary method for identifying targets for anti-nematode compounds that act on a nematode secretion pathway involves performing a genetic screen for nematode mutants with reduced or altered expression and/or secretion of a nematode secretory product or homolog thereof. The frequency with which mutants are isolated can hint at the number of potential targets as well as the nature of the gene alterations (e.g., reduction of function, gain of function, etc.). Similar approaches have identified key components of several pathways in *C. elegans* including those controlling sex determination, cell specification, and cell death (Riddle, D. L., Blumenthal, T., Meyer, B. J., Priess, J. R., *C. elegans II*, Cold Spring Harbor: Cold Spring Harbor Laboratory Press, 1997; Wood, W. B., *The Nematode Caenorhabditis elegans*, Cold Spring Harbor: Cold Spring Harbor Laboratory Press, 1988) and have included the identification of mutations that affect the expression of reporter genes. Preferably the nematode is *C. elegans*, and preferably the nematode secretory product is a *C. elegans* homolog of a parasitic nematode secretory protein. The genetic screens of the invention may involve wild type *C. elegans* or, preferably, a *C. elegans* strain bearing a reporter gene such as a transgene comprising a regulatory region sufficient to direct expression of an endogenous gene of interest (e.g., a *C. elegans* homolog of a parasitic nematode secretory protein, a *C. elegans* secretory protein, a *C. elegans* homolog of a gene encoding a component of a parasitic nematode secretory pathway, or a component of a *C. elegans* secretory pathway) operably linked to a DNA sequence encoding a detectable marker. The transgene may additionally comprise coding sequence from the gene of interest, in which case the coding sequence from the gene of interest is fused in frame with the sequence encoding the detectable marker. The sequence encoding the marker may be located upstream, within, or downstream from the coding sequence provided that the two are in frame. The transgene may further comprise intron and/or 3' untranslated regions from the gene of interest. In general, any transgenic *C. elegans* strain such as those described above may be used in the genetic screens described herein.

In a preferred embodiment of the genetic screen, hermaphrodites from a *C. elegans* strain (either wild type or, preferably, a transgenic strain as described in the previous paragraph) are mutagenized (e.g., using a chemical mutagen such as EMS or ENU, irradiation, transposon-mediated mutagenesis, or any other mutagenesis technique). Their progeny (F1) are screened for dominant mutations, and the following generation (F2) is screened for recessive mutations. In an alternative embodiment of the invention the screen is an F2 clonal screen, in which the F3 progeny are assayed. In either case, mutants displaying altered expression of the gene of interest and/or altered secretion of an expression product of the gene are identified. In general, an appropriate method of identifying such mutants depends upon the particular *C. elegans* strain, e.g., upon the nature of the detectable marker encoded by the reporter gene in those embodiments of the invention in which a strain bearing a reporter transgene is employed. For example, in particularly preferred embodiments of the inventive genetic screen, the reporter gene comprises a fusion between a regulatory region of the gene of interest (possibly including a portion of the coding region and/or introns, other regulatory elements, etc.) and a fluorescent protein such as GFP. In this case, mutants that exhibit reduced or altered expression of the transgene can be detected by observation under epifluorescence microscopy. Reduced expression can include lack of or lower levels of expression than observed in wild type worms in some or all cells that normally express the gene and/or during some or all of the life stages in which the gene is normally expressed. Altered expression can include an altered temporal or spatial expression pattern (e.g., expression in cells that do not normally express the gene or expression during life stages in which the gene is normally not expressed). Altered expression can also include an increased level of the gene product within the animal, e.g., in the event that secretion per se is impaired while transcription and translation remain normal or in the event that transcription and/or translation is increased. In such a case the intensity of the signal generated by the transgene product inside the animal may be increased.

Particularly preferred reporter transgenes include, but are not limited to, transgenes comprising an upstream regulatory region including a promoter from any of the following *C. elegans* genes: vap-1, vap-2, other vap genes, operably linked to a DNA sequence encoding a detectable marker, e.g., GFP or a variant thereof. Additional preferred reporter transgenes include, but are not limited to, transgenes comprising an upstream regulatory region including a promoter from any of the following *C. elegans* genes: cpr-4, cpr-5, cpr-6, W07B8.1, W07B8.4, F32H5.1, and T03E6.7, operably linked to a DNA sequence encoding a detectable marker, e.g., GFP or a variant thereof. The transgenes may comprise additional regulatory elements such as those described above. In certain embodiments of the invention, the transgene includes a nuclear localization signal. The nuclear localization signal, by causing the transgene product to accumulate in the nucleus, facilitates its detection. Such reporter transgenes are particularly useful in performing screens for reduced or altered gene expression rather than in screens for detecting reduced or increased secretion.

In certain embodiments of the invention in which a reporter transgene encoding a detectable marker under control of a first regulatory region is integrated into the genome, the efficiency of the genetic screen may be improved by incorporating another copy of the detectable marker under control of a second regulatory region into the array. The second marker serves as an internal control to compensate for any potential variability in expression of the transgene due, for example, to mutagenesis at the integration site. The second regulatory region should be one that directs expression in a cell or set of cells that is substantially or entirely distinct from the cell or cells in which the copy of the detectable marker under control of the first regulatory region is expressed. For example, if the first regulatory region directs expression in amphid sheath cells (e.g., the vap-1 regulatory region), the second regulatory region could be, for example, the elt-2 regulatory region, which directs expression in intestinal cells. The use of such an internal control makes it possible to distinguish between reduction or alteration in gene expression that is specific to the sequences under control of the first regulatory region and nonspecific reduction or alteration in gene expression.

Detecting mutants with altered or reduced expression of a transgene by observing expression within the animal allows the identification of mutants from among a nonisogenic population of F1 or F2 animals. However, in certain preferred embodiments of the invention the screen is performed by detecting a secretory product in the medium as described above, in which case following mutagenesis the worms being screened are maintained individually (or with their progeny), e.g., in individual wells of a multiwell plate.

In general, a screen performed with a strain containing a reporter transgene comprising regulatory sequences but no or minimal coding sequence (other than sequences encoding the detectable marker) may be used to detect mutants with reduced or altered transgene expression (which is indicative of reduced or altered expression of the endogenous gene whose regulatory region forms part of the transgene). Screens to identify mutants with reduced or altered secretion of a secretion product but normal levels of expression of the gene that encodes the secretion product can be performed using wild type worms as a starting strain, in which case an endogenous secretion product is detected in the medium. However, such screens preferably employ as a starting strain transgenic worms that express a reporter gene comprising regulatory sequences and coding sequences, including sequences coding for a detectable marker, whose product is targeted appropriately to the secretory pathway and can be detected in the medium. Preferably the transgene encodes a signal sequence and at least a portion of an endogenous secreted protein (e.g., at least 50%, at least 75%, at least 90%, or 100% of the endogenous protein). In order to minimize potential interference with proper targeting of the protein to the secretory pathway, in certain preferred embodiments of the invention it is preferable to use a small detectable marker such as an epitope tag (e.g., Myc) rather than a large marker such as GFP.

In addition to mutants with reduced or altered secretion and normal levels of gene expression, another class of mutants that is expected to come out of a screen for altered secretion includes mutants that affect gene expression. These two classes of mutants can be distinguished in a variety of ways familiar to one of ordinary skill in the art. Although it may be desirable to determine which step(s) in the overall secretory pathway are affected by the mutation, it is not necessary to the practice of the invention.

Mutants identified as described above are preferably backcrossed (crossed to the starting strain) several times to eliminate extraneous mutations that may have been caused by the mutagen (i.e., mutations not reducing or affecting expression of the gene of interest). In certain embodiments of the inventive method mutations are mapped (e.g., using conventional two and three-factor crosses as described in Sulston and Hodgkin, Methods, in *The Nematode Caenorhabditis elegans*, W. B. Wood, ed., pp. 587–606, 1988; using polymorphic sequence tagged sites as described in Williams, B., Genetic Mapping with Polymorphic Sequence Tagged Sites in *Methods in Cell Biology*, Vol. 43, referenced above, using single nucleotide polymorphisms (SNPS) as described in Jakubowksi and Kornfeld, A local, high density, single nucleotide polymorphism map used to clone *Caenorhabditis elegans cdf*-1, *Genetics* 153: 743–752, 1999, or using any other available mapping technique.). Complementation tests are generally performed to determine the number of genes represented. In preferred embodiments of the invention the phenotypes of expression mutants are characterized with respect to the expression pattern of the gene of interest and also with respect to any of a variety of phenotypes including, for example, dauer formation, hatching, molting, or feeding. In preferred embodiments of the invention, the wild type version of the mutated gene is cloned. Methods for cloning *C. elegans* genes are well known in the art. Typically, after mapping a gene to a chromosomal region using, for example, two and three-factor crosses, cosmids spanning the region are injected into mutant worms, and the ability of a particular cosmid to complement the mutant phenotype is taken as an indication that the wild type gene is located on that cosmid. Individual genes located on the cosmid can then be individually assessed for their ability to complement the mutant phenotype.

Genes identified in the inventive genetic screen and their encoded proteins are targets for the development of compounds that inhibit nematode secretion pathways. For example, if a loss-of-function mutation (typically a recessive mutation) causes reduced secretion of a secretory protein, then an antagonist of the corresponding wild type gene or protein would be expected to have a similar effect. The screen may also lead to the discovery of genes whose normal function is to inhibit secretion. Loss-of-function mutations in such genes would be expected to result in increased levels of secreted protein. An agonist of the corresponding wild type gene or protein would be expected to cause reduced protein secretion. Thus compounds that are agonists or antagonists (depending on the gene) of a gene discovered in the inventive genetic screen or of their encoded proteins, are useful for inhibiting nematode secretion pathways. In addition to their utility for identifying targets, mutants that exhibit increased levels of a secretory product are useful in the chemical screens described above since the increased level of secretory product may facilitate detection and thus make it easier to identify compounds that inhibit the secretory pathway.

(viii) Vectors

The invention provides a variety of different vectors that are useful in the practice of certain of the methods described above. In particular, the invention provides vectors comprising polynucleotides that encode *C. elegans* VAP-1, VAP-2, or other VAP family members. In certain preferred embodiments of the invention the vectors comprise the nucleotide sequence of SEQ ID NO:2. In certain other preferred embodiments the vectors comprise the nucleotide sequence of SEQ ID NO:4. In certain other preferred embodiments the vectors comprise a nucleotide sequence of a predicted *C. elegans* gene encoding a VAP domain, e.g., a gene encoding a VAP-1 homolog having a BLASTP score of >100 when the VAP-1 amino acid sequence is used as input.

The invention also encompasses vectors comprising polynucleotides that encode variants of *C. elegans* VAP-1, VAP-2, or other VAP family members. Preferred VAP variants are at least about 80%, more preferably at least about 90%, and most preferably at least about 95% identical in amino acid sequence to a VAP amino acid sequence, e.g., the amino acid sequence of SEQ ID NO:1 in the case of VAP-1. Particularly preferred variant amino acid sequences differ by less than 20, yet more preferably less than 10, and yet more preferably less than 5 amino acids from a VAP amino acid sequence, e.g., the sequence of SEQ ID NO:1 in the case of VAP-1.

The invention also encompasses vectors comprising a variant of a polynucleotide sequence encoding *C. elegans* VAP-1, VAP-2, or another VAP family member. Preferred variants have at least about 80%, more preferably at least about 90%, and most preferably at least about 95% sequence identity to a polynucleotide sequence encoding *C. elegans* VAP-1, VAP-2, or another VAP family member. In one aspect the invention includes a variant of a polynucleotide sequence selected from the group consisting of SEQ ID NO:2 and SEQ ID NO:4 which has at least about 80%, more preferably at least about 90%, and most preferably at least about 95% sequence identity to the polynucleotide sequence of SEQ ID NO:2 or SEQ ID NO:4. Particularly preferred variant polynucleotide sequences differ by less than 20, yet more preferably less than 10, and yet more preferably less than 5 nucleotides from the original sequence.

In certain preferred embodiments of the invention any of the vectors may also comprise a regulatory region operably linked to one of the polynucleotide sequences described above. Preferably the regulatory region includes a promoter from the gene that encodes the VAP family member. For example, in a vector that comprises a polynucleotide sequence that encodes VAP-1, a preferred regulatory region comprises the vap-1 promoter. Preferably the regulatory region comprises between 1 nucleotide and 10 kB of nucleotide sequence upstream (i.e., in the 5' direction from) the start codon of a vap gene. In certain embodiments the regulatory region comprises between 1 nucleotide and 5 kB of upstream sequence.

In certain preferred embodiments of the invention any of the vectors may comprise a polynucleotide that encodes a detectable marker. In those vectors that comprise sequences encoding a VAP family member or portion thereof, the polynucleotide that encodes the detectable marker is preferably fused in frame with the sequences encoding the VAP family member or portion thereof, so that the vector directs expression of a fusion protein comprising the VAP family member or portion thereof and the detectable marker. In addition to coding sequences, any of the vectors may comprise introns and/or 3' untranslated region from the corresponding *C. elegans* gene.

In certain embodiments of the invention, rather than encoding a VAP family member the vectors comprise a regulatory region that comprises between 1 nucleotide and 10 kB of nucleotide sequence upstream (i.e., in the 5' direction from) the start codon of a vap gene, operably linked to a polynucleotide sequence that encodes a detectable marker.

As is well known in the art, due to the degeneracy of the genetic code (i.e., the fact that in many cases multiple different codons can code for the same amino acid), multiple different polynucleotide sequences encode VAP family members, and multiple different polynucleotide sequences encode any given detectable marker. The invention encompasses all of the sequences that can be made by substituting alternative codons in accordance with the genetic code. It is noted that such substitution must be made appropriately in view of the reading frame of the polynucleotide. It is further noted that many of these polynucleotide sequences will display little or no homology with the vap sequences present in the *C. elegans* genome. In certain embodiments of the invention it may be preferred to employ polynucleotides encoding VAP family members having a significantly different codon usage to that found in naturally occurring genes. For example, if the inventive polynucleotides are to be used to express a VAP family member in a heterologous system such as a bacterial or yeast expression system, it may be desirable to employ polynucleotides having a codon usage preferred for optimal expression in the heterologous system. Such codon usage preferences are well known in the art. Altering the nucleotide sequence encoding a VAP family member may have additional uses such as maximizing RNA stability, as it is well known in the art that RNA stability can be affected by the sequence of the RNA. It may be desirable to alter the codon usage when generating a C. elegans strain that expresses a VAP family member from a transgene.

It is noted that the invention is not limited to the embodiments described herein and the examples presented below and that various changes and modifications may be made by those of ordinary skill in the art without departing from the scope and spirit of the appended claims.

EXAMPLES

Example 1

Cloning and Sequence Analysis of C. elegans vap-1

Materials and Methods

An open reading frame on cosmid F11C7 (specifically F11C7.3) was identified as the C. elegans homolog of the gene encoding the A. caninum protein ASP-1 by searching the C. elegans genomic sequence database (available at www.sanger.ac.uk/Projects/C_elegans/blast_server.shtml) using the program TBLASTN (which compares an input amino acid sequence with translated genomic sequence). Primers F11C7.F1 (GCCAAACAAGTGCGGACTCTTATC=SEQ ID NO:5) and F11C7.R1 (GTGCTAGTTTTTGACGAACCCAG=SEQ ID NO:6) were designed based on the F11C7.3 sequence using the program MacVector. The primers were based on the cDNA of 1029 nucleotides originally predicted by the program Genefinder, which has been used to identify genes from genomic sequence, with the forward primer from the predicted first exon and the reverse primer from the predicted last exon. These primers were used to amplify a 1420 base pair genomic fragment from F11C7 cosmid DNA prepared according to standard methods (Favello, A., et al., "Genomic DNA Sequencing Methods", in *Methods in Cell Biology*, Vol. 43, referenced above.). The resulting fragment was end-labeled with $^{32}$P-dCTP and hybridized to plaque lift filters of a C. elegans λZAP cDNA library (Barstead, R J and Waterston, R H, *J. Biol Chem.*, 264:10177–85, 1989.) Hybridization was performed at 65° C. overnight, followed by two washes with 2×SSC at 65° C. Filters were placed on film at –70° C. for 4 days. Positive clones were identified and corresponding agar plugs were picked. Eluants of these plugs were screened by PCR using primers F11C7.F1 and F11C7.R1 to ensure that they contained the desired clone. PCR was performed using Taq DNA polymerase. The following PCR amplification conditions were used. Denaturing: temperature=95 degrees C., time=30 sec; Annealing: temperature=48 degrees C., time=1 min; Extension: temperature=72 degrees C., time=5 min. Forty rounds of amplification were performed. Secondary and tertiary rounds of screening were performed to isolate pure phage clones. Phage rescue was then used to isolate the inserts as pBluescript® phagemids (Stratagene) using the manufacturer's protocol. The largest clones were sequenced according to standard methods.

A BLASTP search of protein sequences available in GenBank was performed, and the CLUSTAL W program was used to align VAP-1 with selected other nematode VA proteins.

Results

The C. elegans ortholog of the gene encoding A. caninum ASP-1 was identified as a predicted open reading frame on cosmid F11C7 (specifically F11C7.3). The C. elegans gene was designated vap-1 for venom allergen-like protein-1. Numerous phage clones hybridized when a 1420 genomic fragment amplified using primers to the ORF was used to probe the cDNA library mentioned above, indicating the abundance of the transcript. The full-length vap-1 cDNA (submitted to GenBank under accession number AF112356) is 1341 base pairs in length and encodes a predicted 425 amino acid protein. The sequence of the full length vap-1 cDNA isolated by applicants indicates that the original Genefinder predicted cDNA of 1029 nucleotides was incorrect, in that it omitted the first exon (including the sequence encoding the signal peptide) and also the last exon. Unlike most nematode transcripts, but like the cDNAs encoding ASP-1 and other nematode VA cDNAs, the vap-1 cDNA does not appear to be trans-spliced (i.e., it lacks the trans-splicing leader sequence SL1 (Blaxter, M. L., Liu, L. X., Nematode spliced leaders-ubiquity, evolution, and utility, *Int. J for Parasitology*, 26, 1025–1033, 1996). The predicted VAP-1 protein contains two sequential venom allergen domains preceded by a 18 amino acid hydrophobic leader peptide sequence (MAVLAVVLLLACLERAVA=SEQ ID NO:7) characteristic of extracellularly secreted proteins. A BLAST search of GenBank and alignment of the identified homologous sequences confirmed that VAP-1 is most closely related to ASP-1 and is a member of the expanding nematode VA protein family.

Protein domain analysis revealed that the nematode VA protein family thus far contains three different types of overall structures, as shown in FIG. 2: (1) proteins of ~400–450 amino acids containing two sequential, perhaps evolutionarily duplicated, VA domains, typified by VAP-1 and ASP-1; (2) proteins of ~200–250 amino acids containing a single VA domain, which includes most reported members of the nematode VA family; and (3) proteins of >400 amino acids, containing an N-terminal nematode 6-cysteine repeat domain (Blaxter, M. L., Caenorhabditis elegans is a nematode, *Science*, 282, 2041–2046, 1998) followed by a C-terminal VA domain. This domain has been thus far found only in TcCRISP, identified from *Toxocara canis* infective larvae. FIG. 3 shows a CLUSTAL W alignment of VAP-1 with selected other nematode VA proteins. This figure shows the alignment between the two VAP-1 VAP domains (labeled as VAP-1 N and VAP-1 C), the two ASP-1 VAP domains (labeled as ASP-1 N and ASP-1 C) and the two VAP domains of C. elegans VAP-2 (labeled as VAP-2 N and VAP-2 C), C. elegans VAP-3, and MSP-1 (a VA homolog from *M. incognita*). (Identification of VAP-2 and VAP-3 is described in Example 2).

Example 2

Identification of Members of the VA Protein Family in C. elegans

A BLAST search of the complete C. elegans genome using the VAP-1 amino acid sequence revealed over 20 homologs of VAP-1 with a BLASTP score of>100. The locations of these proteins are presented on the schematic map shown in FIG. 4. By far the closest homolog to vap-1 is a gene on the same chromosome (chromosome X), which includes the predicted genes T05A10.4 and T05A10.5. Applicants have discovered that these genes were mispredicted as separate genes by the genome sequence annotators and are, in fact, a single gene. This gene has been designated vap-2. Confirmation that vap-2 actually comprises both predicted genes T05A10.4 and T05A10.5 was obtained by performing RT-PCR on RNA obtained from wild type N2 worms using standard protocols. The RT-PCR primer used for first strand cDNA synthesis was designated T05A10 rt and had the following sequence: 5'-CAC AAT CTG TTC CAA TCG GGC-3' (SEQ ID NO:8). This primer sequence is from the noncoding strand of gene T05A10.5 Forward and reverse primers used in the subsequent PCR reaction had the following sequences respectively: T05A10 f1: 5'-CGT GGT CCT TTC CGC TGT CAC TC-3' (SEQ ID NO:9); T05A10 r1: 5'-GTT CTT TCT GTT GCC TGC TGG-3' (SEQ ID NO:10). The forward primer is from the coding strand of T05A10.4, and the reverse primer is from the noncoding strand of T05A10.5 (5' to the RT-PCR primer). (The coding strand for vap-2 is on the opposite strand of cosmid T05A10 relative to what is in GenBank.

The predicted amino acid sequence of the VAP-2 protein (SEQ ID NO:3) and the nucleotide sequence of the vap-2 cDNA (SEQ ID NO:4) are presented in FIG. 1. The remaining predicted VA proteins in *C. elegans* appear to belong to the group of VA proteins having a single VA domain. Eleven VA family members are clustered on overlapping cosmids C39E9 and F49E11 on chromosome IV (indicated with an * in FIG. 4). Based on the *C. elegans* expressed sequence tag (EST) database (available at www.ddbj.nig.ac.jp/c-elegans/html/CE_INDEX.html), one of the VA genes, F49E11.10, is much more highly expressed than others. Applicants have designated this gene vap-3.

Example 3

Construction of vap-1::gfp and vap-1::nls-gfp Reporters

To construct a vap-1::gfp reporter gene, an ~6.5 kB BalI fragment from the vap-1 genomic region was amplified from *C. elegans* N2 genomic DNA by long PCR using primers F11C7.F30 (5'-CTCCTGATAACTTTTAGAGGTTTGG-3'=SEQ ID NO: 11) and F11C7.R30 (5'-CCTAATGAGCA-CACTACCAGTTTTG-3'=SEQ ID NO. 12), which lie outside two BalI sites in the genomic sequence. The fragment contained approximately 4.8 kB of vap-1 sequence upstream from the vap-1 start codon (ATG), including the putative vap-1 promoter region, and further included approximately 1.6 kB of vap-1 coding sequence. Primers were designed using the program MacVector. Primer F11C7.F30 consists of 24 base pairs of sequence from cosmid F11C7, and primer F11C7.R30 consists of 23 base pairs of sequence from cosmid F11C7. PCR was performed using AmpliTaq® (Perkin Elmer) and Taq Extender™ (Stratagene). The following PCR amplification conditions were used. Denaturing: temperature=95 degrees C., time=30 sec; Annealing: temperature=52 degrees C., time=1 min; Extension: temperature=72 degrees C., time=7 min. Thirty-five rounds of amplification were performed. The resulting ~6.5 kB fragment was gel purified using GeneClean® (BIO 101), digested with BalI, and the linearized fragment was again gel purified. Plasmid DNA was prepared from plasmid pPD95.75, which is well known in the art and is described at ftp.ciwemb.edu/PNF:byName:/FireLabWeb/FireLabInfo/FireLabVectors/ 1995_Vector_K it/using a QIAGEN® DNA miniprep kit according to the instructions of the manufacturer and digested with BalI. The linearized plasmid was gel purified using GeneClean. The 6.5 kB genomic vap-1 BalI fragment was ligated into the BalI-digested vector pPD95.75 so that the coding region was fused in frame to the GFP coding region contained in the vector, resulting in plasmid pV1GFP. A vap-1::nls-gfp reporter gene, in which expression of sequences encoding a nuclear localization signal upstream of GFP is driven by the vap-1 upstream regulatory region, was generated as follows. A fragment from the vap-1 genomic region containing 5 kB of sequence upstream from the start codon (ATG) and including the ATG from vap-1 but no other coding sequences was amplified by PCR from *C. elegans* wild type Bristol N2 genomic DNA using primers F11C7F31 (5'-ACGCGTCGACTCTCCAACCCATCAAA-CACC-3'=SEQ ID NO:13) and F11C7R31 (5'-CGCG-GATCCATCTGTGAAAATGAACGCACG-3'=SEQ ID NO:14). Note that here and elsewhere in the Examples, italics may be used to indicate restriction sites in primer sequences and/or to indicate portions of primers that are identical or complementary to different cosmids, plasmids, etc. Primers were designed by applicants by examining the sequence and employing criteria well known in the art for designing suitable primer sequences. Primer F11C7F31 includes a SalI site 5' of base pairs 8861–8842 of cosmid F11C7, and primer F11C7R31 includes a BamHI site 5' of base pairs 3907–3928 of cosmid F11C7. PCR was performed in an MJ Research tetrad thermal cycler using TaqPlus Precision (Cat. #600210), Stratagene, La Jolla, Calif. The following PCR amplification conditions were used. Denaturing: temperature=95 degrees C., time=30 sec; Annealing: temperature=60 degrees C., time=1 min; Extension: temperature=72 degrees C., time=5 min. Thirty-five rounds of amplification were performed.

Figure 5B:
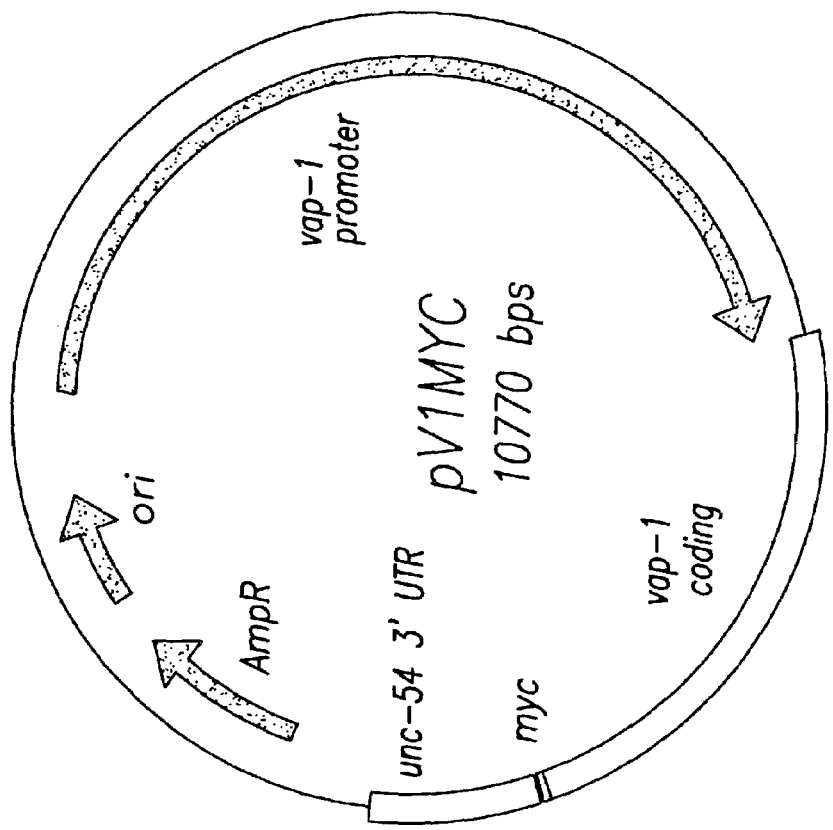
FIG. 5 illustrates plasmids pV1NLGFP (FIG. 5A) and pV1MYC (FIG. 5B) described in Examples 3 and 7.
Figure 5A:
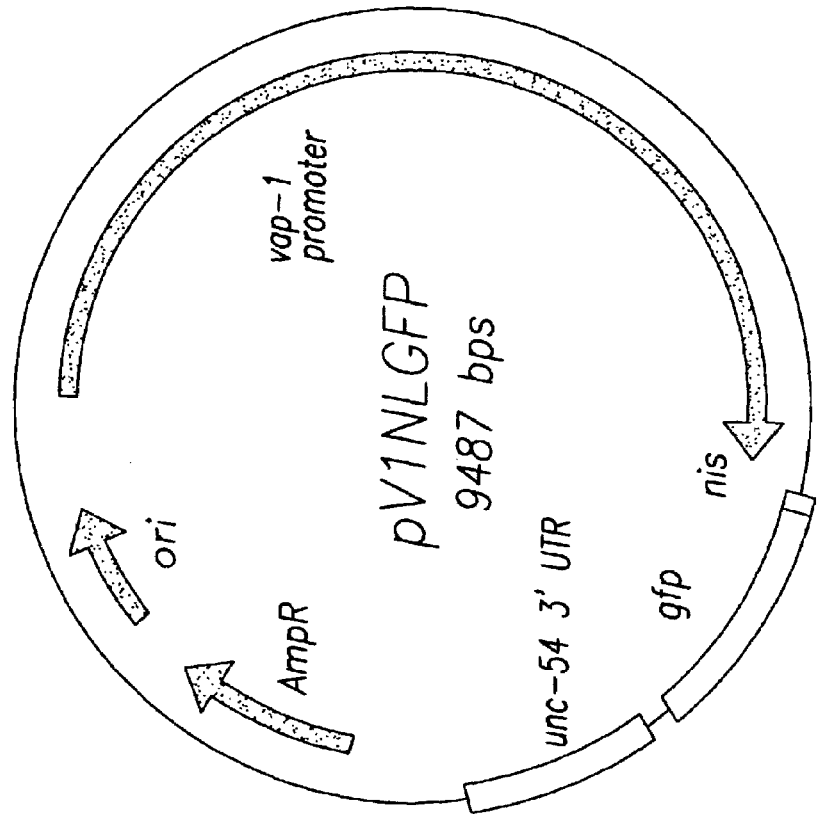

The PCR fragment was digested with SalI and BamHI and cloned between the SalI and BamHI sites of the vector pPD95.67, described at the Web site mentioned above. pPD95.67 includes the SV40 nuclear localization signal fused in frame to a sequence coding for a modified version of GFP, but lacks a promoter to drive expression of the nls-gfp sequences. The vector is designed such that insertion of a promoter-containing sequence into the polylinker upstream of the nuclear localization sequence results in a construct in which the inserted promoter drives expression of the nls-gfp sequence. In the case of the vap-1::nls-gfp reporter gene, the ATG from the vap-1 gene was supplied as part of the insert. Insertion of the SalI-BamHI vap-1 genomic fragment into pPD95.67 resulted in plasmid pV1NLGFP (shown in FIG. 5A).

Example 4

Construction and Analysis of Transgenic *C. elegans* Carrying vap-1::gfp and vap-1::nls-gfp Reporters Materials and Methods DNA was prepared from plasmids pV1GFP, pV1NLGFP, and pJM23 (Huang L S, Tzou P, and Sternberg P W, "The lin-15 locus encodes two negative regulators of *Caenorhabditis elegans* vulval development", *Molecular Biology of the Cell* 5: 395–411, 1994) using a QIAGEN® DNA miniprep kit according to the instructions of the manufacturer. To generate transgenic *C. elegans* carrying the vap-1::gfp reporter, the gonads of young adult lin-15 (n765ts) hermaphrodites were co-injected with 50 ng/μl each of plasmid pV1GFP and the lin-15 rescuing plasmid pJM23 essentially as described in Mello and Fire, "DNA Transformation" in *Methods in Cell Biology*, Vol. 43, referenced above. Potential transformants were grown at 20° C. Transformed animals were selected based on rescue of the multivulva (Muv) phenotype (i.e., non-transformed animals were viable but Muv whereas transformed animals were nonMuv). Transgenic *C. elegans* carrying the vap-1::nls-gfp reporter were generated by co-injecting 50 ng/µl each of plasmids pV1NLGFP and pJM23 and selecting transformants as described above. Transgenic worms were examined for GFP expression with epifluorescence or differential interference microscopy on an Axioskop 2 microscope (Zeiss). Images were captured using an Axiocam digital camera (Zeiss) and analyzed using Axiovision (Zeiss) and Adobe Photoshop software.

Results

Figure 6A:
FIG. 6A shows a fluorescence microscopy image of an adult transgenic *C. elegans* carrying the vap-1::nls-gfp fusion.
Figure 6B:
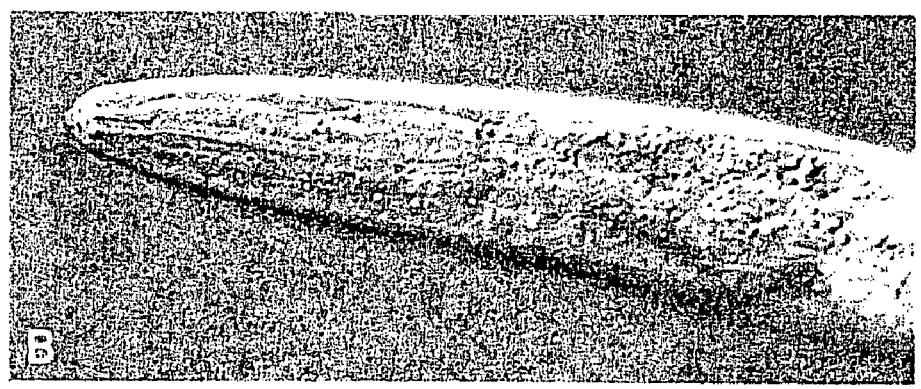
FIG. 6B shows a differential interference contrast (DIC) microscopy image of the same worm as in FIG. 6A.
Figure 6C:
FIG. 6C shows a fluorescence microscopy image of an adult transgenic *C. elegans* carrying the vap-1::myc fusion.

Transgenic *C. elegans* carrying either the vap-1::gfp (plasmid pV1GFP) or vap-1::nls-gfp fusion (plasmid pV1NLGFP) as an extrachromosomal array displayed GFP expression in the amphid sheath cells. FIG. 6 shows an adult transgenic *C. elegans* carrying the vap-1::nls-gfp fusion. Expression of the reporter is evident in the left amphid sheath cell in the fluorescence microscopy image presented in panel 6A. Panel 6B shows a differential interference contrast (DIC) image of the same worm. In these images anterior is to the left and dorsal is up.

Expression of the reporter can first be detected during the first larval stage and continues throughout the lifespan of the animal. Expression was observed in dauers and in starved animals in addition to animals grown under standard conditions.

Example 5

Construction of vap-2::gfp and vap-2::nls-gfp Reporter DNA Fragments

A 6.3 kB genomic fragment of vap-2 comprised of approximately 4.6 kB of sequence upstream from the vap-2 ATG and the first 1.7 kB of sequence including and downstream from the ATG (including the first 7 introns) was amplified by PCR from wild type N2 *C. elegans* genomic DNA (prepared according to standard methods) using primers T05A10F4 (5'-tggaaagcacaatcgaggtgg-3'=SEQ ID NO:15) and T05A10R3 (5'-acataccttgggtcctttggtggctgg-gaagtgtttgtttctc-3'=SEQ ID NO:16). All primers described in this Example were designed using the program PrimerFinder v.0.06, available at eatworms.swmed.edu/~tim/primerfinder/. Primer T05A10F4 consists of sequence complementary to base pairs 29,034–29,014 of cosmid T05A10 (the vap-2 gene is on the reverse strand). Primer T05A10R3 consists of sequence complementary to base pairs 67–47 of plasmid pPD95.75 and sequence identical to base pairs 22,784–22,806 of cosmid T05A10. The following PCR amplification conditions were used. Denaturing: temperature=95 degrees C., time=30 sec; Annealing: temperature=57 degrees C., time=1 min; Extension: temperature=72 degrees C., time=7 min. Thirty-five rounds of amplification were performed.

The vector pPD95.75, described at the Web site referenced above, was used as template to PCR amplify a 1.9 kB fragment containing the entire GFP coding region as well as the unc-54 3' UTR using primers GFPF1 (5'-ccaaaggac-ccaaaggtatgt-3'=SEQ ID NO:17) and GFPR2 (5'-tacaga-caagctgtgaccgtctc-3'=SEQ ID NO:18). Primer GFPF1 consists of sequences identical to base pairs 47–67 of pPD95.75. Primer GFPR2 consists of sequences complementary to base pairs 1978–1956 of pPD95.75. PCR conditions were as described for the vap-2 fragment.

The amplified fragments were joined using the splicing by overlap extension (SOEing) method (Horton, R M, et al., Gene splicing by overlap extension: tailor-made genes using the polymerase chain reaction, *Biotechniques*, 8(5):528–35, 1990) to produce an approximately 8.1 kB fragment containing vap-2 upstream and coding sequences fused in frame to sequences encoding GFP. Nested primers T05A10F3 and GFPR1 were used for the SOEing reaction. T05A10F3 consists of sequences complementary to base pairs 29,017–28,987 of cosmid T05A10. Primer GFPR1 consists of sequences complementary to base pairs 1934–1914 of pPD.75. Four amplification cycles were performed under the following conditions. Denaturing: temperature=93 degrees C., time 30 sec; Annealing: temperature=47 degrees C., time=1 min; Extension: temperature=72 degrees C., time=9 min. Thirty-two rounds of amplification were then performed under the following conditions. Denaturing: temperature=93 degrees C., time=30 sec; Annealing: temperature=53 degrees C., time=30 sec; Extension: temperature=72 degrees C., time=9 min. Fragments from multiple PCR reactions were pooled and purified using a QIAquick® PCR Purification kit (QIAGEN) according to the directions of the manufacturer.

A 4.6 kB genomic fragment of vap-2 comprised of sequences immediately upstream of the start codon and including the first eleven codons was amplified by PCR from wild type N2 *C. elegans* genomic DNA (prepared according to standard methods) using primers T05A10F4 (SEQ ID NO: 15) and T05A10R4 (5'-acataccttgggtcctttggaaaaa-gagtgacagcggaaag-3'=SEQ ID NO:19). Primer T05A10F4 consists of sequence complementary to base pairs 29,034–29,014 of cosmid T05A10 (the vap-2 gene is on the reverse strand). Primer T05A10R4 consists of sequence complementary to base pairs 67–47 of plasmid pPD95.67 and sequence identical to base pairs 24,427–24,447 of cosmid T05A10. The following PCR amplification conditions were used. Denaturing: temperature=95 degrees C., time=30 sec; Annealing: temperature=57 degrees C., time=1 min; Extension: temperature=72 degrees C., time=7 min. Thirty-five rounds of amplification were performed.

The vector pPD95.67, which is well known in the art and is described at ftp.ciwemb.edu/PNF:byName:/FireLabWeb/FireLabInfo/FireLabVectors/1995_Vector_K it/was used as template to PCR amplify a 2.0 kB fragment containing the entire nuclear localization signal (nls) and GFP coding regions as well as the unc-54 3' UTR using primers GFPF1 (SEQ ID NO:17) and GFPR2 (SEQ ID NO:18). Primer GFPF1 consists of sequences identical to base pairs 47–67 of pPD95.67. Primer GFPR2 consists of sequences complementary to base pairs 2023–2001 of pPD95.67. PCR conditions were as described for the vap-2 fragment.

The amplified fragments were joined using the splicing by overlap extension (SOEing) method referenced above to produce an approximately 6.5 kB fragment containing vap-2 upstream and coding sequences fused in frame to sequences encoding the SV40 nuclear localization signal (nls) and GFP. Nested primers T05A10F3 (5'-gtggaagtcaatgggcagatt-3'=SEQ ID NO:20) and GFPR1 (5'-gttttcaccgtcatcaccgaa-3'=SEQ ID NO:21) were used for the SOEing reaction. T05A10F3 consists of sequences complementary to base pairs 29,017–28,987 of cosmid T05A10. Primer GFPR1 consists of sequences complementary to base pairs 1979–1959 of pPD.67. Four amplification cycles were performed under the following conditions. Denaturing: temperature=93 degrees C., time=30 sec; Annealing: temperature=47 degrees C., time=1 min; Extension: temperature=72 degrees C., time=9 min. Thirty-two rounds of amplification were then performed under the following conditions. Denaturing: temperature=93 degrees C., time=30 sec; Annealing: temperature=53 degrees C., time=30 sec; Extension: temperature=72 degrees C., time=9 min. Fragments from multiple PCR reactions were pooled and purified using a QIAquick® PCR Purification kit (QIAGEN) according to the directions of the manufacturer.

All PCR reactions were performed in an MJ Research tetrad thermal cycler using TaqPlus Precision (Cat. #600210), Stratagene, La Jolla, Calif. (Note: Although the particular PCR reactions described in this Example were performed using TaqPlus Precision, applicants have subsequently discovered that higher yields of product may be obtained using the Expand™ Long Template PCR System from Roche (Cat. #1681834), which contains a mixture of Taq Polymerase and Pwo Polymerase.)

Example 6

Construction of Transgenic C. elegans Carrying vap-2::gfp and vap-2::nls-gfp Reporter DNA Fragments Materials and Methods DNA was prepared from plasmid pJM23, referenced above, using a QIAGEN® DNA miniprep kit according to the instructions of the manufacturer. To generate transgenic C. elegans carrying the vap-2::gfp reporter, the gonads of young adult lin-15 (n765ts) hermaphrodites were co-injected with 35 ng/μl of the appropriate PCR SOEing fragment and 50 ng/μl of the lin-15 rescuing plasmid pJM23 essentially as described in Mello and Fire, "DNA Transformation" in *Methods in Cell Biology*, Vol. 43, referenced above. Potential transformants were grown at 20° C. Transformed animals were selected based on rescue of the multivulva (Muv) phenotype (i.e., non-transformed animals were viable but Muv whereas transformed animals were nonMuv). Transgenic worms were examined for GFP expression with DIC and epifluorescence microscopy.

Example 7

Construction of vap-1::myc Reporter Construct

An ~7.4 kB kB genomic fragment of vap-1 containing 4.8 kB of sequences immediately upstream of the start codon and the entire coding region except for the stop codon was amplified by PCR from wild type N2 C. elegans genomic DNA (prepared according to standard methods) using primers BW1F (5'-cattttcaggaggacccttggtgatgtgaattcttatggtggc-3'=SEQ ID NO:22) and BW2R (5'-ggcgagctcttaaaggtcctcct-cagaaatgagttttgttcagggatGacacataatgcttcag-3'=SEQ ID NO:23) designed using the program PrimerFinder referenced above. Primer BW1F consists of sequences identical to base pairs 112–132 of plasmid pPD49.26 (well known in the art and described at the Web site mentioned above) and sequences complementary to base pairs 8739–8718 of cosmid F11C7 (the vap-1 gene is on the reverse strand). Primer BW2R was designed such that the resulting PCR product encoded a fusion between VAP-1 and the Myc epitope tag EQKLISEEDL (SEQ ID NO:24). BW2R contains (in a 5' to 3' direction), the sequence GGC, a SacI site, sequences complementary to a stop codon (TTA), sequences complementary to a sequence encoding the Myc epitope tag, and sequence identical to base pairs 1445–1467 of cosmid F11C7 with a silent A to G change at base pair 1451. PCR was performed using the Expand™ Long Template PCR System from Roche (Cat. #1681834). Nine cycles of PCR amplification under the following conditions were performed: Denaturing: temperature=92 degrees C., time=10 sec; Annealing: temperature=51 degrees C., time=30 sec; Extension: temperature=68 degrees C., time=5.5 min. Following this round 19 further cycles of amplification were performed in which the extension time was increased by 20 sec each cycle while the other conditions remained the same.

Multiple independent fragments were cloned into plasmid pCR2.1 TOPO® (Invitrogen) using a TA cloning kit according to the directions of the manufacturer. The ~7.4 kB vap-1/myc insert was released from the resulting plasmid by digesting with SpeI (cuts in the pCR2.1 polylinker sequences flanking the 5' end of the insert) and SacI (cuts immediately 3' of the sequences encoding the Myc epitope tag).

DNA was prepared from plasmid pPD49.26, referenced above, using a QIAGEN® DNA midiprep kit according to the instructions of the manufacturer. The plasmid was digested with NheI and SacI, and the linearized vector backbone was gel purified using GeneClean®. The ~7.4 kB vap-1/myc fragment was cloned into the pPD49.26backbone to create plasmid pV1Myc (shown in FIG. 5B). (Note that NheI and SpeI have compatible overhangs but that neither site is regenerated after the ligation.)

Example 8

Construction and Analysis of Transgenic Nematodes Carrying the vap1::myc Reporter Materials and Methods DNA was prepared from plasmids pDP#MM016B (unc-119 rescuing plasmid) and pV1Myc (vap-1::myc reporter) using a QIAGEN® DNA midiprep kit according to the instructions of the manufacturer. To generate transgenic C. elegans carrying the vap-1::myc reporter, the gonads of young adult unc-119 (e2498) hermaphrodites were co-injected with 50 ng/μl of each plasmid as described in Mello and Fire, "DNA Transformation" in *Methods in Cell Biology*, Vol. 43, referenced above. Potential transformants were grown at 20° C. Transformed animals were selected based on rescue of the uncoordinated phenotype (i.e., non-transformed animals were uncoordinated whereas transformed animals were not). Injections were performed using several independent versions of plasmid pV1Myc to control for possible PCR errors.

Whole mount fixation of larvae and adults was performed using the modified Ruvkun and Finney fixation protocol described in Chapter 16 (Immunoflourescence Microscopy), pp. 373–375 in Epstein, H. and Shakes, D. (eds.) Methods in Cell Biology—*Caenorhabditis elegans*: Modern Biological Analysis of an Organism, Academic Press, San Diego, 1995. Worms were stained with a 1:200 dilution of the 9E10 anti-Myc monoclonal antibody (Santa Cruz Biotechnology, Santa Cruz, Calif.) followed by a 1:1000 dilution of a FITC-conjugated goat anti-mouse secondary antibody (Cappel™ Products, ICN Pharmaceuticals, Costa Mesa, Calif.).

Transgenic worms were examined for expression of the transgene with epifluorescence and differential interference contrast (DIC) microscopy on an Axioskop 2 microscope (Zeiss). Images were captured using an Axiocam digital camera (Zeiss) and analyzed using Axiovision (Zeiss) and Adobe Photoshop software.

Results

Transgenic C. elegans carrying the vap-1::myc fusion (plasmid pV1Myc) displayed expression in the amphid sheath cells, consistent with the expression pattern seen with the vap-1::nls-gfp reporter (Example 4). FIG. 1, panel C shows an adult transgenic C. elegans carrying the vap-1::myc fusion. In this image anterior is to the left and dorsal is up. Expression of the reporter is evident in the left amphid sheath cell. The staining is punctate and more concentrated at the end of the process, consistent with intracellular localization in secretory vesicles.

Example 9

Construction and Analysis of Transgenic Nematodes Carrying an Integrated vap-1::nls-gfp or vap-1::myc Reporter Materials and Methods Transgenic C. elegans carrying the vap-1::nls-gfp reporter (plasmid pV1NLGFP) as an extrachromosomal array were generated as described in Example 4. Ten standard 6 cm agar plates seeded with bacteria each containing 5 L4 worms were exposed to UV irradiation (254 nm) using a Stratagene UV Stratalinker set at 300 µjoules (×100), i.e., 30 millijoules/cm$^2$. Ten plates were starved for 1 week at 20° C. and the remaining 10 plates were starved at 15° C. (Since an integrant was obtained from the 20° C. plates, the 15° C. plates were never screened.) Each plate was then chunked to a fresh plate seeded with bacteria (i.e., a small chunk of agar with worms on the surface was transferred to a fresh plate). One day later 15 L4 worms from each 20° C. plate were transferred to individual plates, which were stored at 20° C. for one generation time. The independent lines generated on these plates were scored by identifying those plates on which 100% of the worms expressed vap-1::nls-gfp (i.e., displayed GFP fluorescence when examined using epifluorescence microscopy) and 100% were non-Muv (since the vap-1::nls-gfp reporter was coinjected with a lin-15 rescuing plasmid into lin-15 mutant worms). A single vap-1::nls-gfp integrant was obtained which was outcrossed four times to wild type (N2) by following the green GFP fluorescence.

To generate an integrated line bearing the vap1::myc reporter, transgenic C. elegans carrying the vap-1::myc reporter (plasmid pV1Myc) as an extrachromosomal array were generated as described in Example 8. Twenty standard 6 cm agar plates seeded with bacteria each containing 5 L4 worms per were exposed to UV irradiation as described above. One day later 15 L4 worms from each 20° C. plate were transferred to individual plates, which were stored at 20° C. for one generation time. The independent lines generated on these plates were scored by identifying those plates on which 100% of the worms were non-Unc (since the vap-1::myc reporter was originally coinjected with an unc-119 rescuing plasmid into unc-119(e2498) mutant worms). A single vap-1::myc integrant was obtained. The integrant was outcrossed four times to an unc-119(e2498) strain by following rescue of the Unc phenotype. The unc-119(e2498) strain used for the outcross was previously outcrossed 4 times to wild type (strain N2) by following the Unc phenotype.

Results

The GFP expression pattern observed in the vap-1::nls-gfp integrant was very similar to that observed in the transgenic line carrying vap-1::nls-gfp as an extrachromosomal array (See Example 4), except that fluorescence was somewhat brighter in the integrated line and could be detected earlier, beginning midway through embryogenesis. In adults grown under standard conditions, GFP expression was observed in the amphid sheath cells. Expression was also observed in dauers and in starved animals.

Example 10

Secretion Assay to Confirm that VAPs are Secreted into the External Environment

Materials and Methods

Worms (either animals bearing the vap-1::myc transgene or unc-119 (e2498) mutants rescued with plasmid pPD#MM016B as a negative control) were cultured in S basal medium (recipe below) containing HB101 bacteria as a food source for 4–5 days as described below. The worms were separated from the media by centrifugation and washed several times in S basal media. Worms were then resuspended in 50 ml of axenic media (recipe below) and cultured overnight (~20 h). A vessel containing only axenic media without worms was maintained under identical conditions as a control. The worm density in both the vap-1::myc and unc-119 cultures was approximately 50,000 per ml. It was estimated that 50–70% of the worms carry the transgene.

After overnight incubation in axenic media, the worms and media were separated by centrifugation (see below for details) and the media were concentrated using Centriprep 30 concentrators (see below for details). Media from the two worm cultures were concentrated 56×, and media from the axenic media control was concentrated 35×. Comparable amounts of sample were loaded in each lane of a 10% SDS-PAGE gel (based on fold concentrated rather than on total protein). For the media samples from both worm cultures, it was estimated that each sample represented concentrated secretions from approximately 10,000 transgene-bearing worms.

Immunoblotting using a commercially available 9E10 anti-Myc antibody (Santa Cruz Biotechnology, Santa Cruz, Calif.) was used to confirm that C. elegans VAP-1 is secreted into the external environment and to examine the effects of treatment with 4,7-phenanthroline on secretion of the VAP-1-Myc fusion protein. The samples were loaded on SDS-polyacrylamide gels, separated by electrophoresis, and transferred to nitrocellulose. Membranes were blocked, incubated with anti-Myc antibodies diluted according to the manufacturer's instructions, washed and incubated with horseradish peroxidase-conjugated secondary antibody, and finally developed for visualization with enhanced chemiluminescence reagents. Similar immunoblotting assays are used for detection of other fusion proteins that include the Myc epitope tag.

To determine the effect of 4,7 phenanthroline on secretion of the VAP-1-Myc fusion protein, worms (either transformation control or bearing the vap-1::myc transgene) were cultured in 24 well plates (in a manner similar to the 96 well scaledown protocol described below) in axenic media in the presence of various concencentrations of 4,7 phenanthroline for 16 hours. Conditioned media from approximately 10,000 worms per culture was concentrated using Microcon 30 filters and subjected to immunoblotting. VAP-1-Myc fusion protein was detected with anti-Myc antibody as described above.

Culturing and Harvesting *C. elegans* in Liquid
(modified from Koelle protocol, "Liquid culture of worms", available at cobweb.dartmouth.edu/cgi-bin/cgiwrap/~ambros/protocol.cgi?id=22)

Preparation of HB101 Bacteria
Prepare 5L Sigma Terrific Broth in 5 2L flasks
Innoculate each flask with ~4 ml HB101 culture (grown O/N 37 shaker in LB)
Grow O/N in 37 degree shaker, 240 rpm. (Can store at 4 degrees until ready to use)
Aliquot into 500 ml centrifuge bottles (Oakridge polycarbonate, with adapters)
Spin in Sorvall RC3B floor centrifuge with H-6000 A rotor at 4000 rpm (4657×g). Set brake at 6, rotor cooled to 4 degrees, for 15 minutes. Should have a firm bacterial pellet, clear supernatant.
Decant supernatant, pour in more bacterial culture. Repeat spin. Two full spins of 6 500 ml bottles should be enough to pellet all 5 L.
Resuspend bacterial pellets in S complete, ~3 ml per bottle.
Yield: ~70 ml containing 60 g bacteria.
Store at 4 degrees up to two weeks or −20 degrees indefinitely Worm Culture in S Medium with HB101 Bacterial Food Source
Prepare 500 ml Complete S medium. For each culture, grow one 6 cm plate of worms to starvation; should be predominantly L1's.
Aliquot 50 ml S complete into sterile 125 ml flask
Wash starved worms into flask using 1–2 ml S complete.
Add 1.25 ml HB 101 suspension
Grow on platform shaker at 200–225 rpm. (Done at room temperature, was 23–25 degrees)
After two days, add another 2.5 ml HB101 suspension.
Harvest culture after 4–5 days.

Harvesting Supernatant
Keep centrifuges at 4 degrees.
Take an aliquot of the culture to check bacteria levels, stages of worms and density
Pour cultures into 50 ml conical tubes
Spin at 1700 rpm (665×g) in Beckman GH 3.8 rotor, brake low, for 3 minutes at speed
Remove to ice to keep worms from swimming up.
Check supernatant to be sure no worms remain.
Remove super by pipeting and discard.

Harvesting *C. elegans* for Repeated Culture
Keep centrifuges at 4 degrees.
Resuspend worms and bacteria pelleted after first spin, bring to at least 7.5 ml with ice-cold 0.1M NaCl
Add equal amount ice-cold 60% sucrose, invert to mix.
Spin in Beckman GH 3.8 rotor at 650 rpm (~100×g) 5 min, no brake.
Quickly remove layer of worms from top of tubes into ~25 ml ice-cold 0.1M NaCl. (Sucrose solution damages worms, so work quickly)
Repeat 5 min spin
Transfer worm pellets to sterile 15 ml conicals and bring to 10 ml with fresh S complete
Rock by hand or rocker ~3 min
Pellet worms and repeat wash Transfer pelleted worms to 50 ml each S complete in sterile 125 ml flasks
Shake on room temperature platform @ 200–225 rpm one hour to allow worms to excrete bacteria
Decant to 50 ml conicals, pellet, and wash 1×
Transfer worms to 50 ml each axenic media (see recipe below) in sterile 125 ml flasks
Shake on room temperature platform @ 200–225 rpm 24 hr to allow worms to secrete into fresh media Harvesting Axenic Media
Keep centrifuges at 4 degrees.
Decant cultures into 50 ml conicals
Spin as before to pellet worms
May be necessary to decant super and re-spin to pellet all worms
Pipet away super, leaving generous layer behind to ensure no worms picked up
Store at 4 degrees until ready to concentrate Concentrating Supernatant
Keep centrifuges at 4 degrees.
Keep concentrators on ice when they are out of centrifuge.
Using Centriprep-30 concentrators (Amicon/Millipore), the maximum loading volume is 15 ml, the MW cutoff to retain proteins is 30,000 Daltons. Larger or smaller filters may be needed for different applications, depending on the target protein(s). Concentrators can be refilled with repeated aliquots of media to concentrate, but they can't be reused on another occasion.
Fill concentrators with 15 ml supernatant, balanced in pairs
Spin in Beckman GH3.8 rotor at 2250 rpm (1500×g) for 15 min, brake low.
Decant filtrate into 50 ml conical tube and refill concentrator with fresh supernatent.
Repeat spin for 15 min. Check each time to be sure that filtrate and retentate have reached equilibrium heights; slow flow rate, due to high protein concentrations in medium or low temperature, may require longer spins to counteract.
Spin as before to continue concentrating. If filtrate and retentate won't reach equilibrium after repeated spins, membrane may have become clogged. Must switch to new concentrators.
In Centriprep-30 concentrators, dead-stop is 0.6–0.7 ml; can bring total retentate volume to between 0.6 to 1.2 ml, depending on sample.
When desired level of concentration is reached, pipet retentate into 1.5 ml microfuge tubes (on ice), and store at −20 degrees.

S Medium Recipe—500 mL:
2.9 g NaCl
25 ml 1M $KHPO_4$, pH 6.0
472 ml dH2O
0.5 ml 5 mg/ml cholesterol in 95% EtOH
autoclave
sterilely supplement with:
1.5 ml 1M $MgSO_4$
1.5 ml 1M $CaCl_2$
5 ml trace metal solution
5 ml 1M Kcitrate, pH 6.0
5 ml 100× PSN antibiotic mixture, Gibco
5 ml 100× Nystatin suspension, Gibco Axenic Medium Recipe-100 ml:
3 g Difco Bactopeptone (3%)
3 g Difco Yeast Extract (3%)
Add dH2O to 100 ml, autoclave Add 1 ml autoclaved 5% stock Sigma hemoglobin #H2750 in 0.1M KOH (0.05%)

Results

Figure 7:
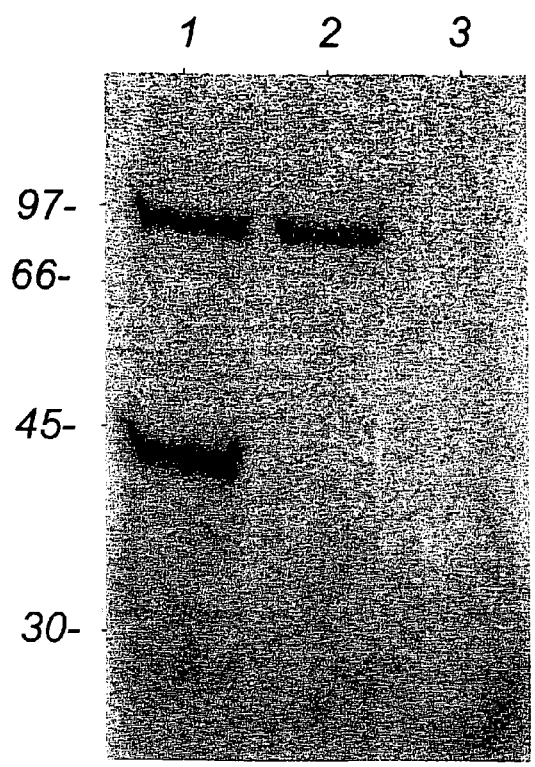
FIG. 7 shows an immunoblot demonstrating detection of secreted *C. elegans* VAP-1 in culture medium.

Secretion of VAP-1-Myc Fusion Protein and Inhibition of Secretion by Treatment with 4,7 Phenanthroline FIG. 7 shows an immunoblot demonstrating that the VAP-1-Myc fusion protein is secreted into the external environment. Lane 1 is concentrated media from the vap-1::myc culture, lane 2 is concentrated media from the unc-119 control and lane 3 is concentrated axenic media. The band at approximately 45 kD in lane 1 represents VAP-1-Myc and is consistent with the predicted molecular weight of VAP-1-Myc of slightly less than 46 kD. The identity of the nonspecific band at 97 kDa is unknown but appears reproducibly in similar experiments.

Figure 8:
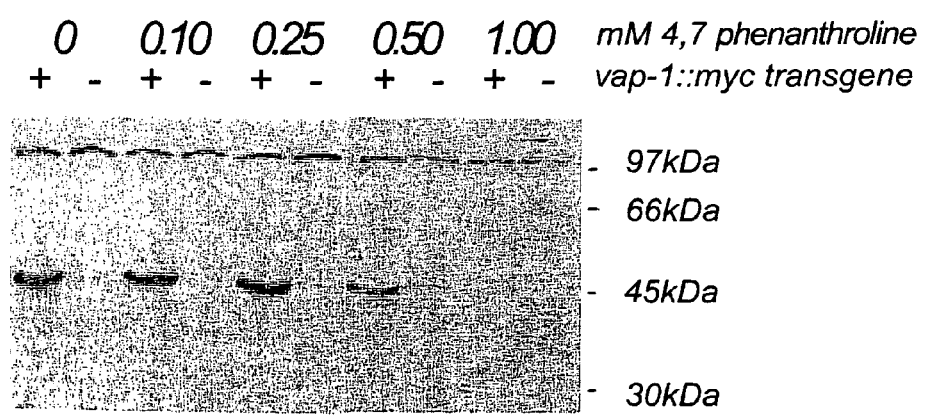
FIG. 8 shows an immunoblot depicting the effect of 4,7 phenanthroline on secretion of the VAP-1-Myc fusion protein by *C. elegans* bearing the vap-1::myc transgene.

FIG. 8 shows an immunoblot demonstrating that secretion of the VAP-1-Myc fusion protein is inhibited by treatment with 4,7 phenanthroline, a known inhibitor of release of the secretory protein ASP-1 in hookworms, in a dose-dependent fashion. Worms bearing the vap-1::myc transgene (+) or lacking the transgene (−) were incubated in the indicated concentration of 4,7 phenanthroline for 16 hours.

Secretion Assay Scaledown

The secretion assay was scaled down for performance in 96-well plates as follows: Worms carrying the integrated vap-1::myc transgene were cultured in 50 ml S basal/HB101 for a generation, washed and resuspended in axenic media at a density of approximately 100,000/ml as described above. The worms were then distributed into 96-well plates and incubated overnight. After concentrating the media using Microcon 30 filters (Amicon), the samples were loaded on SDS-PAGE gels, blotted, and detected as described above. Concentrated medium from an estimated 5000 transgene-bearing worms was sufficient for the VAP-1::Myc fusion protein to be detected readily.

Example 11

Identification of an Inhibitor of a Nematode Secretion Pathway by Screening a Compound Library Materials and Methods Briefly, the screen is performed by dispensing worms into multiwell plates, adding compound, removing culture supernatant at a predetermined time, and performing an antibody-sandwich ELISA to detect secreted VAP-1-Myc using an anti-Myc capture antibody and a polyclonal anti-VAP antibody followed by an enzyme-conjugated secondary antibody for detection (although of course a monoclonal antibody that recognizes VAP-1 can also be used). Protocols for antibody-sandwich ELISAs are well known in the art. For a nonlimiting example see, Unit 11, "Immunology" in *Current Protocols in Molecular Biology*, Wiley & Sons, 1987, with subsequent supplements, and see Unit 11.2, "Enzyme-Linked Immunosorbent Assays" in particular.

The polyclonal anti-VAP-1 antibody is generated using standard immunological techniques that are well known in the art such as those described in Harlow and Lane (Antibodies: A Laboratory Manual, Cold Spring Harbor Laboratory, New York, 1988) and discussed above. Antibodies may be generated, for example, using full-length recombinant VAP-1, a VAP-1 fusion protein (e.g., GST-VAP-1), or one or more peptides derived from the VAP-1 sequence as antigens.

The screen may employ compounds from the DIVERSet library discussed above, available from ChemBridge corporation, or any of a number of other libraries. The compounds are dispensed in a microwell format diluted in DMSO at a concentration of 5–20 mM and dispensed for use in screens and assays as needed.

Transgenic *C. elegans* carrying an integrated vap-1::myc reporter fusion are generated as described in Examples 7 or 8. In one embodiment of the invention, on day 1 of the screen between 10 and 20 worms per well (L4 larvae) are dispensed into 96 well plates in a solution of NGM medium or M9 buffer, using either a Multidrop 384 LabSystems (Helsinki, Finland; www.labsystems.fi/) dispenser or, where a more exact number of worms is desired, a COPAS machine (produced by Union Biometrica, Inc., Somerville, Mass. [www.unionbio.com]). The buffer or medium contains a predetermined amount (measured as OD/ml) of HB101 or OP50 bacteria sufficient to support a subsequent generation of progeny. Compounds are then added with a multichannel pipetter (although an automated dispenser could also be used). A volume of 0.5 µl is dispensed into each well into a volume of 50 µl to achieve a final concentration of 50–200 µM of compound and 1% DMSO. Plates are mixed to disperse compound and then incubated in a humidified chamber at 20° C.

Supernatants are collected at a time ranging from 3 to 7 days from the beginning of the assay, by which time the number of worms per well is approximately 2,000, assuming that the compound does not negatively affect *C. elegans* growth or reproduction. Before removing the supernatants, wells are scored for bacterial clearance to identify compounds that do have such effects since such compounds, regardless of their effects on secretion, may be potential anti-nematicides. Bacterial clearance is measured, for example, using a plate reader to measure the OD of the medium in each well. Supernatants are processed as described below.

In a second embodiment of the invention, a predetermined number of worms ranging from several hundred to several thousand is dispensed into 96 well plates in a solution of NGM medium, M9 buffer, or axenic media (if necessary) using either a Multidrop 384 LabSystems dispenser or, if necessary, a manual multichannel pipetter. Compounds are dispensed as described above. Supernatants (media or buffer) are collected at a period of time ranging between approximately 4 and 24 hours following addition of compound and are processed as described below. Wells may be scored visually to determine whether compounds affect *C. elegans* viability.

For detection of secreted VAP-1-Myc, some or all of the supernatant is removed from the wells. To facilitate the removal of supernatant while leaving worms behind, the screen may be performed using v-bottom multiwell plates. If worms are cultured and spun down in such plates and kept on ice they remain at the bottom of the well. Alternatively, multiwell plates that contain a filter in each well may be used, and supernatant removed from the side of the filter without the worms.

Supernatants are added to the wells of plastic microtiter plates (e.g., 384 wells or greater) that were previously coated with anti-Myc antibodies (e.g., 9E10 monoclonal anti-Myc antibody from Santa Cruz Biotechnology) and incubated for a period of time greater than 2 hours at room temperature. Recombinant VAP-1-Myc protein serves as a positive control. After washing to remove unbound material, anti-VAP-1 antibody is added to the wells at a concentration of between approximately 0.2 to 10 µg/ml and incubated for greater than 2 hours at room temperature. After washing to remove unbound antibody, a solution containing enzyme conjugated (e.g., alkaline phosphatase-linked) secondary antibody is added to wells according to the manufacturer's directions (typically to a final concentration between 25 and 500 ng/ml) and incubated for greater than 2 hours at room temperature. After washing to remove unbound antibody, the appropriate substrate solution (e.g., NBT and BCIP in the case of an alkaline phosphatase conjugated secondary antibody) is added to wells, and plates are incubated at room temperature to allow color development. Plates are scored using a microtiter plate reader equipped with appropriate filters. Color development indicates the detection of VAP-1-Myc, and thus wells exhibiting reduced color development (e.g., relative to wells corresponding to wells in the screening plate to which no compound was added) correspond to wells in the screening plates that contain a candidate inhibitor of VAP-1 secretion. The above steps (e.g., addition of reagent solutions, washing, etc., may be performed using a multichannel pipette or using microplate dispensers, washers, etc., such as those available from LabSystems.

Note that numerous variations on and alternatives to the above example will be evident to one of ordinary skill in the art. The screen can be performed using worms grown in plates with more or fewer than 96 wells (e.g., 24 wells, 384 wells, etc.). The detection method can employ a single enzyme-conjugated antibody that binds to VAP-1-Myc and rather than both a primary antibody that binds to VAP-1-Myc and a secondary enzyme-conjugated antibody that binds to the primary antibody. Instead of using an antibody-sandwich ELISA to detect secreted VAP-1 an indirect ELISA may be used, in which supernatants are removed from the screening wells and adsorbed to the wells of fresh microtiter plates, followed by addition of anti-Myc antibody and then enzyme-conjugated secondary antibody and appropriate substrates for detection.

In any of the above assays a variety of detection systems may be used including enzyme-conjugated antibodies, antibodies conjugated to fluorescent molecules, etc. Such detection systems and methods for their use are well known to one of ordinary skill in the art.

Example 12

Assessing Effects of Candidate Secretion Inhibitor on Secretion of ASP-1 by *A. caninum*

This example describes a procedure for determining the effects of a compound identified as an inhibitor of a nematode secretion pathway identified using the screen of the previous example, on secretion of the excretory/secretory protein ASP-1 by the parasitic nematode species *A. caninum* (hookworm). Such a compound is referred to herein as a candidate compound. The method employs an in vitro model in which the resumption of feeding is used as a marker for the transition from the free-living L3 to the developing parasitic L3 as described by Hawdon, et al., *J. Biol. Chem.*, 271, 6672–6678, 1996, and all citations to Hawdon within this example refer to this article.

As mentioned above, ASP-1 is the major protein released by hookworm L3 that have been activated to resume development and feeding. To assess the effects of a candidate compound on ASP-1 secretion, *A. caninum* are maintained as described previously (Hawdon and Schad, *Exp. Parasitol.*, 77, 489–491, 1993), and L3 larvae are collected from 1–4 week coprocultures and activated by the addition of an ultrafiltrate of canine serum and S-methylglutathione to the culture medium as described in Hawdon, et al., *J. Biol. Chem.*, 271, 6672–6678, 1996. Individual wells containing approximately 6,000 L3 are incubated with the activation stimulus for 30 min, 1, 4, 12, and 24 hours in the presence or absence of the candidate compound (i.e., in those wells to which the candidate compound is added, it is added at the same time as the stimulus). Candidate compound concentrations ranging from approximately 5 µg/ml to 1 mg/ml are tested. Nonactivated L3 incubated for 24 hours in the absence or presence of the candidate compound are used as a negative control. The compound 4,7-phenanthroline (0.5 mM final concentration in culture medium), a known inhibitor of both feeding and ASP-1 release (see Hawdon), is used as a positive control for both feeding inhibition and inhibition of ASP-1 release.

Following incubation, the ES products are harvested and concentrated by ultrafiltration. The presence and approximate amount of ASP-1 in ES products is assessed by Western blotting according to the protocol described by Hawdon, using antisera raised against recombinant ASP-1. To determine whether the candidate compound inhibits resumption of refeeding in addition to potential effects on ASP-1 secretion, the percentage of feeding L3 is determined following the 24 hour incubation by monitoring ingestion of fluorescein isothiocyantate-labeled bovine serum albumin as described by Hawdon.

To determine whether the candidate compound can inhibit ongoing secretion following activation, wells containing approximately 6,000 L3 are incubated in the presence of the activation stimulus for 1 hr and the candidate compound is then added. ES products are collected at 30 min, 1, 4, 12, and 24 hours following addition of the candidate compound. A well containing activated L3 to which the compound has not been added is used as a positive control. The presence and approximate amount of ASP-1 in ES products is assessed by Western blotting. The percentage of feeding L3 is determined at following the 24 hour incubation as described above.

A compound that reduces ASP-1 secretion and/or reduces the percentage of L3 that resume refeeding upon stimulation is identified as a potential anti-nematode compound.

We claim:

1. A transgenic *C. elegans* nematode, the cells of which contain a transgene comprising a regulatory element of the *C. elegans vap*-1 gene operably linked to a DNA sequence encoding a detectable marker, wherein the detectable marker is expressed in a *C. elegans* amphid sheath cell.

2. The transgenic nematode of claim 1, wherein the transgene further comprises at least a portion of the coding sequence of the *C. elegans vap*-1 gene.

3. The transgenic nematode of claim 2, wherein the transgene further comprises at least a portion of an intron from the *C. elegans vap*-1 gene.

4. The transgenic nematode of claim 2, wherein the transgene further comprises at least a portion of the 3' untranslated region from the *C. elegans vap*-1 gene.

5. The transgenic nematode of claim 2, wherein the coding sequence of the *C. elegans vap*-1 gene is in frame with the sequence encoding the detectable marker.

6. The transgenic nematode of claim 1, wherein the transgene is contained in a chromosome.

7. The transgenic nematode of claim 1, wherein the transgene is extrachromosomal.

8. The transgenic nematode of claim 5, wherein the transgene comprises an integrated array comprising a second regulatory element operably linked to a second copy of a DNA sequence encoding the detectable marker.

9. The transgenic nematode of claim 8, wherein the second regulatory element directs expression of the detectable marker in a substantially different population of cells to that in which the regulatory element of the *C. elegans* vap-1 gene directs expression of the detectable marker.

10. The transgenic nematode of claim 1, wherein the detectable marker is selected from the list consisting of: a fluorescent polypeptide, a chemiluminescent polypeptide, an epitope tag, and an enzyme.

11. The transgenic nematode of claim 1, wherein the detectable marker is selected from the list consisting of: green fluorescent protein, luciferase, chloramphenicol acetyl transferase, xanthine-guanine phosphoribosyl transferase, beta-galactosidase, horseradish peroxidase, alkaline phosphatase, a Myc tag, and an HA tag.

12. The transgenic nematode of claim 1, wherein the detectable marker comprises a variant of a marker selected from the list consisting of: green fluorescent protein, luciferase, chloramphenicol acetyl transferase, xanthine-guanine phosphoribosyl transferase, beta-galactosidase, horseradish peroxidase, alkaline phosphatase, a Myc tag, and an HA tag, wherein the variant is detectable using the same detection means by which the marker of which it is a variant is detectable.

13. The transgenic nematode of claim 1, wherein the regulatory element comprises a 5' regulatory region extending up to 10 kB in a 5' direction from the start codon of the *C. elegans* vap-1 gene.

14. A method of generating a nematode comprising steps of:
  (a) selecting a parasitic nematode secretory protein;
  (b) identifying a *C. elegans* homolog of the protein selected in step (a);
  (c) identifying a nucleic acid sequence comprising a regulatory region of a *C. elegans* gene encoding the *C. elegans* homolog identified in step (b); and
  (d) generating a transgenic *C. elegans* nematode, wherein cells of the transgenic nematode comprise a nucleic acid sequence including the identified regulatory region operably linked to a nucleic acid sequence encoding a detectable marker, wherein the regulatory region directs expression in a pharyngeal gland cell or amphid sheath cell and the detectable marker is expressed in a pharyngeal gland cell or amphid sheath cell.

15. The method of claim 14, wherein the parasitic nematode is a member of an order selected from the group consisting of the *Strongylida, Rhabditida, Ascaridida, Spirurida, Oxyurida, Enoplida, Tylenchida,* or *Dorylaimida* nematode orders.

16. The method of claim 14, wherein the regulatory region comprises a promoter of the *C. elegans* homolog identified in step (b).

17. The method of claim 14, wherein the nucleic acid sequence of step (d) includes at least a portion of the coding sequence of a gene encoding the *C. elegans* homolog of part (c).

18. The method of claim 17, wherein the nucleic acid sequence of step (d) includes a signal sequence.

19. The method of claim 17, wherein the nucleic acid sequence of step (d) includes at least a portion of an intron from a gene encoding the *C. elegans* homolog of part (c).

20. The method of claim 17, wherein the nucleic acid sequence of step (d) includes at least a portion of the 3' untranslated region from a gene encoding the *C. elegans* homolog of part (c).

21. The method of claim 14, wherein the regulatory region is sufficient to direct expression of the nucleic acid of step (d).

22. The method of claim 14, wherein the parasitic nematode is a member of a genus selected from the list consisting of the *Haemonchus, Oestertagia, Trichostrongylus, Cooperia, Dictyocaulus, Strongylus, Oesophagostomum, Syngamus, Nematodirus, Heligmosomoides, Nippostrongylus, Metastrongylus, Angiostrongylus, Ancylostoma, Necator, Uncinaria, Bunostomum, Strongyloides, Steinernema, Ascaris, Parascaris, Toxocara, Toxascaris, Baylisascaris, Anisakis, Pseudoterranova, Heterakis, Wuchereria, Brugia, Onchocerca, Dirofilaria, Loa, Thelazia, Dracunculus, Gnathostoma, Enterobius, Oxyuris, Syphacia, Trichinella, Trichuris, Capillaria, Globodera, Heterodera, Meloidogyne, Anguina, Ditylenchus, Hirschmanniella, Naccobus, Pratylenchus, Radopholus, Criconema, Tylenchulus, Paratylenchus, Aphelenchus, Bursaphelenchus, Longidorus, Xiphinema, Trichodorus*, and *Paratrichodorus* nematode genera.

23. A method of expressing a polynucleotide in a *C. elegans* nematode comprising the step of:
generating a transgenie *C. elegans* nematode, cells of which comprise a transgene comprising a *C. elegans* vap-1 regulatory region operably linked to the polynucleotide; and
maintaining the *C. elegans* nematode so that expression of the first polynucleotide occurs in an amphid sheath cell.

24. The method of claim 23, wherein the polynucleotide encodes a polypeptide.

25. The method of claim 23, wherein the transgene comprises a sequence extending in a 5' up to 10 kB direction from the start codon of the *C. elegans* vap-1 gene.

26. The method of claim 23, wherein the generating step comprises injecting a polynucleotide into a *C. elegans* nematode, wherein the polynucleotide comprises a *C. elegans* vap-1 regulatory region operably linked to the polynucleotide.

27. The method of claim 23, wherein the polynucleotide encodes a detectable marker.

28. The method of claim 27, wherein the detectable marker is selected from the list consisting of: a fluorescent polypoptide, a chemiluminsecent polypeptide, an epitope tag, and an enzyme.

29. The method of claim 27, wherein the detectable marker is selected from the list consisting of: green fluorescent protein, luciferase, ehloraxnphenicol acetyl transferase, xanthine-guanine phosphoribosyl transferase, beta-galactosidase, horseradish peroxidose, alkaline phosphates; a Myc tag, and an HA tag.

30. The method of claim 27, wherein the detectable marker comprises a variant of a marker selected from the list consisting of: green fluorescent protein, luciferase, chloramphenicol acetyl transferase, xanthine-guanine phosphoribosyl transferase, beta-galactosidase, horseradish peroxidase, alkaline phosphatase, horseradish peroxidase, alkaline phosphatase, a Myc tag, and an HA tag, wherein the variant is detectable using the some detection means by which the marker of which it is a variant is detectable.

31. The method of claim 27, wherein the detectable marker is alkaline phosphatase.

32. The method of claim 23, wherein the transgene further comprises at least a portion of the coding sequence of the *C. elegans* vap-1 gene, at least a portion of an intron of the *C. elegans* vap-1 gene, at least a portion of the 3' untranslated region of the *C. elegans* vap-1 gene, or any combination of the foregoing.

* * * * *

SEQUENCE LISTING

<160> NUMBER OF SEQ ID NOS: 33

<210> SEQ ID NO 1
<211> LENGTH: 425
<212> TYPE: PRT
<213> ORGANISM: Artificial

```
<220> FEATURE:
<223> OTHER INFORMATION: Caenorhabditis elegans

<400> SEQUENCE: 1

Met Ala Val Leu Ala Val Val Leu Leu Ala Cys Leu Glu Arg Ala
1               5                   10                  15

Val Ala Gln Thr Phe Gly Cys Ser Asn Thr Lys Ile Asn Asp Gln Ala
                20                  25                  30

Arg Lys Met Phe Tyr Asp Ala His Asn Asp Ala Arg Arg Ser Met Ala
            35                  40                  45

Lys Gly Leu Glu Pro Asn Lys Cys Gly Leu Leu Ser Gly Gly Lys Asn
50                      55                  60

Val Tyr Glu Leu Asn Trp Asp Cys Glu Met Glu Ala Lys Ala Gln Glu
65                  70                  75                  80

Trp Ala Asp Gly Cys Pro Ser Ser Phe Gln Thr Phe Asp Pro Thr Trp
                85                  90                  95

Gly Gln Asn Tyr Ala Thr Tyr Met Gly Ser Ile Ala Asp Pro Leu Pro
                100                 105                 110

Tyr Ala Ser Met Ala Val Asn Gly Trp Trp Ser Glu Ile Arg Thr Val
            115                 120                 125

Gly Leu Thr Asp Pro Asp Asn Lys Tyr Thr Asn Ser Ala Met Phe Arg
130                     135                 140

Phe Ala Asn Met Ala Asn Gly Lys Ala Ser Ala Phe Gly Cys Ala Tyr
145                 150                 155                 160

Ala Leu Cys Ala Gly Lys Leu Ser Ile Asn Cys Ile Tyr Asn Lys Ile
                165                 170                 175

Gly Tyr Met Thr Asn Ala Ile Ile Tyr Glu Lys Gly Asp Ala Cys Thr
            180                 185                 190

Ser Asp Ala Glu Cys Thr Thr Tyr Ser Asp Ser Gln Cys Lys Asn Gly
            195                 200                 205

Leu Cys Tyr Lys Ala Pro Gln Ala Pro Val Val Glu Thr Phe Thr Met
210                 215                 220

Cys Pro Ser Val Thr Asp Gln Ser Asp Gln Ala Arg Gln Asn Phe Leu
225                 230                 235                 240

Asp Thr His Asn Lys Leu Arg Thr Ser Leu Ala Lys Gly Leu Glu Ala
                245                 250                 255

Asp Gly Ile Ala Ala Gly Ala Phe Ala Pro Met Ala Lys Gln Met Pro
            260                 265                 270

Lys Leu Val Lys Tyr Ser Cys Thr Val Glu Ala Asn Ala Arg Thr Trp
            275                 280                 285

Ala Lys Gly Cys Leu Tyr Gln His Ser Thr Ser Ala Gln Arg Pro Gly
290                 295                 300

Leu Gly Glu Asn Leu Tyr Met Ile Ser Ile Asn Asn Met Pro Lys Ile
305                 310                 315                 320

Gln Thr Ala Glu Asp Ser Ser Lys Ala Trp Trp Ser Glu Leu Lys Asp
                325                 330                 335

Phe Gly Val Gly Ser Asp Asn Ile Leu Thr Gln Ala Val Phe Asp Arg
            340                 345                 350

Gly Val Gly His Tyr Thr Gln Met Ala Trp Glu Gly Thr Thr Glu Ile
            355                 360                 365

Gly Cys Phe Val Glu Asn Cys Pro Thr Phe Thr Tyr Ser Val Cys Gln
370                 375                 380

Tyr Gly Pro Ala Gly Asn Tyr Met Asn Gln Leu Ile Tyr Thr Lys Gly
385                 390                 395                 400
```

```
Ser Pro Cys Thr Ala Asp Ala Asp Cys Pro Gly Thr Gln Thr Cys Ser
            405                 410                 415

Val Ala Glu Ala Leu Cys Val Ile Pro
            420                 425

<210> SEQ ID NO 2
<211> LENGTH: 1341
<212> TYPE: DNA
<213> ORGANISM: Artificial
<220> FEATURE:
<223> OTHER INFORMATION: Caenorhabditis elegans

<400> SEQUENCE: 2
atggcggtat tagcagtggt actacttcta gcatgcctgg agagagcggt tgcacagacg      60
ttcggctgct ctaacaccaa gatcaatgac caggctcgta agatgttcta tgatgctcac     120
aatgatgcaa gacgaagcat ggctaaaggg cttgagccaa acaagtgcgg actcttatct     180
ggtggaaaga atgtttatga attgaattgg gattgcgaga tggaagcaaa agctcaggaa     240
tgggcagacg gatgtcccag ctctttccag acatttgatc caacatgggg gcagaactac     300
gcgacgtaca tgggatcgat tgctgatccg cttccatacg cttccatggc tgttaatggg     360
tggtggtcgg aaattagaac cgtaggactt acggatcctg ataacaagta cactaacagt     420
gcaatgttcc gatttgctaa tatggcaaat ggtaaagctt cagcttttgg atgtgcatac     480
gcgttgtgcg caggaaaact atccatcaat tgcatttaca acaagatagg atacatgacc     540
aatgctatca tttatgaaaa aggagatgcc tgtaccagtg acgctgaatg caccacctac     600
tcagactcac aatgcaaaaa cggtctttgc tataaggcac ctcaagctcc agtcgttgag     660
actttcacaa tgtgcccttc ggtcacggac cagtcggatc aggcgcgtca aaacttcttg     720
gacacccata acaaattgcg tacaagcctt gccagggac ttgaagctga tggaattgcc     780
gctggagcat ttgcaccaat ggccaagcaa atgccaaaac tggtaaaata cagctgcaca     840
gttgaagcaa cgccagaac atgggcaaaa ggatgccttt accagcattc aacaagcgca     900
cagagaccag gactcggtga aaatctttat atgatcagca ttaacaacat gcctaaaatt     960
caaaccgcgg aggactcctc aaaggcttgg tggtccgagt tgaaagactt cggagtcggt    1020
tctgacaaca ttctgaccca gcagtttttt gatcgtggcg ttggacatta cacacaaatg    1080
gcatgggaag gaactactga aattggatgt tttgtggaga attgtccaac attcacttat    1140
tccgtatgcc aatatggtcc agcgggaaac tacatgaacc aactaatcta taccaagggc    1200
tcaccatgca cagctgacgc cgattgccca ggaacccaga catgcagtgt cgctgaagca    1260
ttatgtgtta tccccttagta aattttctat gcaactcttt gaaagtcata taaatatgc    1320 aaaaattaaa aaaaaaaaaa a                                              1341

<210> SEQ ID NO 3
<211> LENGTH: 473
<212> TYPE: PRT
<213> ORGANISM: Artificial
<220> FEATURE:
<223> OTHER INFORMATION: Caenorhabditis elegans

<400> SEQUENCE: 3

Met Asn Val Val Leu Ser Ala Val Thr Leu Phe Leu Ile Phe Arg Tyr
  1               5                  10                  15

Ala Gln Thr Val Asn Ile Glu Gly Ser Gly Gly Asn Asp Glu Leu Leu
            20                  25                  30
```

```
Glu Gln Asn Val Trp Asn Asp Val Asp Asp Lys Val Val Glu Ala Leu
            35                  40                  45
Gly Gly Leu Asp Asp Glu Leu Leu Thr Glu His Val Cys Asn Lys Ser
        50                  55                  60
Thr Ile Thr Gln Leu Gln Gln Glu Ile Ile Leu Thr Thr His Asn Glu
 65                  70                  75                  80
Leu Arg Arg Ser Leu Ala Phe Gly Lys Gln Arg Asn Lys Arg Gly Leu
                85                  90                  95
Met Asn Gly Ala Arg Asn Met Tyr Lys Leu Asp Trp Asp Cys Glu Leu
            100                 105                 110
Ala Ser Leu Ala Ala Asn Trp Ser Thr Ser Cys Pro Gln His Phe Met
        115                 120                 125
Pro Gln Ser Val Leu Gly Ser Asn Ala Gln Leu Phe Lys Arg Phe Tyr
    130                 135                 140
Phe Tyr Phe Asp Gly His Asp Ser Thr Val His Met Arg Asn Ala Met
145                 150                 155                 160
Lys Tyr Trp Trp Gln Gln Gly Glu Glu Lys Gly Asn Glu Asp Gln Lys
                165                 170                 175
Asn Arg Phe Tyr Ala Arg Arg Asn Tyr Phe Gly Trp Ala Asn Met Ala
            180                 185                 190
Lys Gly Lys Thr Tyr Arg Val Gly Cys Ser Tyr Ile Met Cys Gly Asp
        195                 200                 205
Gly Glu Ser Ala Leu Phe Thr Cys Leu Tyr Asn Glu Lys Ala Gln Cys
    210                 215                 220
Glu Lys Glu Met Ile Tyr Glu Asn Gly Lys Pro Cys Cys Glu Asp Lys
225                 230                 235                 240
Asp Cys Phe Thr Tyr Pro Gly Ser Lys Cys Leu Val Pro Glu Gly Leu
                245                 250                 255
Cys Gln Ala Pro Ser Met Val Lys Asp Asp Gly Gly Ser Phe Gln Cys
            260                 265                 270
Asp Asn Ser Leu Val Ser Asp Val Thr Arg Asn Phe Thr Leu Glu Gln
        275                 280                 285
His Asn Phe Tyr Arg Ser Arg Leu Ala Lys Gly Phe Glu Trp Asn Gly
    290                 295                 300
Glu Thr Asn Thr Ser Gln Pro Lys Ala Ser Gln Met Ile Lys Met Glu
305                 310                 315                 320
Tyr Asp Cys Met Leu Glu Arg Phe Ala Gln Asn Trp Ala Asn Asn Cys
                325                 330                 335
Val Phe Ala His Ser Ala His Tyr Glu Arg Pro Asn Gln Gly Gln Asn
            340                 345                 350
Leu Tyr Met Ser Ser Phe Ser Asn Pro Asp Pro Arg Ser Leu Ile His
        355                 360                 365
Thr Ala Val Glu Lys Trp Trp Gln Glu Leu Glu Glu Phe Gly Thr Pro
    370                 375                 380
Ile Asp Asn Val Leu Thr Pro Glu Leu Trp Asp Leu Lys Gly Lys Ala
385                 390                 395                 400
Ile Gly His Tyr Thr Gln Met Ala Trp Asp Arg Thr Tyr Arg Leu Gly
                405                 410                 415
Cys Gly Ile Ala Asn Cys Pro Lys Met Ser Tyr Val Val Cys His Tyr
            420                 425                 430
Gly Pro Ala Gly Asn Arg Lys Asn Asn Lys Ile Tyr Glu Ile Gly Asp
        435                 440                 445
Pro Cys Glu Val Asp Asp Asp Cys Pro Ile Gly Thr Asp Cys Glu Lys
```

```
                450             455             460
Thr Thr Ser Leu Cys Val Ile Ser Lys
465                 470

<210> SEQ ID NO 4
<211> LENGTH: 1422
<212> TYPE: DNA
<213> ORGANISM: Artificial
<220> FEATURE:
<223> OTHER INFORMATION: Caenorhabditis elegans

<400> SEQUENCE: 4
atgaacgtgg tcctttccgc tgtcactctt tttcttattt ttcgatatgc gcagactgtg      60
aatatagaag gcagtggagg aaatgatgag cttcttgagc agaacgtgtg gaacgatgta     120
gacgacaagg ttgtagaagc acttggtggt cttgatgatg aactgctaac cgaacatgtg     180
tgtaacaaat caacgatcac tcagctacag caggagatca tcttgacaac ccacaatgaa     240
ttacgaagat cattggcttt cggaaagcaa agaaacaaga gaggtctcat gaacggtgcg     300
agaaatatgt ataaactgga ttgggattgt gaactggcat cacttgcagc caattggtca     360
acctcctgcc ctcagcactt tatgccgcaa tcggtacttg gctccaacgc tcagcttttt     420
aagcgtttct atttttattt tgatgggcac gactctactg tacatatgcg aaacgcgatg     480
aagtattggt ggcagcaagg tgaagaaaaa ggcaatgagg atcagaaaaa tagattctat     540
gccagacgaa attattttgg atgggcaaac atggcaaaag gaaaaacata tcgagttgga     600
tgctcgtata ttatgtgcgg cgacggtgaa tctgcacttt tcacttgtct ttataacgaa     660
aaagcccaat gcgaaaaaga aatgatttac gaaaatggaa aaccctgctg tgaggataaa     720
gactgtttca catatccagg atcaaaatgt ttagtacctg aaggattatg tcaagcacct     780
tctatggtaa aggatgatgg aggaagtttc aatgtgata  actcccttgt gtcagatgtc     840
acccgcaatt tcactttgga gcaacacaat ttttatagat ctcgtcttgc aaaaggtttt     900
gaatggaatg gagaaacaaa cacttcccag ccaaaggcta gtcaaatgat caaaatggag     960
tatgactgca tgttggaacg gtttgcacaa aactgggcaa ataattgcgt ttttgcacac    1020
tcggcacatt acgaaagacc gaatcagggt cagaatctct acatgagttc tttctcaaac    1080
cctgatccta gaagccttat acatacggcc gtcgagaagt ggtggcagga attggaggag    1140
ttcggtactc caattgataa cgttctgaca cccgaattgt gggatttgaa agggaaagcg    1200
ataggacatt acactcagat ggcctgggat cgtacttacc gtcttggttg tggaatcgca    1260
aactgtccga agatgtcgta cgtggttttgt cactatgggc cagcaggcaa cagaaagaac    1320
aataaaatct atgaaatcgg ggatccttgc gaagtcgatg atgattgccc gattggaaca    1380
gattgtgaaa agacaacttc tttatgtgtg atctcaaaat aa                        1422

<210> SEQ ID NO 5
<211> LENGTH: 24
<212> TYPE: DNA
<213> ORGANISM: Artificial
<220> FEATURE:
<223> OTHER INFORMATION: Primer for Caenorhabditis elegans

<400> SEQUENCE: 5
gccaaacaag tgcggactct tatc                                              24

<210> SEQ ID NO 6
<211> LENGTH: 23
<212> TYPE: DNA
```

-continued

```
<213> ORGANISM: Artificial
<220> FEATURE:
<223> OTHER INFORMATION: Primer for Caenorhabditis elegans

<400> SEQUENCE: 6
gtgctagttt ttgacgaacc cag                                        23

<210> SEQ ID NO 7
<211> LENGTH: 18
<212> TYPE: PRT
<213> ORGANISM: Artificial
<220> FEATURE:
<223> OTHER INFORMATION: Caenorhabditis elegans

<400> SEQUENCE: 7

Met Ala Val Leu Ala Val Val Leu Leu Leu Ala Cys Leu Glu Arg Ala
1               5                   10                  15

Val Ala

<210> SEQ ID NO 8
<211> LENGTH: 21
<212> TYPE: DNA
<213> ORGANISM: Artificial
<220> FEATURE:
<223> OTHER INFORMATION: Primer for Caenorhabditis elegens

<400> SEQUENCE: 8
cacaatctgt tccaatcggg c                                          21

<210> SEQ ID NO 9
<211> LENGTH: 21
<212> TYPE: DNA
<213> ORGANISM: Artificial
<220> FEATURE:
<223> OTHER INFORMATION: Primer for Caenorhabditis elegans

<400> SEQUENCE: 9
cgtggtcctt tccgctgtca c                                          21

<210> SEQ ID NO 10
<211> LENGTH: 21
<212> TYPE: DNA
<213> ORGANISM: Artificial
<220> FEATURE:
<223> OTHER INFORMATION: Primer for Caenorhabditis elegans

<400> SEQUENCE: 10
gttctttctg ttgcctgctg g                                          21

<210> SEQ ID NO 11
<211> LENGTH: 25
<212> TYPE: DNA
<213> ORGANISM: Artificial
<220> FEATURE:
<223> OTHER INFORMATION: Primer for Caenorhabditis elegans

<400> SEQUENCE: 11
ctcctgataa cttttagagg tttgg                                      25

<210> SEQ ID NO 12
<211> LENGTH: 25
<212> TYPE: DNA
<213> ORGANISM: Artificial
<220> FEATURE:
<223> OTHER INFORMATION: Primer for Caenorhabditis elegans
```

```
<400> SEQUENCE: 12
cctaatgagc acactaccag ttttg                                          25

<210> SEQ ID NO 13
<211> LENGTH: 30
<212> TYPE: DNA
<213> ORGANISM: Artificial
<220> FEATURE:
<223> OTHER INFORMATION: Primer for Caenorhabditis elegans

<400> SEQUENCE: 13
acgcgtcgac tctccaaccc atcaaacacc                                     30

<210> SEQ ID NO 14
<211> LENGTH: 30
<212> TYPE: DNA
<213> ORGANISM: Artificial
<220> FEATURE:
<223> OTHER INFORMATION: Primer for Caenorhabditis elegans

<400> SEQUENCE: 14
cgcggatcca tctgtgaaaa tgaacgcacg                                     30

<210> SEQ ID NO 15
<211> LENGTH: 21
<212> TYPE: DNA
<213> ORGANISM: Artificial
<220> FEATURE:
<223> OTHER INFORMATION: Primer for Caenorhabditis elegans

<400> SEQUENCE: 15
tggaaagcac aatcgaggtg g                                              21

<210> SEQ ID NO 16
<211> LENGTH: 44
<212> TYPE: DNA
<213> ORGANISM: Artificial
<220> FEATURE:
<223> OTHER INFORMATION: Primer for Caenorhabditis elegans

<400> SEQUENCE: 16 acatacctt gggtcctttg gtggctggga agtgtttgtt tctc                      44

<210> SEQ ID NO 17
<211> LENGTH: 21
<212> TYPE: DNA
<213> ORGANISM: Artificial
<220> FEATURE:
<223> OTHER INFORMATION: Primers for GFP from Aequoria Victoria

<400> SEQUENCE: 17
ccaaaggacc caaaggtatg t                                              21

<210> SEQ ID NO 18
<211> LENGTH: 23
<212> TYPE: DNA
<213> ORGANISM: Artificial
<220> FEATURE:
<223> OTHER INFORMATION: Primers for GFP from Aequoria Victoria

<400> SEQUENCE: 18
tacagacaag ctgtgaccgt ctc                                            23

<210> SEQ ID NO 19
<211> LENGTH: 42
```

```
<212> TYPE: DNA
<213> ORGANISM: Artificial
<220> FEATURE:
<223> OTHER INFORMATION: Primer for Caenorhabditis elegans

<400> SEQUENCE: 19 acatacctttt gggtcctttg gaaaaagagt gacagcggaa ag                         42

<210> SEQ ID NO 20
<211> LENGTH: 21
<212> TYPE: DNA
<213> ORGANISM: Artificial
<220> FEATURE:
<223> OTHER INFORMATION: Primer for Caenorhabditis elegans

<400> SEQUENCE: 20
gtggaagtca atgggcagat t                                                 21

<210> SEQ ID NO 21
<211> LENGTH: 21
<212> TYPE: DNA
<213> ORGANISM: Artificial
<220> FEATURE:
<223> OTHER INFORMATION: Primers for GFP from Aequoria Victoria

<400> SEQUENCE: 21
gttttcaccg tcatcaccga a                                                 21

<210> SEQ ID NO 22
<211> LENGTH: 43
<212> TYPE: DNA
<213> ORGANISM: Artificial
<220> FEATURE:
<223> OTHER INFORMATION: Primer for Caenorhabditis elegans and Myc tag

<400> SEQUENCE: 22
cattttcagg aggacccttg gtgatgtgaa ttcttatggt ggc                         43

<210> SEQ ID NO 23
<211> LENGTH: 65
<212> TYPE: DNA
<213> ORGANISM: Artificial
<220> FEATURE:
<223> OTHER INFORMATION: Primer for Caenorhabditis elegans and Myc tag

<400> SEQUENCE: 23
ggcgagctct taaaggtcct cctcagaaat gagttttttgt tcagggatga cacataatgc      60
ttcag                                                                   65

<210> SEQ ID NO 24
<211> LENGTH: 10
<212> TYPE: PRT
<213> ORGANISM: Artificial
<220> FEATURE:
<223> OTHER INFORMATION: Myc tag

<400> SEQUENCE: 24

Glu Gln Lys Leu Ile Ser Glu Glu Asp Leu
1               5                   10

<210> SEQ ID NO 25
<211> LENGTH: 9
<212> TYPE: PRT
<213> ORGANISM: Artificial
<220> FEATURE:
<223> OTHER INFORMATION: Influenza virus
```

<400> SEQUENCE: 25

Tyr Pro Tyr Asp Val Pro Asp Tyr Ala
1               5

<210> SEQ ID NO 26
<211> LENGTH: 213
<212> TYPE: PRT
<213> ORGANISM: Artificial
<220> FEATURE:
<223> OTHER INFORMATION: Caenorhabditis elegans

<400> SEQUENCE: 26

Met Ala Val Leu Ala Val Val Leu Leu Leu Ala Cys Leu Glu Arg Ala
1               5                   10                  15

Val Ala Gln Thr Phe Gly Cys Ser Asn Thr Lys Ile Asn Asp Gln Ala
            20                  25                  30

Arg Lys Met Phe Tyr Asp Ala His Asn Asp Ala Arg Arg Ser Met Ala
        35                  40                  45

Lys Gly Leu Glu Pro Asn Lys Cys Gly Leu Leu Ser Gly Gly Lys Asn
    50                  55                  60

Val Tyr Glu Leu Asn Trp Asp Cys Glu Met Glu Ala Lys Ala Gln Glu
65                  70                  75                  80

Trp Ala Asp Gly Cys Pro Ser Ser Phe Gln Thr Phe Asp Pro Thr Trp
                85                  90                  95

Gly Gln Asn Tyr Ala Thr Tyr Met Gly Ser Ile Ala Asp Pro Leu Pro
            100                 105                 110

Tyr Ala Ser Met Ala Val Asn Gly Trp Trp Ser Glu Ile Arg Thr Val
        115                 120                 125

Gly Leu Thr Asp Pro Asp Asn Lys Tyr Thr Asn Ser Ala Met Phe Arg
    130                 135                 140

Phe Ala Asn Met Ala Asn Gly Lys Ala Ser Ala Phe Gly Cys Ala Tyr
145                 150                 155                 160

Ala Leu Cys Ala Gly Lys Leu Ser Ile Asn Cys Ile Tyr Asn Lys Ile
                165                 170                 175

Gly Tyr Met Thr Asn Ala Ile Ile Tyr Glu Lys Gly Asp Ala Cys Thr
            180                 185                 190

Ser Asp Ala Glu Cys Thr Thr Tyr Ser Asp Ser Gln Cys Lys Asn Gly
        195                 200                 205

Leu Cys Tyr Lys Ala
    210

<210> SEQ ID NO 27
<211> LENGTH: 212
<212> TYPE: PRT
<213> ORGANISM: Artificial
<220> FEATURE:
<223> OTHER INFORMATION: Caenorhabditis elegans

<400> SEQUENCE: 27

Pro Gln Ala Pro Val Val Glu Thr Phe Thr Met Cys Pro Ser Val Thr
1               5                   10                  15

Asp Gln Ser Asp Gln Ala Arg Gln Asn Phe Leu Asp Thr His Asn Lys
            20                  25                  30

Leu Arg Thr Ser Leu Ala Lys Gly Leu Glu Ala Asp Gly Ile Ala Ala
        35                  40                  45

Gly Ala Phe Ala Pro Met Ala Lys Gln Met Pro Lys Leu Val Lys Tyr
    50                  55                  60

```
Ser Cys Thr Val Glu Ala Asn Ala Arg Thr Trp Ala Lys Gly Cys Leu
 65                  70                  75                  80

Tyr Gln His Ser Thr Ser Ala Gln Arg Pro Gly Leu Gly Glu Asn Leu
                 85                  90                  95

Tyr Met Ile Ser Ile Asn Asn Met Pro Lys Ile Gln Thr Ala Glu Asp
            100                 105                 110

Ser Ser Lys Ala Trp Trp Ser Glu Leu Lys Asp Phe Gly Val Gly Ser
        115                 120                 125

Asp Asn Ile Leu Thr Gln Ala Val Phe Asp Arg Gly Val Gly His Tyr
    130                 135                 140

Thr Gln Met Ala Trp Glu Gly Thr Thr Glu Ile Gly Cys Phe Val Glu
145                 150                 155                 160

Asn Cys Pro Thr Phe Thr Tyr Ser Val Cys Gln Tyr Gly Pro Ala Gly
                165                 170                 175

Asn Tyr Met Asn Gln Leu Ile Tyr Thr Lys Gly Ser Pro Cys Thr Ala
            180                 185                 190

Asp Ala Asp Cys Pro Gly Thr Gln Thr Cys Ser Val Ala Glu Ala Leu
        195                 200                 205

Cys Val Ile Pro
210
```

<210> SEQ ID NO 28
<211> LENGTH: 268
<212> TYPE: PRT
<213> ORGANISM: Artificial
<220> FEATURE:
<223> OTHER INFORMATION: Caenorhabditis elegans

<400> SEQUENCE: 28

```
Met Asn Val Val Leu Ser Ala Val Thr Leu Phe Leu Ile Phe Arg Tyr
  1               5                  10                  15

Ala Gln Thr Val Asn Ile Glu Gly Ser Gly Gly Asn Asp Glu Leu Leu
                 20                  25                  30

Glu Gln Asn Val Trp Asn Asp Val Asp Asp Lys Val Val Glu Ala Leu
             35                  40                  45

Gly Gly Leu Asp Asp Glu Leu Leu Thr Glu His Val Cys Asn Lys Ser
 50                  55                  60

Thr Ile Thr Gln Leu Gln Gln Glu Ile Ile Leu Thr Thr His Asn Glu
 65                  70                  75                  80

Leu Arg Arg Ser Leu Ala Phe Gly Lys Gln Arg Asn Lys Arg Gly Leu
                 85                  90                  95

Met Asn Gly Ala Arg Asn Met Tyr Lys Leu Asp Trp Asp Cys Glu Leu
            100                 105                 110

Ala Ser Leu Ala Ala Asn Trp Ser Thr Ser Cys Pro Gln His Phe Met
        115                 120                 125

Pro Gln Ser Val Leu Gly Ser Asn Ala Gln Leu Phe Lys Arg Phe Tyr
    130                 135                 140

Phe Tyr Phe Asp Gly His Asp Ser Thr Val His Met Arg Asn Ala Met
145                 150                 155                 160

Lys Tyr Trp Trp Gln Gln Gly Glu Glu Lys Gly Asn Glu Asp Gln Lys
                165                 170                 175

Asn Arg Phe Tyr Ala Arg Arg Asn Tyr Phe Gly Trp Ala Asn Met Ala
            180                 185                 190

Lys Gly Lys Thr Tyr Arg Val Gly Cys Ser Tyr Ile Met Cys Gly Asp
        195                 200                 205
```

```
Gly Glu Ser Ala Leu Phe Thr Cys Leu Tyr Asn Glu Lys Ala Gln Cys
        210                 215                 220

Glu Lys Glu Met Ile Tyr Glu Asn Gly Lys Pro Cys Cys Glu Asp Lys
225                 230                 235                 240

Asp Cys Phe Thr Tyr Pro Gly Ser Lys Cys Leu Val Pro Glu Gly Leu
                245                 250                 255

Cys Gln Ala Pro Ser Met Val Lys Asp Asp Gly Gly
        260                 265

<210> SEQ ID NO 29
<211> LENGTH: 205
<212> TYPE: PRT
<213> ORGANISM: Artificial
<220> FEATURE:
<223> OTHER INFORMATION: Caenorhabditis elegans

<400> SEQUENCE: 29

Ser Phe Gln Cys Asp Asn Ser Leu Val Ser Asp Val Thr Arg Asn Phe
1               5                   10                  15

Thr Leu Glu Gln His Asn Phe Tyr Arg Ser Arg Leu Ala Lys Gly Phe
            20                  25                  30

Glu Trp Asn Gly Glu Thr Asn Thr Ser Gln Pro Lys Ala Ser Gln Met
        35                  40                  45

Ile Lys Met Glu Tyr Asp Cys Met Leu Glu Arg Phe Ala Gln Asn Trp
    50                  55                  60

Ala Asn Asn Cys Val Phe Ala His Ser Ala His Tyr Glu Arg Pro Asn
65                  70                  75                  80

Gln Gly Gln Asn Leu Tyr Met Ser Ser Phe Ser Asn Pro Asp Pro Arg
                85                  90                  95

Ser Leu Ile His Thr Ala Val Glu Lys Trp Trp Gln Glu Leu Glu Glu
            100                 105                 110

Phe Gly Thr Pro Ile Asp Asn Val Leu Thr Pro Glu Leu Trp Asp Leu
        115                 120                 125

Lys Gly Lys Ala Ile Gly His Tyr Thr Gln Met Ala Trp Asp Arg Thr
130                 135                 140

Tyr Arg Leu Gly Cys Gly Ile Ala Asn Cys Pro Lys Met Ser Tyr Val
145                 150                 155                 160

Val Cys His Tyr Gly Pro Ala Gly Asn Arg Lys Asn Asn Lys Ile Tyr
                165                 170                 175

Glu Ile Gly Asp Pro Cys Glu Val Asp Asp Cys Pro Ile Gly Thr
            180                 185                 190

Asp Cys Glu Lys Thr Thr Ser Leu Cys Val Ile Ser Lys
        195                 200                 205

<210> SEQ ID NO 30
<211> LENGTH: 218
<212> TYPE: PRT
<213> ORGANISM: Artificial
<220> FEATURE:
<223> OTHER INFORMATION: Ancylostoma caninum

<400> SEQUENCE: 30

Met Phe Ser Pro Val Ile Val Ser Val Ile Phe Thr Ile Ala Phe Cys
1               5                   10                  15

Asp Ala Ser Pro Ala Arg Asp Gly Phe Gly Cys Ser Asn Ser Gly Ile
            20                  25                  30

Thr Asp Lys Asp Arg Gln Ala Phe Leu Asp Phe His Asn Asn Ala Arg
```

-continued

```
                35                  40                  45
Arg Arg Val Ala Lys Gly Val Glu Asp Ser Asn Ser Gly Lys Leu Asn
     50                  55                  60
Pro Ala Lys Asn Met Tyr Lys Leu Ser Trp Asp Cys Ala Met Glu Gln
 65                  70                  75                  80
Gln Leu Gln Asp Ala Ile Gln Ser Cys Pro Ser Ala Phe Ala Gly Ile
                 85                  90                  95
Gln Gly Val Ala Gln Asn Val Met Ser Trp Ser Ser Gly Gly Phe
                100                 105                 110
Pro Asp Pro Ser Val Lys Ile Glu Gln Thr Leu Ser Gly Trp Trp Ser
                115                 120                 125
Gly Ala Lys Lys Asn Gly Val Gly Pro Asp Asn Lys Tyr Asn Gly Gly
    130                 135                 140
Gly Leu Phe Ala Phe Ser Asn Met Val Tyr Ser Glu Thr Thr Lys Leu
145                 150                 155                 160
Gly Cys Ala Tyr Lys Val Cys Gly Thr Lys Leu Ala Val Ser Cys Ile
                165                 170                 175
Tyr Asn Gly Val Gly Tyr Ile Thr Asn Gln Pro Met Trp Glu Thr Gly
                180                 185                 190
Gln Ala Cys Lys Thr Gly Ala Asp Cys Ser Thr Tyr Lys Asn Ser Gly
    195                 200                 205
Cys Glu Asp Gly Leu Cys Thr Lys Gly Pro
    210                 215

<210> SEQ ID NO 31
<211> LENGTH: 206
<212> TYPE: PRT
<213> ORGANISM: Artificial
<220> FEATURE:
<223> OTHER INFORMATION: Ancylostoma caninum

<400> SEQUENCE: 31

Asp Val Pro Glu Thr Asn Gln Gln Cys Pro Ser Asn Thr Gly Met Thr
 1               5                  10                  15
Asp Ser Val Arg Asp Thr Phe Leu Ser Val His Asn Glu Phe Arg Ser
                20                  25                  30
Ser Val Ala Arg Gly Leu Glu Pro Asp Ala Leu Gly Gly Asn Ala Pro
                35                  40                  45
Lys Ala Ala Lys Met Leu Lys Met Val Tyr Asp Cys Glu Val Glu Ala
     50                  55                  60
Ser Ala Ile Arg His Gly Asn Lys Cys Val Tyr Gln His Ser His Gly
 65                  70                  75                  80
Glu Asp Arg Pro Gly Leu Gly Glu Asn Ile Tyr Lys Thr Ser Val Leu
                85                  90                  95
Lys Phe Asp Lys Asn Lys Ala Ala Lys Gln Ala Ser Gln Leu Trp Trp
                100                 105                 110
Asn Glu Leu Lys Glu Phe Gly Val Gly Pro Ser Asn Val Leu Thr Thr
                115                 120                 125
Ala Leu Trp Asn Arg Pro Gly Met Gln Ile Gly His Tyr Thr Gln Met
    130                 135                 140
Ala Trp Asp Thr Thr Tyr Lys Leu Gly Cys Ala Val Val Phe Cys Asn
145                 150                 155                 160
Asp Phe Thr Phe Gly Val Cys Gln Tyr Gly Pro Gly Gly Asn Tyr Met
                165                 170                 175
Gly His Val Ile Tyr Thr Met Gly Gln Pro Cys Ser Gln Cys Ser Pro
```

```
                180              185              190
Gly Ala Thr Cys Ser Val Thr Glu Gly Leu Cys Ser Ala Pro
        195                 200                 205

<210> SEQ ID NO 32
<211> LENGTH: 207
<212> TYPE: PRT
<213> ORGANISM: Artificial
<220> FEATURE:
<223> OTHER INFORMATION: Caenorhabditis elegans

<400> SEQUENCE: 32

Met Asn Tyr Leu Leu Val Val Ala Leu Ala Val Gly Cys Ser Ala
1               5                   10                  15

Asp Phe Gly Ser Ser Gly Gln Asn Gly Ile Ile Asn Ala His Asn Thr
            20                  25                  30

Leu Arg Ser Lys Ile Ala Lys Gly Thr Tyr Val Ala Lys Gly Thr Gln
        35                  40                  45

Lys Ser Pro Gly Thr Asn Leu Leu Lys Met Lys Trp Asp Ser Ala Val
    50                  55                  60

Ala Ala Ser Ala Gln Asn Tyr Ala Asn Gly Cys Pro Thr Gly His Ser
65                  70                  75                  80

Gly Asp Ala Gly Leu Gly Glu Asn Leu Tyr Trp Tyr Trp Thr Ser Gly
                85                  90                  95

Ser Leu Gly Asp Leu Asn Gln Tyr Gly Ser Ala Ser Ala Ser Trp
            100                 105                 110

Glu Lys Glu Phe Gln Asp Tyr Gly Trp Lys Ser Asn Leu Met Thr Ile
        115                 120                 125

Asp Leu Phe Asn Thr Gly Ile Gly His Ala Thr Gln Met Ala Trp Ala
    130                 135                 140

Lys Ser Asn Leu Ile Gly Cys Gly Val Lys Asp Cys Gly Arg Asp Ser
145                 150                 155                 160

Asn Gly Leu Val Lys Val Thr Val Val Cys Gln Tyr Lys Pro Gln Gly
                165                 170                 175

Asn Phe Ile Asn Gln Tyr Ile Tyr Val Ser Gly Ala Thr Cys Ser Gly
            180                 185                 190

Cys Pro Ser Gly Thr Ser Cys Glu Thr Ser Thr Gly Leu Cys Val
        195                 200                 205

<210> SEQ ID NO 33
<211> LENGTH: 231
<212> TYPE: PRT
<213> ORGANISM: Artificial
<220> FEATURE:
<223> OTHER INFORMATION: Meloidogyne incognita

<400> SEQUENCE: 33

Met Ser Asn Lys Leu Ile Ile Ser Ile Leu Ile Leu Thr Ile Ile Tyr
1               5                   10                  15

Thr Val Val Asn Ser Leu Thr Val Pro Glu Gln Asn Ala Val Val Asp
            20                  25                  30

Cys Ile Asn Lys Tyr Arg Ser Gln Leu Ala Asn Gly Lys Thr Lys Asn
        35                  40                  45

Lys Asn Gly Gly Asn Phe Pro Ser Gly Lys Asp Ile Leu Glu Val Ser
    50                  55                  60

Tyr Ser Lys Asp Leu Glu Lys Ser Ala Gln Arg Trp Ala Asn Lys Cys
65                  70                  75                  80
```

-continued

```
Ile Phe Asp His Asn Gly Thr Asp Leu Tyr Ser Gly Gly Lys Phe Tyr
            85                  90              95

Gly Glu Asn Leu Tyr Leu Asp Gly Asp Phe Glu His Lys Asn Ile Thr
            100             105              110

Gln Leu Met Ile Asp Ala Cys Asn Ala Trp Trp Gly Glu Ser Thr Thr
        115             120              125

Asp Gly Val Pro Pro Ser Trp Ile Asn Asn Phe Leu Pro Thr Asp Asn
    130             135              140

Lys Glu Asn Asp Glu Lys Phe Glu Ala Val Gly His Trp Thr Gln Met
145                 150              155              160

Ala Trp Ala Lys Thr Tyr Gln Ile Gly Cys Ala Leu Lys Val Cys His
            165             170              175

Lys Pro Asp Cys Asn Gly Asn Leu Ile Asp Cys Arg Tyr Tyr Pro Gly
            180             185              190

Gly Asn Gly Met Gly Ser Pro Ile Tyr Gln Gln Gly Lys Pro Ala Ser
        195             200              205

Gly Cys Gly Lys Ala Gly Pro Ser Thr Lys Tyr Ser Gly Leu Cys Lys
    210             215              220

Pro Asp Pro His Gln Asn Asn
225                 230
```